US00RE49446E

(19) United States
(12) Reissued Patent
Godbout et al.

(10) Patent Number: US RE49,446 E
(45) Date of Reissued Patent: Mar. 7, 2023

(54) OXADIAZOLOPYRIDINE DERIVATIVES FOR USE AS GHRELIN O-ACYL TRANSFERASE (GOAT) INHIBITORS

(71) Applicant: Boehringer Ingelheim International GmbH, Ingelheim am Rhein (DE)

(72) Inventors: Cédrickx Godbout, Attenweiler (DE); Thomas Trieselmann, Mettenberg (DE); Viktor Vintonyak, Warthausen (DE)

(73) Assignee: Boehringer Ingelheim International GmbH, Ingelheim am Rhein (DE)

(21) Appl. No.: 17/069,940

(22) Filed: Oct. 14, 2020

Related U.S. Patent Documents

Reissue of:
(64) Patent No.: 10,308,667
Issued: Jun. 4, 2019
Appl. No.: 15/974,882
Filed: May 9, 2018

U.S. Applications:
(62) Division of application No. 15/664,119, filed on Jul. 31, 2017, now Pat. No. 9,994,591.

(30) Foreign Application Priority Data

Aug. 5, 2016 (EP) ..... 16183047

(51) Int. Cl.
*C07D 519/00* (2006.01)
*A61K 31/437* (2006.01)
*C07D 491/048* (2006.01)
*C07D 498/04* (2006.01)

(52) U.S. Cl.
CPC ..... *C07D 519/00* (2013.01); *A61K 31/437* (2013.01); *C07D 491/048* (2013.01); *C07D 498/04* (2013.01)

(58) Field of Classification Search
CPC ..... C07D 519/00; C07D 491/048; C07D 498/04; A61K 31/437; A61P 3/04; A61P 3/10
See application file for complete search history.

(56) References Cited

U.S. PATENT DOCUMENTS 10,093,651 B2 10/2018 Galka et al.
11,136,337 B2 * 10/2021 Trieselmann ..... A61P 3/10
11,254,688 B2 * 2/2022 Trieselmann ..... A61P 3/10
11,319,310 B2 * 5/2022 Trieselmann ..... A61K 31/437
2015/0018547 A1 * 1/2015 Takakura ..... C07D 333/60 544/146

FOREIGN PATENT DOCUMENTS

WO 2013125732 A1 8/2013
WO 2015073281 A1 5/2015
WO 2016044467 A1 3/2016
WO 2016168225 A1 10/2016
WO 2019149657 A1 8/2019
WO 2019149659 A1 8/2019
WO 2019149660 A1 8/2019
WO 20191499660 8/2019

OTHER PUBLICATIONS

Kuppens, Elevatede Ratio of acylated to unacylated ghrelin in children and young adults with Prader-Willi syndrome, Endocrine, Human Press, vol. 50, 2015, p. 633-642.
International Search Report and Written opinion for PCT2017/069274 dated Sep. 15, 2017.

* cited by examiner

*Primary Examiner* — Jerry D Johnson
(74) *Attorney, Agent, or Firm* — David L. Kershner

(57) ABSTRACT

The present invention relates to compounds of general formula I,

I wherein the groups $R^1$, $R^2$ and n are defined as in claim 1, which have valuable pharmacological properties, in particular bind to ghrelin O-acyl transferase (GOAT) and modulate its activity. The compounds are suitable for treatment and prevention of diseases which can be influenced by this receptor, such as metabolic diseases, in particular obesity.

37 Claims, No Drawings

OXADIAZOLOPYRIDINE DERIVATIVES FOR USE AS GHRELIN O-ACYL TRANSFERASE (GOAT) INHIBITORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to novel oxadiazolopyridine derivatives, that are inihibitors of the ghrelin O-acyl transferase (GOAT), to processes for their preparation, to pharmaceutical compositions containing these compounds and to their medical use for the prophylaxis and/or treatment of diseases which can be influenced by the modulation of the function of the ghrelin O-acyl transferase (GOAT). Particularly, the pharmaceutical compositions of the invention are suitable for the prophylaxis and/or therapy of metabolic diseases, such as obesity, including, but not limited to obesity in patients suffering from Prader-Willi-Syndrome (PWS), insulin resistance and diabetes, particularly type 2 diabetes.

BACKGROUND OF THE INVENTION

Ghrelin O-Acyltransferase (GOAT) is a member of the membrane-bound O-acyl transferase (MBOAT) protein family, and the only enzyme in humans capable of promoting an acylation reaction on the peptide hormone ghrelin. By linking a medium-chain fatty acid to the Serine-3 position of the 28-amino acid peptide, GOAT converts unacylated ghrelin (UAG) to acylated ghrelin (AG) which is the natural ligand of the ghrelin receptor GHSR1a (growth hormone secretagogue receptor 1a). The ghrelin receptor is expressed in various areas of the brain involved in energy homeostasis. Activation of the receptor by AG results in stimulation of neuronal pathways leading to increased food intake, fat deposition and weight gain thus linking the ghrelin system to obesity. In humans, AG in plasma peaks immediately before mealtimes and drops in response to food intake (D. E. Cummings et al., Diabetes (2001) 50(8), 1714-1719). Infusion of AG has been shown to increase food intake in lean and obese subjects (M. R. Druce et al., Int. J. Obes. (2005), 29(9), 1130-1136). So far no receptor has been identified for UAG, but it has been shown to have functional antagonistic effects to AG at least with respect to its metabolic properties (W. Zhang et al., Endocrinology (2008) 149 (9), 4710-4716). Since an inhibitor of GOAT would substantially diminish the level of the GHSR1a ligand AG and concomitantly increase the functional antagonist UAG, it would be useful for the treatment of obesity as an adjunct to a reduced-calorie diet and increased physical activity for chronic weight management.

Insatiable hunger and severe obesity are characteristic features of the Prader-Willi-Syndrome (PWS), a genetically caused orphan disease with a complex pathology. AG levels in plasma of PWS subjects are elevated and AG/UAG ratios are increased suggesting a causal relationship (N. Wierup et al., Regulatory Peptides (2002) 107, 63-69; R. J. Kuppens et al., Endocrine (2015) 50(3), 633-642). Therefore GOAT inhibitors may be effective in reducing food craving behavior and body weight in PWS patients ameliorating one major burden affecting the patients and their families.

Furthermore the ghrelin system seems to play a major role in glucose homeostasis. Administration of AG to human subjects leads to suppression of glucose-induced insulin secretion and an increase in plasma glucose. Infusion of UAG is able to counteract the hyperglycemic effect of AG (F. Broglio et al., J. Clin. Endocrinol. Metab. (2004) 89, 3062-3065). The expression of GOAT, ghrelin and GHSR1a in human pancreatic islets suggests a paracrine role on insulin secretion (A. DelParigi et al., J. Clin. Endocrinol. Metab. (2002) 87(12), 5461-5464). In addition UAG promotes pancreatic β-cell and human islet cell survival in vitro (R. Granata et al., Endocrinology (2007) 148(2), 512-529) and prevents diabetes in streptozotocin treated rats (R. Granata et al., J. Med. Chem. (2012) 55(6), 2585-2596). Thus treatment with a GOAT inhibitor is expected to improve glucose homeostasis in patients with type 2 diabetes or obese with impaired glucose tolerance.

OBJECT OF THE PRESENT INVENTION

The object of the present invention is to provide new compounds, hereinafter described as compounds of formula I, in particular new oxadiazolopyridine derivatives, which are active with regard to the ghrelin O-acyl transferase (GOAT), notably they are ghrelin O-acyl transferase (GOAT) inhibitors.

A further object of the present invention is to provide new compounds, in particular oxadiazolopyridine derivatives, which have an inhibiting effect on ghrelin O-acyl transferase (GOAT) in vitro and/or in vivo and possess suitable pharmacological and pharmacokinetic properties to use them as medicaments.

A further object of the present invention is to provide effective ghrelin O-acyl transferase (GOAT) inhibitors, in particular for the treatment of metabolic disorders, for obesity, including, but not limited to obesity in patients suffering from Prader-Willi-Syndrome (PWS), insulin resistance and diabetes, in particular type 2 diabetes mellitus.

A further object of the present invention is to provide methods for treating a disease or condition mediated by the inhibition of ghrelin O-acyl transferase (GOAT) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

Ghrelin O-acyl transferase (GOAT) inhibitors are known in the art, see for example the compounds disclosed in WO 2013/125732 and WO 2015/073281. The oxadiazolopyridine derivatives of the present invention are structurally quite different and may provide several advantages, such as enhanced potency, high metabolic and/or chemical stability, high selectivity and tolerability, enhanced solubility, the ability to cross the blood-brain barrier and the possibility to form stable salts.

SUMMARY OF THE INVENTION

In a first aspect, the invention relates to a compound of formula (I)

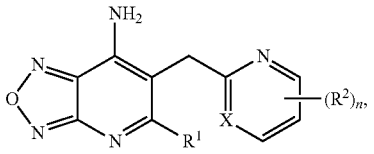

wherein

X is CH or N;

$R^1$ is selected from the group $R^1$-G1 consisting of $CH_3$, —$CH_2OH$ and Cl;

$R^2$ is independently of each other selected from the group $R^2$-G1 consisting of H, F, Cl, Br, I, CN, $C_{1-6}$-alkyl, $C_{3-7}$-cycloalkyl, OH, —O—($C_{1-6}$-alkyl), —O—($C_{3-7}$-cycloalkyl), —O—($C_{1-3}$-alkyl)-($C_{3-7}$-cycloalkyl), —O-heterocyclyl, —O—($C_{1-3}$-alkyl)-heterocyclyl, —O-aryl, —O-heteroaryl, —S—($C_{1-3}$-alkyl), —SO—($C_{1-3}$-alkyl), —$SO_2$—($C_{1-3}$-alkyl), —$NH_2$, —NH—($C_{1-6}$-alkyl), —NH—($C_{3-6}$-cycloalkyl), —NH—($C_{1-3}$-alkyl)-heterocyclyl, —NH—($C_{1-6}$-alkyl)-C(=O)—$NH_2$, —C(=O)—$NH_2$, —C(=O)—NH—($C_{1-3}$-alkyl), —C(=O)—N($C_{1-3}$-alkyl)$_2$, —C(=O)OH, —C(=O)—O—($C_{1-4}$-alkyl), —C(=O)—($C_{1-4}$-alkyl), —$C_{1-3}$-alkyl-C(=O)—O—($C_{1-4}$-alkyl), heterocyclyl, heteroaryl and 5,6-dihydro-4H-pyrrolo[1,2-b]pyrazol-3-yl, wherein each alkyl or cycloalkyl group is optionally independently substituted with one or more substituents selected from the group consisting of F, CN and OH, and wherein each heterocyclyl group is selected from the group consisting of mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from F, OH and $C_{1-3}$-alkyl, wherein each aryl group is selected from a group consisting of phenyl and naphthyl, and wherein each heteroaryl group is selected from a 5-membered aromatic cycle containing 1 or 2 heteroatoms independently selected from N, O and S or from a 6-membered aromatic cycle containing 1 or 2 N, and wherein each aryl or heteroaryl group is optionally substituted with 1 or 2 substituents independently selected from a group consisting of F, CN and $C_{1-3}$-alkyl, which is optionally substituted with one or more F;

or, if two groups $R^2$ are attached to adjacent C atoms of the pyridine or pyrimidine group, they may be linked with each other and together form a —O—$CH_2$—O—, —O—$CH_2$—$CH_2$—O— or —O—$CH_2$—$CH_2$—$CH_2$—O— bridge, in which 1 or 2H atoms may be replaced with F or $C_{1-3}$-alkyl; and n is 1, 2 or 3;

wherein each of the above-mentioned alkyl groups may be substituted with one or more F;

the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5H atoms or, more preferred, 1 to 3H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by inhibiting ghrelin O-acyl transferase (GOAT) in a patient in need thereof characterized in that a compound of general formula I or a pharmaceutically acceptable salt thereof is administered to the patient.

According to another aspect of the invention, there is provided a method for treating a metabolic disease or disorder, such as obesity, including, but not limited to obesity in patients suffering from Prader-Willi-Syndrome, insulin resistance and diabetes, in particular type 2 diabetes mellitus, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the inhibition of ghrelin O-acyl transferase (GOAT) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the inhibition of ghrelin O-acyl transferase (GOAT).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly X, $R^1$, $R^2$ and n are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

X:

X is preferably CH or N.

According to one embodiment, X is CH.

According to another embodiment, X is N.

$R^1$:

$R^1$-G1:

The group $R_1$ is preferably selected from the group $R^1$-G1 as deinfed hereinbefore.

$R^1$-G2:

In one embodiment the group $R^1$ is selected from the group $R^1$-G2 consisting of $CH_3$ and Cl.

$R^1$-G3:

In another embodiment the group $R^1$ is selected from the group $R^1$-G3 consisting of $CH_3$ and —$CH_2OH$.

$R^1$-G4:

In another embodiment the group $R^1$ is selected from the group $R^1$-G4 consisting of —$CH_2OH$ and Cl.

$R^1$-G5:

In another embodiment the group $R^1$ is selected from the group $R^1$-G5 consisting of $CH_3$.

$R^1$-G6:

In another embodiment the group $R^1$ is selected from the group $R^1$-G6 consisting of —$CH_2OH$.

$R^1$-G7:

In another embodiment the group $R^1$ is selected from the group $R^1$-G7 consisting of Cl.

$R^2$:

$R^2$-G1:

The group $R^2$ is preferably selected from the group $R^2$-G1 as defined hereinbefore.

$R^2$-G2:

In another embodiment the group $R^2$ is independently of each other selected from the group $R^2$-G2 consisting of H, F, Cl, Br, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), —O-heterocyclyl, —O—($C_{1-3}$-alkyl)-heterocyclyl, —O-aryl, —O-heteroaryl, —S—($C_{1-3}$-alkyl), —$SO_2$—($C_{1-3}$-alkyl), —$NH_2$, —NH—($C_{1-6}$-alkyl), —NH—($C_{3-6}$-cycloalkyl), —NH—($C_{1-3}$-alkyl)-heterocyclyl, —NH—($C_{1-6}$-alkyl)-C(═O)—$NH_2$, —C(═O)—$NH_2$, —C(═O)—NH—($C_{1-3}$-alkyl), —C(═O)—($C_{1-4}$-alkyl), —$C_{1-3}$-alkyl-C(═O)—O—($C_{1-4}$-alkyl), heterocyclyl, heteroaryl and 5,6-dihydro-4H-pyrrolo[1,2-b]pyrazol-3-yl, wherein each alkyl or cycloalkyl group is optionally independently substituted with one or more substituents selected from the group consisting of F, CN and OH, and wherein each heterocyclyl group is selected from a mono- or spirocyclic 4-7-membered cycloalkyl group, in which 1, 2 or 3 $CH_2$-groups are independently of each other replaced by O, S, NH or C═O, and wherein each heterocyclyl group is optionally substituted with 1 or 2 substituents independently of each other selected from F, OH and $C_{1-3}$-alkyl, wherein each aryl group is selected from a group consisting of phenyl and naphthyl, and wherein each heteroaryl group is selected from a 5-membered aromatic cycle containing 1 or 2 heteroatoms independently selected from N, O and S or from a 6-membered aromatic cycle containing 1 or 2 N, and wherein each aryl or heteroaryl group is optionally substituted with 1 or 2 substituents independently selected from a group consisting of F and $C_{1-3}$-alkyl, which is optionally substituted with one or more F;

or, if two groups $R^2$ are attached to adjacent C atoms of the pyridine or pyrimidine group, they may be linked with each other and together form a —O—$CH_2$—O—, —O—$CH_2$—$CH_2$—O— or —O—$CH_2$—$CH_2$—$CH_2$—O— bridge.

$R^2$-G3:

In another embodiment the group $R^2$ is independently of each other selected from the group $R^2$-G3 consisting of F, Cl, Br, CN, $C_{1-3}$-alkyl, $C_{3-6}$-cycloalkyl, —O—($C_{1-4}$-alkyl), —O—$CH_2$-cyclopropyl, —O—$CH_2$-heterocyclyl, —O-phenyl, —O-heteroaryl, —S—$CH_3$, —$NH_2$, —NH—($C_{1-4}$-alkyl), —NH—($C_{3-5}$-cycloalkyl), —NH—($CH_2$-heterocyclyl), —NH—($C_{1-4}$-alkyl)-C(═O)—$NH_2$, —C(═O)—NH—($C_{1-3}$-alkyl), —C(═O)—($C_{1-4}$-alkyl), heterocyclyl, heteroaryl and 5,6-dihydro-4H-pyrrolo[1,2-b]pyrazol-3-yl, wherein each alkyl or cycloalkyl group is optionally independently substituted with one to three F atoms or with one CN or one OH, and wherein each heterocyclyl group is selected from a group consisting of oxetanyl, tetrahydrofuranyl, azetidinyl, pyrrolidinyl, morpholinyl and 1,4-diazepan-5-one, and wherein each heterocyclyl group is optionally substituted with 1 or 2 substituents independently of each other selected from F, OH and $CH_3$, wherein each heteroaryl group is selected from a group consisting of furanyl, isoxazolyl, thiazolyl and pyrazolyl, and wherein each heteroaryl group is optionally substituted with 1 or 2 substituents independently selected from a group consisting of F, $CH_3$ and $CF_3$.

$R^2$-G4:

In another embodiment the group $R^2$ is independently of each other selected from the group $R^2$-G4 consisting of F, Cl, Br, CN, $CH_3$, $C_{3-5}$-cycloalkyl, —O—($C_{1-4}$-alkyl), —O—$CH_2$-heterocyclyl, —O-phenyl, —S—$CH_3$, —$NH_2$, —NH—($C_{1-4}$-alkyl), —NH—($C_{3-5}$-cycloalkyl), —NH—($CH_2$-heterocyclyl), —NH—($C_{1-4}$-alkyl)-C(═O)—$NH_2$, heterocyclyl, heteroaryl and 5,6-dihydro-4H-pyrrolo[1,2-b]pyrazol-3-yl, wherein each alkyl or cycloalkyl group is optionally independently substituted with one to three F atoms or with one CN or one OH, and wherein each heterocyclyl group is selected from a group consisting of oxetanyl, azetidinyl, pyrrolidinyl, morpholinyl and 1,4-diazepan-5-one, and wherein each heterocyclyl group is optionally substituted with 1 or 2 substituents independently selected from F, OH and $CH_3$, and wherein each heteroaryl group is selected from a group consisting of furanyl and thiazolyl.

$R^2$-G5:

In another embodiment the group $R^2$ is independently selected from the group $R^2$-G5 consisting of:

F, Cl, Br, —CN, —$CF_3$,

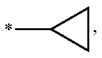

—O —$CH_3$, —O—$CHF_2$, —O—$CH_2$—$CH_2$—F, —O—$CH_2$—$CHF_2$, —O—$CH_2$—$CF_3$, —O—$CH_2$—$CH_2$—$CH_2$—F, —O—$CH_2$—$CF_2$—$CH_3$,

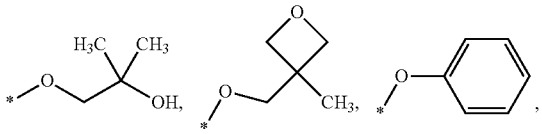

—S—$CH_3$, —$NH_2$, —NH—$CH_2$—$CH_2$—$CH_2$—F, —NH—$CH_2$—$CH_2$—$CHF_2$,

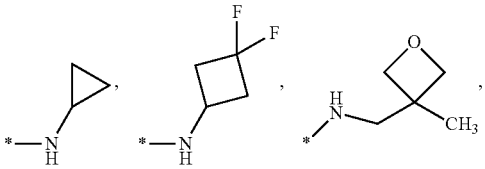

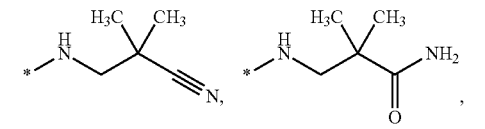

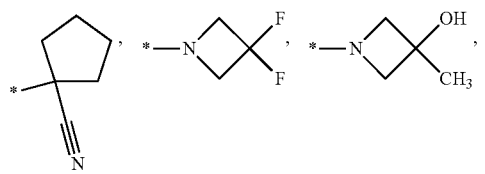

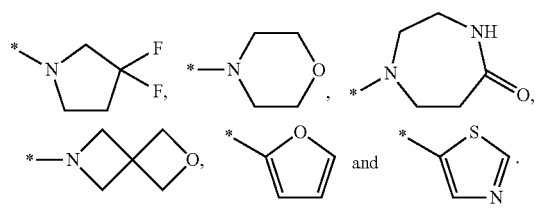

$R^2$-G6:

In another embodiment the group $R^2$ is independently selected from the group $R^2$-G6 consisting of H, F, Cl, Br, CN, —$CF_3$, —$CHF_2$, —$CH_2F$, —O—$CF_3$, —O—$CHF_2$, —O—$CH_2F$, —O—$CH_3$, —$NH_2$, —CO—$NH_2$, —$CO_2H$.

n

The index n is an integer selected from 1, 2 and 3.

Preferably, n is 2 or 3.

In another embodiment, n is 1 or 2.

More preferably, n is 2.

The following preferred embodiments of compounds of the formula I are described using generic formulae I.1 to I.11, wherein any tautomers, solvates, hydrates and salts thereof, in particular the pharmaceutically acceptable salts thereof, are encompassed. $R^{2a}$ and $R^{2b}$ are as defined for $R^2$.

(I.1)

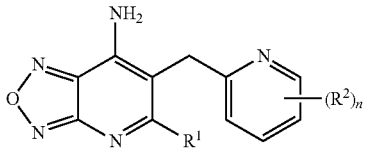

-continued (I.2)

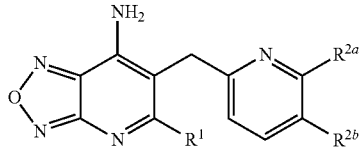

(I.3)

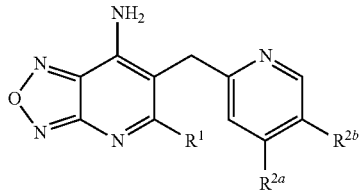

(I.4)

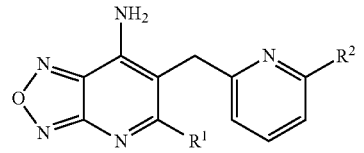

(I.5)

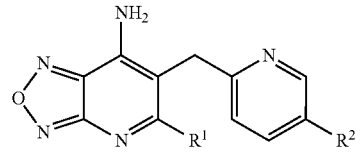

(I.6)

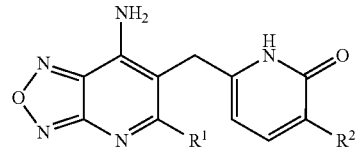

(I.7)

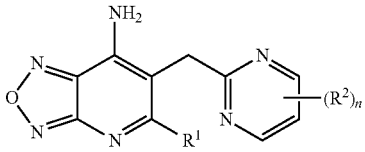

(I.8)

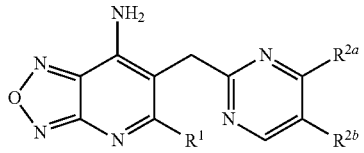

(I.9)

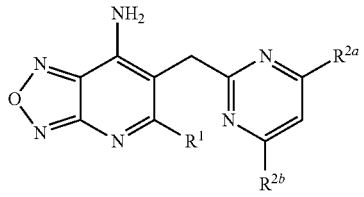

(I.10)

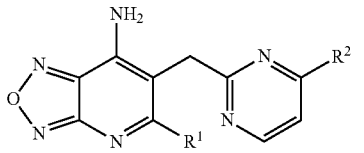

-continued (I.11)

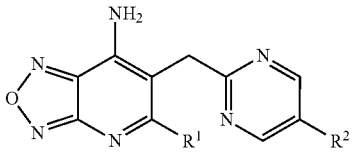

Examples of preferred subgeneric embodiments (E) according to the present invention are set forth in the following table 1, wherein each substituent group of each embodiment is defined according to the definitions set forth hereinbefore and wherein all other substituents of the formulae I, I.1, I.2, I.3, I.4, I.5, I.6, I.7, I.8, I.9, I.10 and I.11 are defined according to the definitions set forth hereinbefore. For example, the entry -G1 in the column under R— and in the line of E1 means that in embodiment E1 substituent R is selected from the definition designated R-G1. The same applies analogously to the other variables incorporated in the general formulae.

TABLE 1

| E | formula | X | $R^1$— | $R^2$— | n |
|---|---|---|---|---|---|
| E1 | I | CH or N | —G1 | —G1 | 1, 2 or 3 |
| E2 | I | CH or N | —G1 | —G2 | 1, 2 or 3 |
| E3 | I | CH or N | —G5 | —G2 | 1, 2 or 3 |
| E4 | I | CH or N | —G5 | —G3 | 1, 2 or 3 |
| E5 | I | CH or N | —G5 | —G4 | 1, 2 or 3 |
| E6 | I | CH or N | —G5 | —G5 | 1, 2 or 3 |
| E7 | I | CH or N | —G5 | —G6 | 1, 2 or 3 |
| E8 | I | CH or N | —G5 | —G1 | 1 or 2 |
| E9 | I | CH or N | —G5 | —G2 | 1 or 2 |
| E10 | I | CH or N | —G5 | —G3 | 1 or 2 |
| E11 | I | CH or N | —G5 | —G4 | 1 or 2 |
| E12 | I | CH or N | —G5 | —G5 | 1 or 2 |
| E13 | I | CH or N | —G5 | —G6 | 1, 2 or 3 |
| E14 | I | CH or N | —G5 | —G1 | 1 |
| E15 | I | CH or N | —G5 | —G2 | 1 |
| E16 | I | CH or N | —G5 | —G3 | 1 |
| E17 | I | CH or N | —G5 | —G4 | 1 |
| E18 | I | CH or N | —G5 | —G5 | 1 |
| E19 | I | CH or N | —G5 | —G6 | 1 |
| E20 | I | CH or N | —G5 | —G1 | 2 |
| E21 | I | CH or N | —G5 | —G2 | 2 |
| E22 | I | CH or N | —G5 | —G3 | 2 |
| E23 | I | CH or N | —G5 | —G4 | 2 |
| E24 | I | CH or N | —G5 | —G5 | 2 |
| E25 | I | CH or N | —G1 | —G6 | 2 |
| E26 | I | CH | —G1 | —G1 | 1, 2 or 3 |
| E27 | I | CH | —G1 | —G2 | 1, 2 or 3 |
| E28 | I | CH | —G1 | —G3 | 1, 2 or 3 |
| E29 | I | CH | —G1 | —G4 | 1, 2 or 3 |
| E30 | I | CH | —G1 | —G5 | 1, 2 or 3 |
| E31 | I | CH | —G1 | —G6 | 1, 2 or 3 |
| E32 | I | CH | —G5 | —G1 | 1 or 2 |
| E33 | I | CH | —G5 | —G2 | 1 or 2 |
| E34 | I | CH | —G5 | —G3 | 1 or 2 |
| E35 | I | CH | —G5 | —G4 | 1 or 2 |
| E36 | I | CH | —G5 | —G5 | 1 or 2 |
| E37 | I | CH | —G5 | —G6 | 1 or 2 |
| E38 | I | CH | —G5 | —G1 | 1 |
| E39 | I | CH | —G5 | —G2 | 1 |
| E40 | I | CH | —G5 | —G3 | 1 |
| E41 | I | CH | —G5 | —G4 | 1 |
| E42 | I | CH | —G5 | —G5 | 1 |
| E43 | I | CH | —G5 | —G6 | 1 |
| E44 | I | CH | —G5 | —G1 | 2 |
| E45 | I | CH | —G5 | —G2 | 2 |
| E46 | I | CH | —G5 | —G3 | 2 |
| E47 | I | CH | —G5 | —G4 | 2 |
| E48 | I | CH | —G5 | —G5 | 2 |
| E49 | I | CH | —G5 | —G6 | 2 |
| E50 | I | N | —G1 | —G1 | 1, 2 or 3 |
| E51 | I | N | —G1 | —G2 | 1, 2 or 3 |

TABLE 1-continued

| E | formula | X | $R^1$— | $R^2$— | n |
|---|---|---|---|---|---|
| E52 | I | N | —G1 | —G3 | 1, 2 or 3 |
| E53 | I | N | —G1 | —G4 | 1, 2 or 3 |
| E54 | I | N | —G1 | —G5 | 1, 2 or 3 |
| E55 | I | N | —G1 | —G6 | 1, 2 or 3 |
| E56 | I | N | —G5 | —G1 | 1 or 2 |
| E57 | I | N | —G5 | —G2 | 1 or 2 |
| E58 | I | N | —G5 | —G3 | 1 or 2 |
| E59 | I | N | —G5 | —G4 | 1 or 2 |
| E60 | I | N | —G5 | —G5 | 1 or 2 |
| E61 | I | N | —G6 | —G6 | 1 or 2 |
| E62 | I | N | —G1 | —G1 | 1 |
| E63 | I | N | —G1 | —G2 | 1 |
| E64 | I | N | —G1 | —G3 | 1 |
| E65 | I | N | —G1 | —G4 | 1 |
| E66 | I | N | —G1 | —G5 | 1 |
| E67 | I | N | —G1 | —G6 | 1 |
| E68 | I | N | —G5 | —G1 | 1 |
| E69 | I | N | —G5 | —G2 | 1 |
| E70 | I | N | —G5 | —G3 | 1 |
| E71 | I | N | —G5 | —G4 | 1 |
| E72 | I | N | —G5 | —G5 | 1 |
| E73 | I | N | —G1 | —G6 | 1 |
| E74 | I | N | —G1 | —G1 | 2 |
| E75 | I | N | —G1 | —G2 | 2 |
| E76 | I | N | —G1 | —G3 | 2 |
| E78 | I | N | —G1 | —G4 | 2 |
| E79 | I | N | —G1 | —G5 | 2 |
| E80 | I | N | —G1 | —G6 | 2 |
| E81 | I | N | —G5 | —G1 | 2 |
| E82 | I | N | —G5 | —G2 | 2 |
| E83 | I | N | —G5 | —G3 | 2 |
| E84 | I | N | —G5 | —G4 | 2 |
| ESS | I | N | —G5 | —G5 | 2 |
| E86 | I | N | —G5 | —G6 | 2 |
| E87 | I.2 | — | —G5 | —G1 | — |
| E88 | I.2 | — | —G5 | —G2 | — |
| E89 | I.2 | — | —G5 | —G3 | — |
| E90 | I.2 | — | —G5 | —G4 | — |
| E91 | I.2 | — | —G5 | —G5 | — |
| E92 | I.2 | — | —G5 | —G6 | — |
| E93 | I.3 | — | —G5 | —G1 | — |
| E94 | I.3 | — | —G5 | —G2 | — |
| E95 | I.3 | — | —G5 | —G3 | — |
| E96 | I.3 | — | —G5 | —G4 | — |
| E97 | I.3 | — | —G5 | —G5 | — |
| E98 | I.3 | — | —G5 | —G6 | — |

Another embodiment concerns those compounds of formula (I.2)

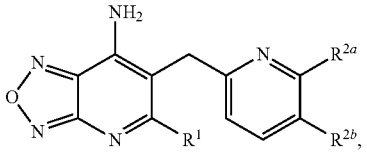

wherein $R^1$ is $CH_3$;

$R^{2a}$ and $R^{2b}$ are each independently selected from the group consisting of:

F, Cl, Br, —CN, —$CF_3$,

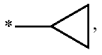

—O—$CH_3$, —O—$CHF_2$, —O—$CH_2$—$CH_2$—F, —O—$CH_2$—$CHF_2$, —O—$CH_2$—$CF_3$, —O—$CH_2$—$CH_2$—$CH_2$—F, —O—$CH_2$—$CF_2$—$CH_3$,

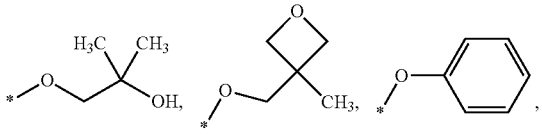
—S—$CH_3$, —$NH_2$, —NH—$CH_2$—$CH_2$—$CH_2$—F, —NH—$CH_2$—$CH_2$—$CHF_2$,
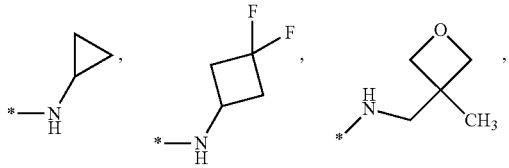
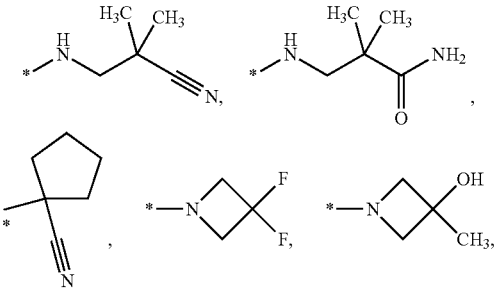
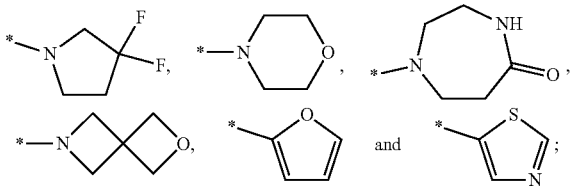
and
n is 1 or 2;
or a salt thereof, particularly a pharmaceutically acceptable salt thereof.
Preferred compounds of the invention include:
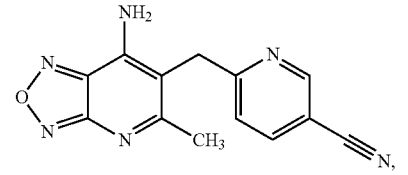
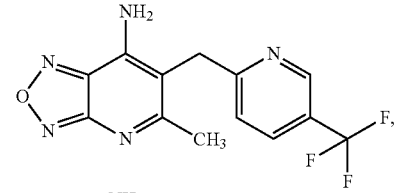
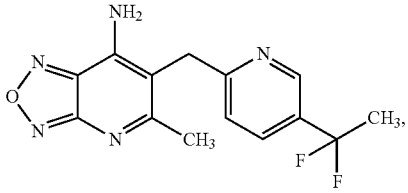
-continued
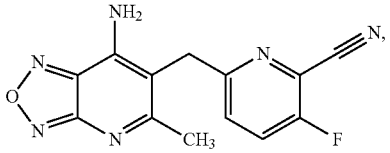
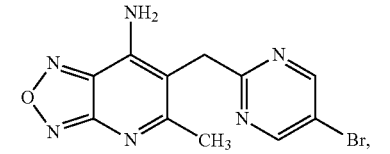
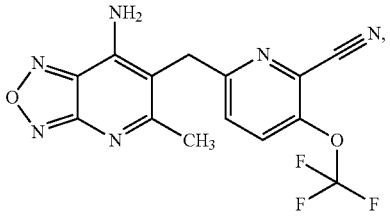
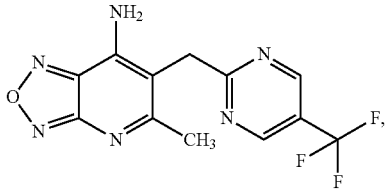
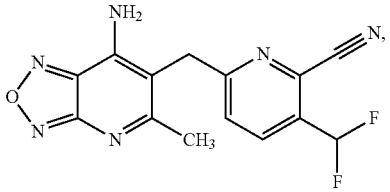
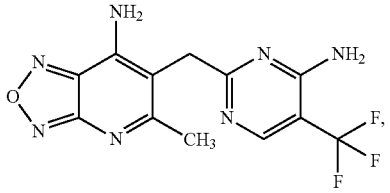
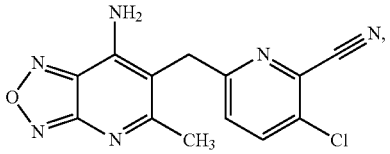
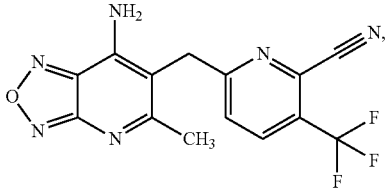
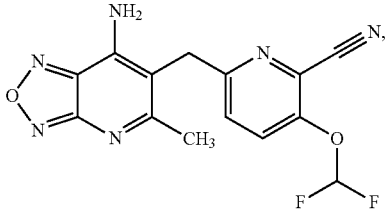

-continued

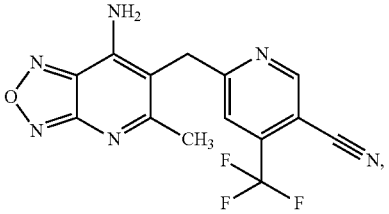

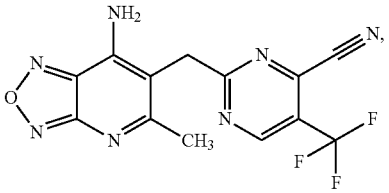

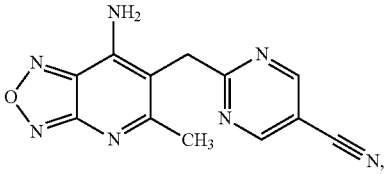

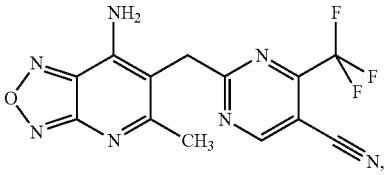

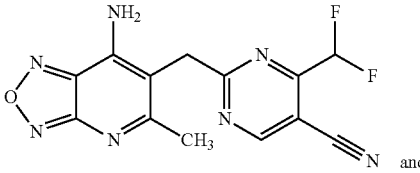

and

-continued

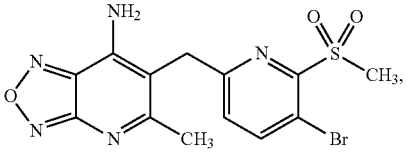

or a salt thereof, particularly a pharmaceutically acceptable salt thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis for example.

Moreover, the invention provides processes for making a compound of Formula I.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula I may be made by the method outlined in Scheme 1, 2, or 3:

Scheme 1

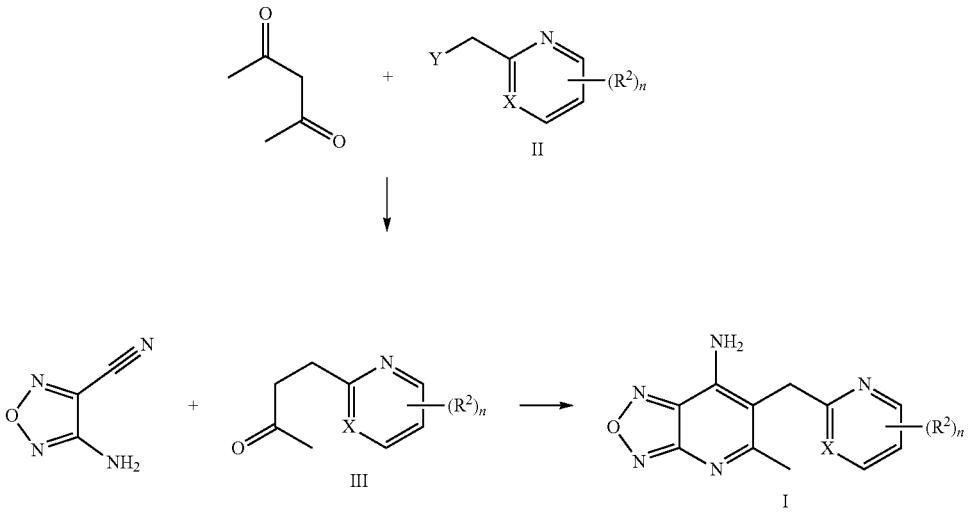

As illustrated in Scheme 1 reacting of the acetylacetone with an alkylating agent of Formula II (Y=Cl, Br, I, OMs, OTs) in the presence of a suitable base such as potassium, sodium or caesium carbonate, in a suitable solvent such as methanol or ethanol, provides a compound of Formula III.

Reacting of the compound of Formula III with the 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene, provides a compound of Formula I.

phosphorus tribromide in dichloromethane (to prepare VIb); glacial acetic acid (to prepare VIc).

Iodide of formula VII can be converted into the corresponding hetarylmagnesium chloride of formula VIII using suitable reagent such as isopropylmagnesium chloride lithium chloride complex, in a suitable solvent such as tetrahydrofuran. Reacting of hetarylmagnesium chloride of formula VIII with the compound of formula VI in the presence of copper(I)cyanide di(lithium chloride) complex, in a suitable solvent such as tetrahydrofuran, provides a compound of formula I.

Scheme 2

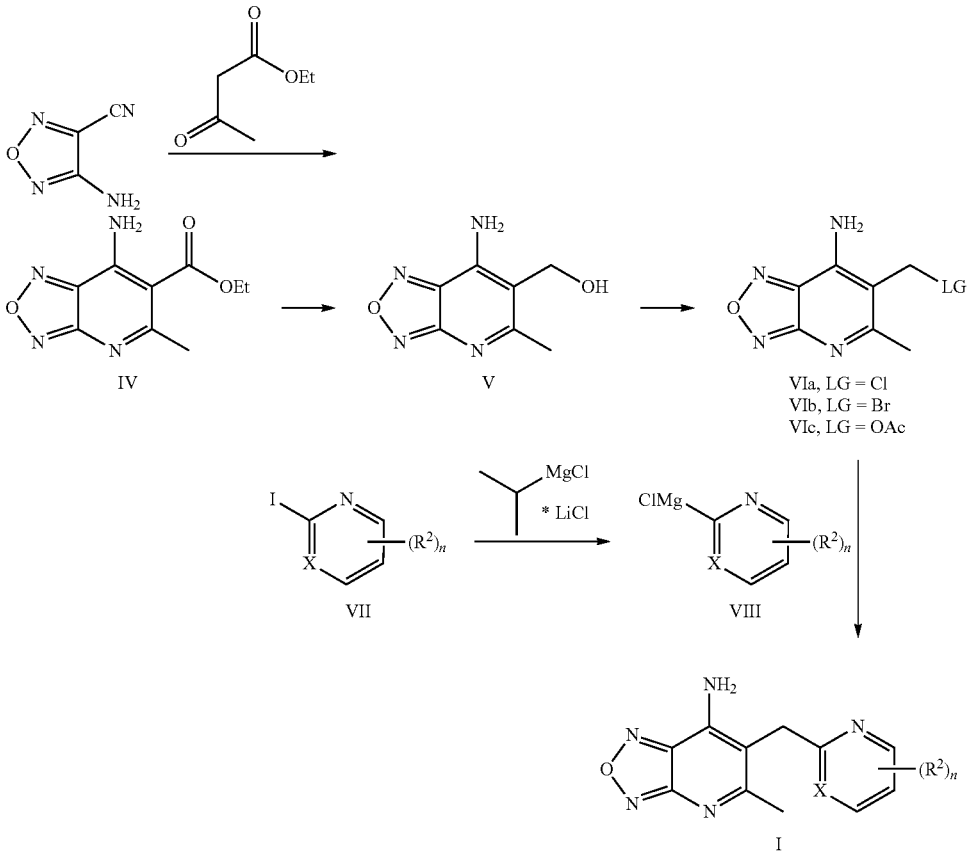

As illustrated in Scheme 2 reacting of the ethyl acetoacetate with the 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene, provides ester IV.

Reduction of the esther IV with the reducing agent such as sodium bis(2-methoxyethoxy)aluminiumhydride (Red-Al®) or lithium aluminium hydride, in a suitable solvent such as toluene/tetrahydrofuran mixture, provides alcohol V. Alcohol V can be converted into the corresponding derivatives VI using suitable reagents and solvents, such as: thionylchloride in dimethylformamide (to prepare VIa);

Scheme 3

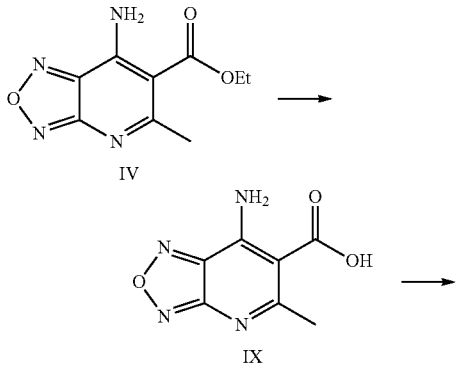

-continued

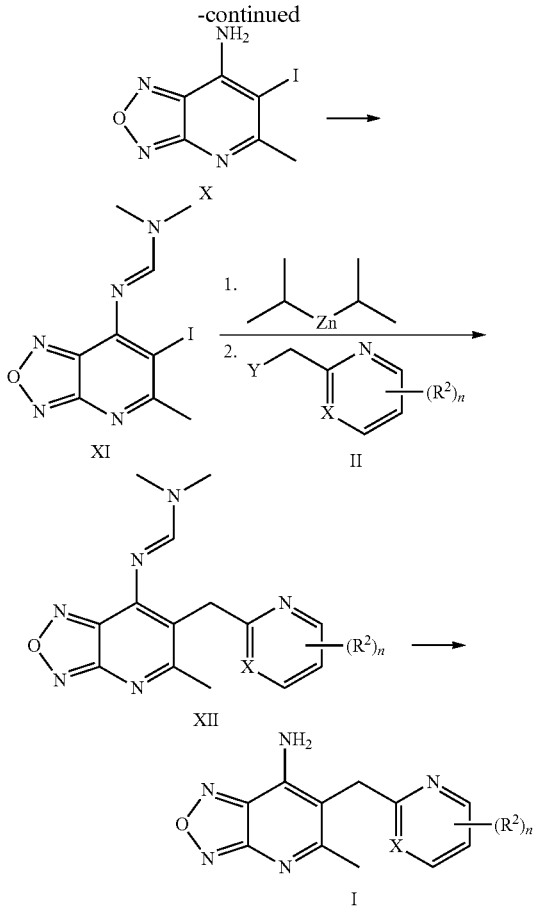

As illustrated in Scheme 3 saponification of the ester of formula IV, using a suitable reagent such as lithium, sodium or potassium hydroxide, in a suitable solvent such as tetrahydrofuran, methanol or ethanol, provides an acid of formula IX. Reacting of the acid of formula IX with N-iodosuccinimide, in the presence of a suitable base such as sodium hydrogen carbonate, in a suitable solvent such as N,N-dimethylformamide or acetonitrile, provides a compound of formula X. The protection and deprotection of functional groups is described in 'Protective Groups in Organic Synthesis', T. W. Greene and P. G. M. Wuts, Wiley-Interscience. For example, for the protection of an amine of Formula X, N,N-dimethylformamide dimethyl acetal may be used in a suitable solvent such as N,N-dimethylformamide to provide a compound of Formula XI.

Zincation of a compound of formula XI may be carried out in situ using a suitable reagent such as diisopropylzinc, in the presence of lithium acetylacetonate, in a suitable solvent such as N-methyl-2-pyrrolidone. These can be coupled in a (transition) metal catalyzed reaction with a compound of formula II (Y=Br, I) using a suitable catalyst such as [1,1'-bis(di-tert-butylphosphino)ferrocene]dichloropalladium(II), in a suitable solvent such as N-methyl-2-pyrrolidone to provide a compound of formula XII. Deprotection a compound of formula XII with concentrated aqueous hydrochloric acid, in a suitable solvent such as methanol or ethanol, provides a compound of formula I.

Further modifications of compounds of formula I by methods known in the art and illustrated in the Examples below, may be used to prepare additional compounds of the invention.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, 3rd Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the inhibition of the ghrelin O-acyl transferase (GOAT) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

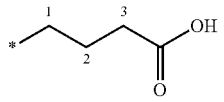

wherein the carboxy group is attached to the third carbon atom of the propyl group. The terms "1-methylpropyl-", "2,2-dimethylpropyl-" or "cyclopropylmethyl-" group represent the following groups:

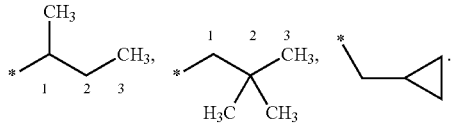

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{2-n}$alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH═$CH_2$, —CH═CH—$CH_3$, —$CH_2$—CH═$CH_2$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—$CH_3$, —$CH_2$—C≡CH.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

Determination of hGOAT Activity in HEK293 Cells after Incubation with Test Compound Principle:

HEK293 cells stably transfected with two expression vectors, one coding for preproghrelin cDNA and a second for the expression of human GOATcDNA are used as a cellular model. After feeding the cells with octanoic acid for 5 hours, acyl-ghrelin is measured in cell culture medium by an ELISA procedure.

Materials:

Cellline: Hek293 hGOAT/PPGhrl Clone #1B8Sodium octanoate, Sigma, Cat.-No. C5038

BSA: Sigma, Cat.-No. A8806

BD Poly-D-Lysin 384-well Plates, black-clear polystyrene BD Bioscience Cat.-No. 356697348-well ELISA human acylated Ghrelin Kit purchased from Bertin Pharman (detailed composition of buffers e.g. wash-puffer, ELISA buffer not known)

All further reagents used were of highest analytical grade available.

Method:

Cells are plated with a density of 5000 cells/well in 384-well poly-D-lysin plates and incubated for 1 day at 37° C., 5% CO2 in DMEM medium, 10% FCS, 1×NEAA, Puromycin (0.5 μg/ml) and G418 (1 mg/ml). Then the medium is changed to a identical medium without FCS and containing Octanoate-BSA (final concentration 100 μM each) and compound in DMSO (final DMSO concentration 0.3%). After incubation for 5 hours acylghrelin in the medium is measured by ELISA The medium sample is diluted 1:25 in Elisa buffer, A 25 ul aliquot is transferred to a 384-well ELISA plate previously washed 4 times with 100 μL wash buffer, and 25 μl tracer-solution is added. After incubation overnight (~20 h) at 4° C. temperature the plate is washed 4 times with 100 μl wash-buffer per well. Finally 50 μl Ellman's reagent is added to each well and the plate is incubated in the dark for 20 minutes. The absorbance is measured at 405 nm in an Envision multilabel reader and the amount of acylated ghrelin is calculated according to a acylated ghrelin standard curve provided in the same plate.

Each assay plate contains wells with vehicle controls (1% DMSO) for the measurement of non-inhibited transfer reaction (=100% Ctl) and wells with 10 μM ([Dap3]-Ghrelin) as controls for fully inhibited GOAT enzyme The analysis of the data is performed by calculation of the percentage of acyl-ghrelin produced in the presence of test compound compared to the amount of acyl-ghrelin produced in the vehicle control samples. An inhibitor of the GOAT enzyme will give values between 100% CTL (no inhibition) and 0% CTL (complete inhibition). IC50 values are calculated with Assay Explorer or other suited software based on curve fitting of results of 8 different compound concentrations.

Results:

| example | IC50 [nM] |
|---|---|
| 1 | 1.4 |
| 2 | 3.6 |

-continued

| example | IC50 [nM] |
|---|---|
| 3 | 0.46 |
| 4 | 1.7 |
| 5 | 0.24 |
| 6 | 0.61 |
| 7 | 0.95 |
| 8 | 0.42 |
| 9 | 0.44 |
| 10 | 13 |
| 11 | 0.13 |
| 12 | 6.5 |
| 13 | 4.4 |
| 14 | 0.67 |
| 15 | 0.038 |
| 16 | 0.28 |
| 17 | 0.22 |
| 18 | 0.32 |
| 19 | 0.047 |
| 20 | 0.17 |
| 21 | 0.03 |
| 22 | 0.066 |
| 23 | 0.082 |
| 24 | 0.12 |
| 25 | 4.4 |
| 26 | 8.8 |
| 27 | 1.7 |
| 28 | 48 |
| 29 | 16 |
| 30 | 2.7 |
| 31 | 1.8 |
| 32 | 0.44 |
| 33 | 0.3 |
| 34 | 3.2 |
| 35 | 1.8 |
| 36 | 6.9 |
| 37 | 0.2 |
| 38 | 2.6 |
| 39 | 0.18 |
| 40 | 5.2 |
| 41 | 1.2 |
| 42 | 0.073 |
| 43 | 0.37 |
| 44 | 0.17 |
| 45 | 1.2 |
| 46 | 0.22 |
| 47 | 2.4 |
| 48 | 0.18 |
| 49 | 0.15 |
| 50 | 2.5 |
| 51 | 20 |
| 52 | 0.48 |
| 53 | 2.6 |
| 54 | 0.24 |
| 55 | 3.9 |
| 56 | 0.72 |
| 57 | 0.1 |
| 58 | 2.8 |
| 59 | 0.34 |
| 60 | 0.48 |
| 61 | 0.29 |
| 62 | 0.21 |
| 63 | 0.48 |
| 64 | 0.1 |
| 65 | 0.29 |
| 66 | 0.14 |
| 67 | 0.05 |
| 68 | 0.11 |
| 69 | 0.58 |
| 70 | 0.082 |
| 71 | 0.22 |
| 72 | 1.1 |
| 73 | 0.33 |
| 74 | 2.0 |
| 75 | 2.7 |
| 76 | 14 |
| 77 | 3.8 |
| 78 | 0.36 |

-continued

| example | IC50 [nM] |
|---|---|
| 79 | 0.59 |
| 80 | 3.8 |
| 81 | 7.0 |
| 82 | 1.0 |
| 83 | 0.077 |
| 84 | 0.21 |
| 85 | 6.9 |
| 86 | 19 |
| 87 | 9 |
| 88 | 3.3 |
| 89 | 0.43 |
| 90 | 0.54 |
| 91 | 0.35 |
| 92 | 0.058 |
| 93 | 0.32 |
| 94 | 0.058 |
| 95 | 0.082 |
| 96 | 0.079 |
| 97 | 0.022 |
| 98 | 1.9 |
| 99 | 0.072 |
| 100 | 0.034 |
| 101 | 0.074 |
| 102 | 0.074 |
| 103 | 0.086 |
| 104 | 0.98 |
| 105 | 0.12 |
| 106 | 0.11 |
| 107 | 0.33 |
| 108 | 0.026 |
| 109 | 0.093 |
| 110 | 0.28 |
| 111 | 0.1 |
| 112 | 0.22 |
| 113 | 31 |
| 114 | 3.9 |
| 115 | 1.2 |
| 116 | 0.83 |
| 117 | 0.19 |
| 118 | 0.085 |
| 119 | 0.091 |
| 120 | 4.3 |
| 121 | 0.045 |
| 122 | 0.033 |
| 123 | 0.026 |
| 124 | 0.056 |
| 125 | 0.038 |
| 126 | 0.17 |
| 127 | 0.1 |
| 128 | 0.096 |
| 129 | 0.052 |
| 130 | 0.02 |
| 131 | 0.097 |
| 132 | 0.1 |
| 133 | 0.099 |
| 134 | 0.24 |
| 135 | 0.2 |
| 136 | 0.033 |
| 137 | 0.054 |
| 138 | 0.075 |
| 139 | 0.02 |
| 140 | 0.15 |
| 141 | 0.14 |
| 142 | 0.027 |
| 143 | 0.046 |
| 144 | 0.055 |
| 145 | 0.32 |
| 146 | 1.1 |
| 147 | 0.25 |
| 148 | 0.15 |
| 149 | 0.027 |
| 150 | 2.3 |
| 151 | 1.8 |
| 152 | 0.6 |
| 153 | 0.56 |
| 154 | 0.17 |

-continued

| example | IC50 [nM] |
|---|---|
| 155 | 1.2 |
| 156 | 3.5 |
| 157 | 0.26 |
| 158 | 1.7 |
| 159 | 15 |
| 160 | 3.0 |
| 161 | 0.89 |
| 162 | 4.6 |
| 163 | 2.5 |
| 164 | 7.4 |
| 165 | 14 |
| 166 | 0.38 |
| 167 | 0.82 |
| 127 | 0.1 |

In view of their ability to modulate the activity of ghrelin O-acyl transferase (GOAT), in particular an inhibitory activity, the compounds of general formula I according to the invention, including the corresponding salts thereof, are suitable for the treatment of all those diseases or conditions which may be affected or which are mediated by the inhibition of ghrelin O-acyl transferase (GOAT).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the inhibition of ghrelin O-acyl transferase (GOAT) in a patient, preferably in a human.

In yet another aspect the present invention relates to a method for treating a disease or condition mediated by the inhibition of ghrelin O-acyl transferase (GOAT) in a mammal that includes the step of administering to a patient, preferably a human, in need of such treatment a therapeutically effective amount of a compound or a pharmaceutical composition of the present invention.

Diseases and conditions mediated by inhibitors of ghrelin O-acyl transferase (GOAT) embrace obesity, including, but not limited to obesity in patients suffering from Prader-Willi-Syndrome (PWS), body weight regain, diabetes, particularly type 2 diabetes mellitus, insulin resistance, hyperphagia in PWS, Binge eating disorder, nighttime eating syndrome and alcohol and/or narcotic dependence.

Preferably, the compounds of the invention are used for treating obesity, body weight regain, type 2 diabetes, insulin resistance, and hyperphagia and obesity in PWS.

More preferably, the compounds of the invention are used for treating obesity, body weight regain, type 2 diabetes and insulin resistance.

In particular, the compounds and pharmaceutical compositions according to the invention are suitable for the treatment of obesity, including, but not limited to obesity in patients suffering from Prader-Willi-Syndrome, body weight regain, diabetes, in particular type 2 diabetes mellitus, and insulin resistance.

The compounds according to the invention are most particularly suitable for treating obesity.

The present invention further provides a GOAT inhibitor of the invention for use in a method of medical treatment.

GOAT inhibitors are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes). It will be understood that the GOAT inhibitors may thus be administered to subjects affected by conditions characterised by inadequate control of appetite or otherwise over-feeding, such as binge-eating disorder and Prader-Willi syndrome.

Thus, the invention provides a GOAT inhibitor of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides a GOAT inhibitor of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides a GOAT inhibitor of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides a GOAT inhibitor of the invention for use in a method of lowering circulating LDL levels and/or increasing HDL/LDL ratio.

Effects of GOAT inhibitors on these conditions may be mediated in whole or in part via an effect on body weight, or may be independent thereof.

The invention further provides use of a GOAT inhibitor of the invention in the manufacture of a medicament for treating, inhibiting or reducing weight gain, promoting weight loss and/or reducing excess body weight.

The invention also provides use of a GOAT inhibitor of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides use of a GOAT inhibitor of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides use of a GOAT inhibitor of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of a GOAT inhibitor of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of a GOAT inhibitor of the invention to the subject.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke in a subject, comprising administering a therapeutically effective amount of a GOAT inhibitor of the invention to the subject.

The invention further provides a method of lowering circulating LDL levels and/or increasing HDL/LDL ratio in a subject, comprising administering a therapeutically effective amount of a GOAT inhibitor of the invention to the subject.

The invention further provides the use of a GOAT inhibitor as described above in a method of cosmetic (i.e. non-therapeutic) weight loss. It will be understood that references to therapeutic uses of GOAT inhibitors and methods comprising administration of GOAT inhibitors may equally be taken to encompass uses and administration of such compositions.

Further aspects and embodiments of the present invention will become apparent from the disclosure below.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

A compound of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a compound of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™ Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™).

Moreover, a compound of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), Orlistat™, Sibutramine™, phentermine, a melanin concentrating hormone receptor 1 antagonist, CCK, amylin, pramlintide and leptin, as well as analogues thereof.

A compound of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A compound of the invention may still further be used in combination with an anti-dyslipidemia agent of known type, including, but not limited to, a statin, a fibrate, a niacin, a PSCK9 (Proprotein convertase subtilisin/kexin type 9) inhibitor, and a cholesterol absorption inhibitor.

A compound of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™ Pantoprazole™, Rabeprazole™, Zolpidem™, Alpidem™, Saripidem™ or Necopidem™.

In addition, with regard to anti-inflammatory treatment, a compound of the invention may be beneficial if administered in combination with an anti-inflammatory agent of known type, including, but not limited to:

steroids and corticosteroids, such as beclomethasone, methylprednisolone, betamethasone, prednisone, dexamethasone, and hydrocortisone;

non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1 a or interferon beta-1 b);

and certain other compounds, such as 5-aminosalicylic acid and prodrugs and pharmaceutically acceptable salts thereof.

Metformin has also been demonstrated to have anti-inflammatory properties (see, e.g., Haffner et al., Diabetes 54: 1566-1572 (2005)) and as such may also be useful in combination with compounds of the invention.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the inhibition of ghrelin O-acyl transferase (GOAT), in particular diseases or conditions as described hereinbefore and hereinafter.

In yet another aspect the present invention relates a method for treating a disease or condition mediated by the inhibition of ghrelin O-acyl transferase (GOAT) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The following examples serve to further explain the invention without restricting it.

The hereinafter described compounds have been characterized through their characteristic mass after ionisation in a mass-spectrometer and/or their retention time on an analytical HPLC.

HPLC Methods:

Method 1:
Column: Waters XBridge C18, 3 × 30 mm, 2.5 μm
Detection: Agilent 1200 with DA- and MS-Detector
Eluent A: Water (0.1% $NH_3$); Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 2:
Column: Waters SunFire, 3 × 30 mm, 2.5 μm
Detection: Agilent 1200 with DA- and MS-Detector
Eluent A: Water (0.1% Trifluoroacetic acid); Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 3:
Column: Waters SunFire C18, 3 × 30 mm, 2.5 μm
Detection: Agilent 1200 with DA- and MS-Detector
Eluent A: Water (0.1% Formic acid); Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 4:
Column: Waters XBridge C18, 3 × 30 mm, 2.5 μm
Detection: Agilent 1200 with DA- and MS-Detector
Eluent A: Water (0.1% Formic acid); Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 5:
Column: Waters XBridge C18, 3 × 30 mm, 2.5 μm
Detection: Agilent 1100 with DAD, CTC
Autosampler and Waters MS-Detector
Eluent A: Water (0.1% $NH_4OH$); Eluent B: Acetonitrile

| Gradient: | Time (min.) | % Eluent B | Flow [mL/min] | Temp [° C.] |
|---|---|---|---|---|
| | 0.00 | 2 | 2.0 | 60 |
| | 1.20 | 100 | 2.0 | 60 |
| | 1.40 | 100 | 2.0 | 60 |

Method 10:
Column: Waters XBridge C18, 3.0 × 30 mm, 2.5 μm
Detection: Waters Acquity with 3100 MS
Eluent A: Water (0.1% $NH_4OH$); Eluent B: Acetonitrile

| Gradient: | Time (min.) | % Eluent B | Flow [mL/min] | Temp [° C.] |
|---|---|---|---|---|
| | 0.00 | 5 | 1.5 | 60 |
| | 1.30 | 99.0 | 1.5 | 60 |
| | 1.50 | 99.0 | 1.5 | 60 |

Method 12:
XBridge C18_3.0 × 30 mm, 2.5 μm
Detection: Agilent 1200 with DA- and MS-Detector
Eluent A: Water (0.1% TFA); Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 0 | 2.2 | 60 |
| | 1.25 | 0 | 2.2 | 60 |
| | 1.40 | 0 | 2.2 | 60 |

Method 13:
Sunfire C18_3.0 × 30 mm, 2.5 μm
Detection: Waters Acquity, QDa Detector
Eluent A: Water (0.1% TFA); Eluent B: Acetonitrile (0.08% TFA)

| Gradient: | Time (min.) | % Eluent B | Flow [mL/min] | Temp [° C.] |
|---|---|---|---|---|
| | 0.00 | 5 | 1.5 | 40 |
| | 1.30 | 100 | 1.5 | 40 |
| | 1.50 | 100 | 1.5 | 40 |
| | 1.60 | 5 | 1.5 | 40 |

Preparation of the Starting Compounds:

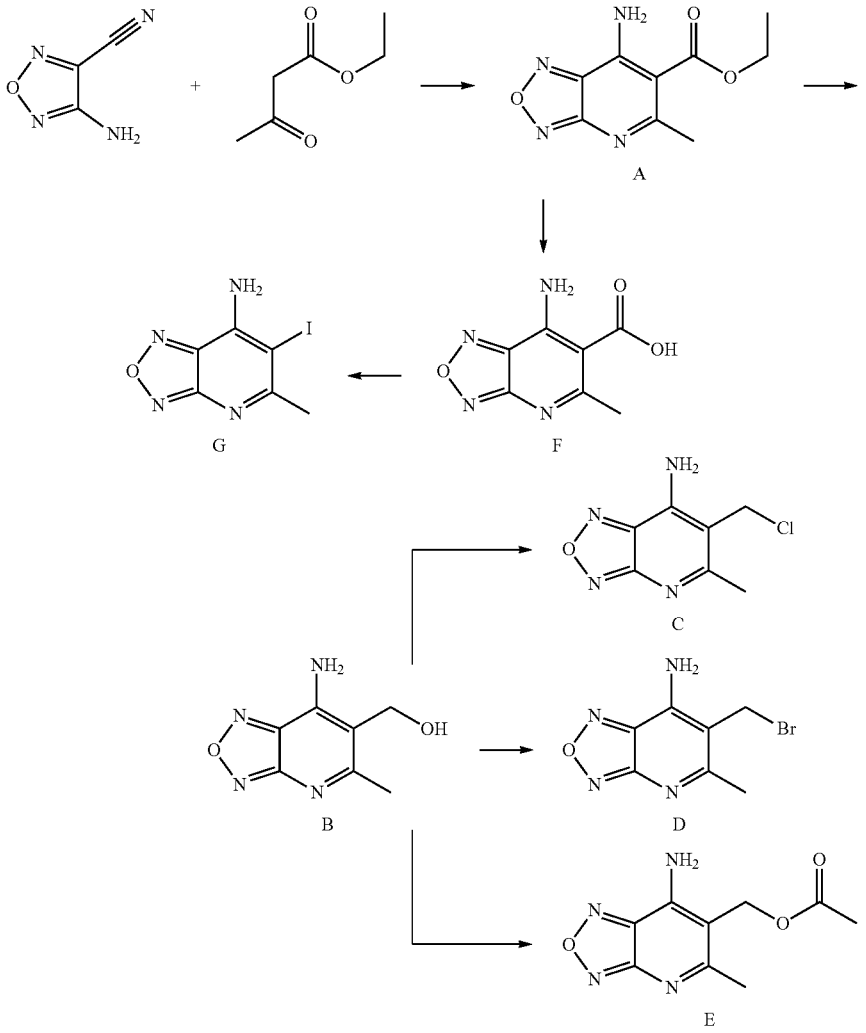

A 7-Amino-5-methyl-[1,2,5]oxadiazolo[3,4-b]pyridin-6-carboxylic Acid Ethyl Ester

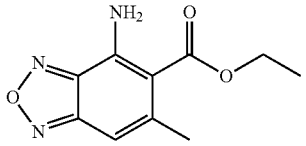

4-Amino-1,2,5-oxadiazole-3-carbonitrile (prepared according to Chemistry of Heterocyclic Compounds (New York, N.Y., United States), 1994, vol. 30, #5 p. 608-611) (1.00 g, 9.08 mmol) and ethyl acetoacetate (1.15 mL, 9.08 mmol) are dissolved in 10 mL of toluene. Tin(IV)chloride (2.13 mL, 18.2 mmol) is added and the mixture is stirred at reflux for 30 minutes. The mixture is concentrated under reduced pressure and the residue is diluted with $NaHCO_3$ (half saturated aqueous solution) and the aqueous phase is extracted with dichloromethane. The combined organic layers are dried and concentrated under reduced pressure.

Yield: 2.47 g (98% of theory)
Mass spectrometry ($ESI^+$): m/z=223 [M+H]+
HPLC (Method 1): Retention time=0.85 min.

B 7-Amino-5-methyl-[1,2,5]oxadiazolo[3,4-b]pyridin-6-ylmethanol

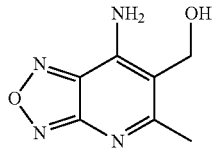

The reaction is carried out under an argon atmosphere. A mixture of 7-amino-5-methyl-[1,2,5]oxadiazolo[3,4-b]pyridin-6-carboxylic acid ethyl ester A (1.00 g, 3.60 mmol) in 10 mL toluene and 5 mL tetrahydrofuran is cooled to −78° C. Sodium bis(2-methoxy ethoxy)aluminium hydride (65% in toluene; 1.13 mL, 3.78 mmol) is added. The mixture is allowed to warm up to room temperature. After stirring over night at room temperature additional sodium bis(2-methoxy ethoxy)aluminium hydride (65% in toluene, 1.13 mL, 3.78 mmol) is added. After stirring for further 1.5 hours the mixture is diluted with sodium-potassium-tartrate (saturated aqueous solution) and extracted twice with tetrahydrofuran/ethyl acetate. The combined organic layers are dried and concentrated under reduced pressure. The residue is purified by RP-HPLC (modifier: trifluoroacetic acid).

Yield: 530 mg (81% of theory)

Mass spectrometry (ESI$^+$): m/z=181 $[M+H]^+$

HPLC (Method 3): Retention time=0.24 min.

C 6-Chloromethyl-5-methyl-[1,2,5]oxadiazolo[3,4-b]pyridin-7-ylamine

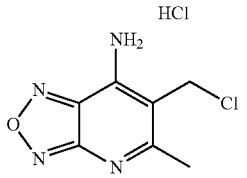

7-Amino-5-methyl-[1,2,5]oxadiazolo[3,4-b]pyridin-6-ylmethanol B (30.0 mg, 0.17 mmol) is taken up in 0.2 mL N,N-dimethylformamide. Thionylchloride (24 μL, 0.33 mmol) is slowly added dropwise. The mixture is stirred for 20 minutes at room temperature and then concentrated under reduced pressure.

Yield: 33.0 mg (100% of theory)

Mass spectrometry (ESI$^+$): m/z=195 $[M+H]^+$, corresponding to methylether analog upon adding methanol for HPLC analysis HPLC (Method 2): Retention time=0.28 min.

D 6-(bromomethyl)-5-methyl-[1,2,5]oxadiazolo[3,4-b]pyridin-7-amine Hydrobromide

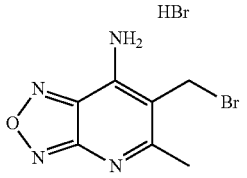

7-amino-5-methyl-[1,2,5]oxadiazolo[3,4-b]pyridin-6-ylmethanol B (541 mg, 3.00 mmol) is dissolved in 30 mL of dichloromethane. Phosphorus tribromide (0.10 mL, 1.05 mmol) is added dropwise and the mixture is stirred at room temperature for 4 days. The solid is filtered and washed with dichloromethane.

Yield: 850 mg (88% of theory)

e 7-amino-5-methyl-[1,2,5]oxadiazolo[3,4-b]pyridin-6-ylmethyl Acetate

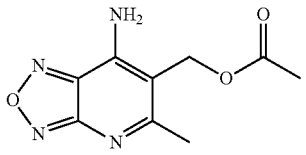

7-amino-5-methyl-[1,2,5]oxadiazolo[3,4-b]pyridin-6-ylmethanol B (25.0 g, 139 mmol) is suspended in 160 mL concentrated acetic acid and the mixture is stirred at 100° C. for 1.5 hours. Tert-butyl-methyl-ether is added at RT and the mixture is stirred for 1 hour. The solid is filtered and washed with tert-butyl-methyl-ether. The solid is dried at 50° C. under vacuum.

Yield: 23 g (75% of theory)

Mass spectrometry (ESI$^+$): m/z=223 $[M+H]^+$

HPLC (Method 3): Retention time=0.68 min.

F 7-Amino-5-methyl-[1,2,5]oxadiazolo[3,4-b]pyridine-6-carboxylic Acid

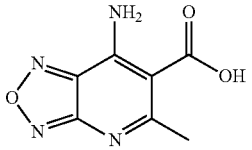

7-Amino-5-methyl-[1,2,5]oxadiazolo[3,4-b]pyridin-6-carboxylic acid ethyl ester A (5.00 g, 22.5 mmol) is dissolved in 45 mL tetrahydrofuran and sodium hydroxide (1 M aqueous solution) (34 mL, 34 mmol) is added. The mixture is stirred for 18 hours at room temperature. Hydrochloric acid (4 M aqueous solution) (8.4 ml, 34 mmol) is slowly added and the mixture is concentrated under reduced pressure to afford a solid residue. This solid material is filtered, rinsed with water, and dried under reduced pressure.

Yield: 3.40 g (78% of theory)

Mass spectrometry (ESI$^+$): m/z=195 $[M+H]^+$

HPLC (Method 12): Retention time=0.20 min.

G 6-Iodo-5-methyl-[1,2,5]oxadiazolo[3,4-b]pyridin-7-ylamine

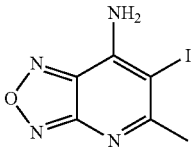

7-Amino-5-methyl-[1,2,5]oxadiazolo[3,4-b]pyridine-6-carboxylic acid F (3.40 g, 17.5 mmol) is dissolved in 40 ml N,N-dimethylformamide, sodium bicarbonate (1.77 g, 21.0 mmol) and N-iodosuccinimide (4.73 g, 21.0 mmol) are then sequentially added. The mixture is stirred for 18 hours at room temperature and then concentrated under reduced pressure. The residue is diluted with water and stirred for 10 minutes. The mixture is filtered to collect the solid material that is washed with water and dried under reduced pressure.

Yield: 4.65 g (96% of theory)

Mass spectrometry (ESI$^+$): m/z=277 $[M+H]^+$

HPLC (Method 12): Retention time=0.67 min.

2.1 2-Iodo-5-trifluoromethyl-isonicotonitrile

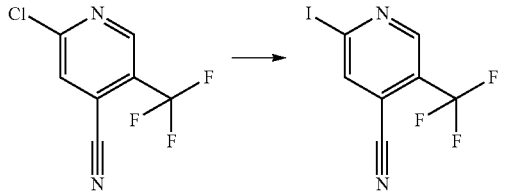

2.1

2-Chloro-5-trifluoromethyl-isonicotonitrile (3.30 g, 16.0 mmol) is dissolved in 20 ml dichloromethane and cooled to 0° C. Hydriodic acid (57% in water, 1.58 mL, 12.0 mmol) is added and the mixture is stirred for 48 hours. The mixture is washed with half saturated aqueous potassium carbonate and sodium thiosulfate solutions and then washed with concentrated aqueous sodium chloride solution. The organic layer is dried, concentrated under reduced pressure and purified by RP-HPLC.

Yield: 2.82 g (28% of theory)

Mass spectrometry ($ESI^+$): m/z=299 $[M+H]^+$

HPLC (Method 3): Retention time=1.01 min.

4.1 6-Iodo-nicotinonitrile

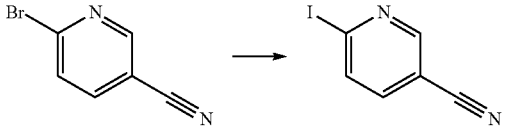

2-Bromo-5-cyanopyridine (purchased from Apollo-Inter) (7.50 g, 41.0 mmol) is dissolved in 75 mL dioxane. Copper (I)iodide (1.56 g, 8.20 mmol) and sodium iodide (15.4 g, 103 mmol) are added and the mixture is stirred for 10 minutes. N,N'-Dimethylethylendiamine (1.75 mL, 16.4 mmol) is added and the mixture is stirred at 130° C. for 18 hours. The mixture is extracted with half saturated solution of sodium bicarbonate. The aqueous phase is extracted with ethyl acetate. The organic phase is dried and concentrated under reduced pressure. The residue is purified by silica gel chromatography (eluent: cyclohexane/ethyl acetate 110/0→70/30).

Yield: 6.60 g (70% of theory)

Mass spectrometry ($ESI^-$): m/z=231 $[M+H]^+$

HPLC (Method 3): Retention time=0.62 min.

6.1 2-Iodo-5-trifluoromethyl-pyridine

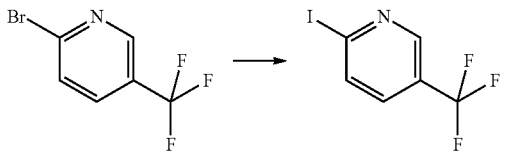

Analogously to example 4.1 obtained by starting from 2-bromo-5-trifluoromethyl-pyridine (purchased from Aldrich).

Yield: 93% of theory

Mass spectrometry ($ESI^+$): m/z=274 $[M+H]^+$

HPLC (Method 3): Retention time=1.03 min.

9.1 5-Difluoromethyl-2-iodo-pyridine

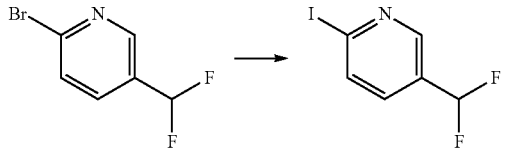

Analogously to example 4.1 obtained by starting from 2-bromo-5-difluoromethyl-pyridine (purchased from Manchester).

Yield: 97% of theory

Mass spectrometry ($ESI^-$): m/z=256 $[M+H]^+$

HPLC (Method 3): Retention time=0.91 min.

10.2 (6-Iodo-pyridin-3-yl)-acetic Acid Methyl Ester

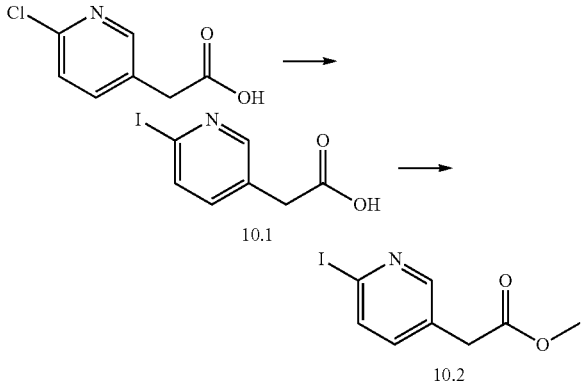

10.1

10.2

Prepared as described in WO2008/71646 page 91

11.1 5-(1,1-Difluoro-ethyl)-2-iodo-pyridine

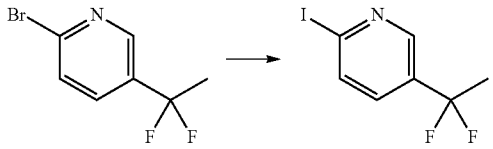

Analogously to example 4.1, obtained by starting from 2-bromo-5-(1,1-difluoro-ethyl)-pyridine (purchased from Manchester).

Yield: 95% of theory

Mass spectrometry ($ESI^-$): m/z=270 $[M+H]^+$

HPLC (Method 3): Retention time=1.00 min.

12.1 5-Fluoro-2-iodo-pyridine

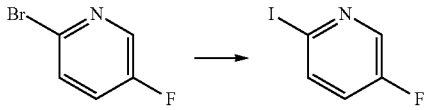

Analogously to example 4.1 obtained by starting from 2-bromo-5-fluoro-pyridine (purchased from Aldrich).

Yield: 83% of theory

HPLC (Method 3): Retention time=0.86 min.

13.1 2-Fluoro-6-iodo-pyridine

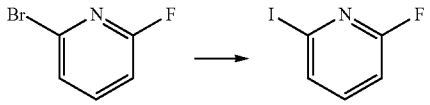

Analogously to example 4.1 obtained by starting from 2-bromo-6-fluoro-pyridine (purchased from ABCR).

Yield: 85% of theory

HPLC (Method 3): Retention time=0.90 min.

14.2 5-Difluoromethoxy-2-iodo-pyridine

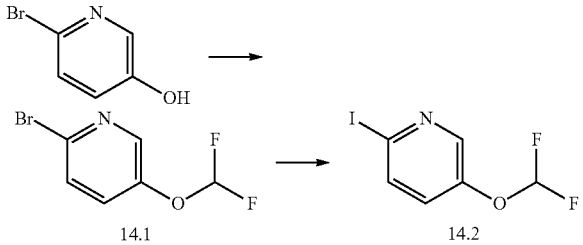

14.1 14.2

14.1 2-Bromo-5-difluoromethoxy-pyridine

6-Bromo-pyridin-3-ol (purchased from ABCR) (0.50 g, 2.87 mmol), sodium chloro-difluoro-acetate (0.88 g, 5.75 mmol) and potassium carbonate (0.50 g, 3.59 mmol) are dissolved in 5 ml N,N-Dimethylformamide and stirred at 80° C. for 18 hours. Water is added and the mixture is extracted with diethyl ether twice. The organic phase is dried and concentrated under reduced pressure. The mixture is purified by silica gel chromatography (eluent: cyclohexane/ethyl acetate 5%→15%).

Yield: 0.23 g (35% of theory)

Mass spectrometry (ESI$^-$): m/z=224, 226 $[M+H]^+$

HPLC (Method 3): Retention time=0.93 min.

14.2 5-Difluoromethoxy-2-iodo-pyridine

Analogously to example 4.1 obtained by starting from 2-bromo-5-difluoromethoxy-pyridine 14.1.

Yield: 99% of theory

Mass spectrometry (ESI$^-$): m/z=272 $[M+H]^+$

HPLC (Method 2): Retention time=0.99 min.

15.2 2-Bromo-3-difluoromethoxy-6-iodo-pyridine

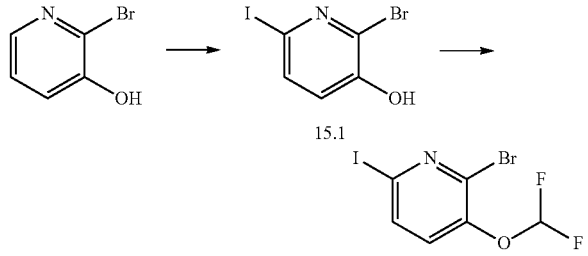

15.1 15.2

15.1 2-Bromo-6-iodo-pyridin-3-ol

2-Bromo-pyridin-3-ol (purchased from Aldrich) (1.00 g, 5.75 mmol) is dissolved in 13 mL water, potassium carbonate (1.51 g, 10.9 mmol) is added and the mixture is stirred until it becomes homogeneous. Solid iodine (1.58 g, 6.21 mmol) is added and the mixture is stirred at 100° C. for 18 hours. The mixture is cooled to room temperature, acidified with hydrochloric acid (1N aqueous solution) and extracted with ethyl acetate. The organic fractions are dried with sodium sulfate and concentrated.

Yield: 82% of theory

Mass spectrometry (ESI$^-$): m/z=299, 301 $[M+H]^+$

HPLC (Method 3): Retention time=0.85 min.

15.2 2-Bromo-3-difluoromethoxy-6-iodo-pyridine

Analogously to intermediate 14.1 obtained by starting from 2-bromo-6-iodo-pyridin-3-ol 15.1 and sodium chlorodifluoro-acetate. Caesium carbonate is used instead of potassium carbonate.

Yield: 98% of theory

Mass spectrometry (ESI$^-$): m/z=349, 351 $[M+H]^+$

HPLC (Method 3): Retention time=1.04 min.

16.1 2-Iodo-6-methylsulfanyl-pyridine

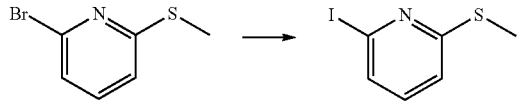

Analogously to example 4.1, obtained by starting from 2-bromo-6-(methylthio)pyridine (purchased from Activate). The reaction mixture is stirred at 110° C. for 20 hours. Ammonia (32% solution in water, 40 mL) is then added and the reaction is poured into water and extracted with dichloromethane, dried with sodium sulfate and concentrated under reduced pressure.

Yield: 92% of theory

HPLC (Method 3): Retention time=1.08 min.

19.2 3-Bromo-2-chloro-6-iodo-pyridine

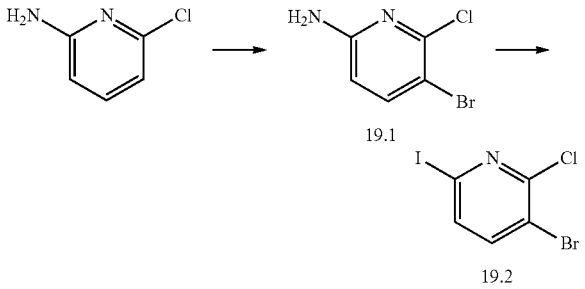

19.1 5-Bromo-6-chloro-pyridin-2-ylamine 6-chloro-pyridin-2-ylamine (purchased from Aldrich) (1.50 g, 11.7 mmol) is dissolved in 15 ml N,N-Dimethylformamide and cooled to 5° C. 1-bromo-pyrrolidine-2,5-dione (2.28 g, 12.8 mmol) is added and the mixture is slowly warmed to room temperature. The mixture is poured onto ice water and the precipitate is collected by filtration and dried under vacuum.

Yield: 91% of theory

Mass spectrometry (ESI⁻): m/z=207, 209 $[M+H]^+$

HPLC (Method 4): Retention time=0.87 min.

19.2 3-Bromo-2-chloro-6-iodo-pyridine

5-Bromo-6-chloro-pyridin-2-ylamine 19.1 (2.00 g, 9.64 mmol) is dissolved in 20 mL tetrahydrofuran, copper(I) iodide (2.75 g, 14.5 mmol) is added and diiodomethane (6.2 ml, 77.1 mmol) and tert-butyl nitrite (4.59 ml, 38.6 mmol) are added. The mixture is stirred under reflux for 1 hour, and then it is cooled to room temperature and concentrated. The residue is dissolved in ethyl acetate and extracted with 10% aqueous solution of sodium thiosulfate and saturated aqueous solution of sodium bicarbonate. The organic phase is washed with brine, dried and concentrated under reduced pressure. The mixture is purified by silica gel chromatography (eluent: cyclohexane/ethyl acetate 0%→5%).

Yield: 1.80 g (58% of theory)

Mass spectrometry (ESI⁻): m/z=318 $[M+H]^+$

HPLC (Method 4): Retention time=1.00 min.

20.1 4-Chloro-2-iodo-5-trifluoromethyl-pyridine

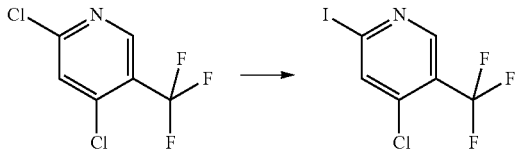

2,4-dichloro-5-trifluoromethyl-pyridine (purchased from Manchester) (1.00 g, 4.63 mmol) is dissolved in 6.0 mL acetonitrile. Sodium iodide (694 mg, 4.63 mmol) and acetyl chloride (329 μL, 4.63 mmol) are added and the mixture is stirred at room temperature for 3.5 hours. The mixture is diluted with ethyl acetate, washed with half saturated solutions of sodium bicarbonate and sodium thiosulfate, dried and concentrated under reduced pressure. The residue is purified by preparative RP-HPLC (modifier: trifluoroacetic acid).

Yield: 220 mg (15% of theory)

HPLC (Method 4): Retention time=1.02 min.

21.2 2,3-Dibromo-6-iodo-pyridine

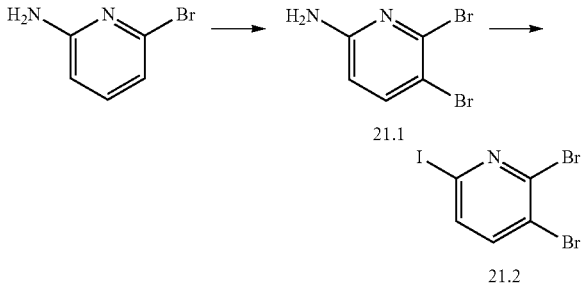

5,6-Dibromo-pyridin-2-ylamine is prepared as described in WO2005/100353 page 21

21.2 2,3-Dibromo-6-iodo-pyridine

Analogously to example 19.2, obtained by starting from 5,6-dibromo-pyridin-2-ylamine and tert-butyl nitrite.

Yield: 80% of theory 22.2 3-Bromo-2-fluoro-6-iodo-pyridine

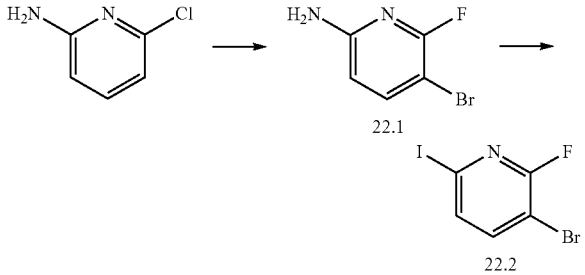

22.1 5-Bromo-6-fluoro-pyridin-2-ylamine

Analogously to example 19.1, obtained by starting from 6-fluoro-pyridin-2-ylamine (purchased from Activate) and 1-bromo-pyrrolidine-2,5-dione.

Yield: 60% of theory

Mass spectrometry (ESI⁻): m/z=191, 193 $[M+H]^+$

HPLC (Method 4): Retention time=0.75 min.

22.2 3-Bromo-2-fluoro-6-iodo-pyridine

Analogously to example 19.2 obtained by starting from 5-bromo-6-fluoro-pyridin-2-ylamine 22.1 and tert-butyl nitrite.

Yield: 61% of theory

Mass spectrometry (ESI⁻): m/z=301, 303 $[M+H]^+$

HPLC (Method 4): Retention time=0.96 min.

23.3 3-Bromo-2-difluoromethoxy-6-iodo-pyridine

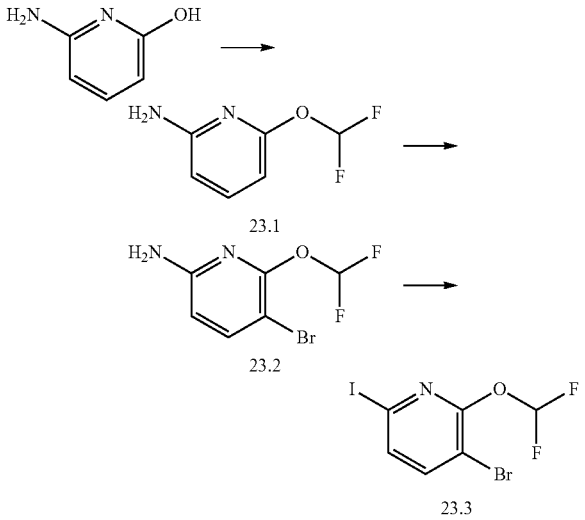

23.1

23.2

23.3

23.1 6-Difluoromethoxy-pyridin-2-ylamine

Analogously to intermediate 14.1 obtained by starting from 6-amino-pyridin-2-ol (purchased from Acros) and sodium chloro-difluoro-acetate. Stirred for 18 hours at 100° C., extracted with ethyl acetate and a half saturated aqueous solution of sodium bicarbonate instead of diethyl ether. The organic phase is washed with brine, dried and concentrated.

Yield: 64% of theory

Mass spectrometry (ESI⁻): m/z=161 $[M+H]^+$

HPLC (Method 4): Retention time=0.71 min.

23.2 5-Bromo-6-difluoromethoxy-pyridin-2-ylamine

Analogously to example 19.1, obtained by starting from 6-difluoromethoxy-pyridin-2-ylamine 23.1 and 1-bromopyrrolidine-2,5-dione.

Yield: 94% of theory

Mass spectrometry (ESI⁻): m/z=240, 242 $[M+H]^+$

HPLC (Method 4): Retention time=0.89 min.

23.3 3-Bromo-2-difluoromethoxy-6-iodo-pyridine

Analogously to example 19.2 obtained by starting from 5-bromo-6-difluoromethoxy-pyridin-2-ylamine 23.2 and tert-butyl nitrite.

Yield: 34% of theory

HPLC (Method 4): Retention time=1.04 min.

24.3 2-Chloro-6-iodo-nicotinonitrile

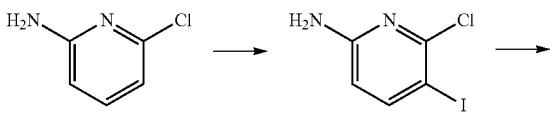

24.1

-continued

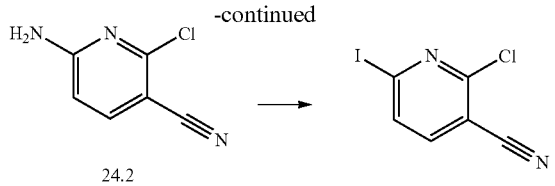

24.2

24.3

24.1 6-Chloro-5-iodo-pyridin-2-ylamine

Analogously to example 19.1, obtained by starting from 6-chloro-pyridin-2-ylamin (purchased from Aldrich), add N-iodosuccinimide at room temperature (temperature rise until 80° C.) and stirred for 15 minutes. The mixture is poured onto ice water and the precipitate is filtered and dried under vacuum.

Yield: 94% of theory

Mass spectrometry (ESI⁻): m/z=255 $[M+H]^+$

HPLC (Method 12): Retention time=0.82 min.

24.2 6-Amino-2-chloro-nicotinonitrile

6-Chloro-5-iodo-pyridin-2-ylamine 24.1 (4.00 g, 15.7 mmol) is dissolved in 15 mL N,N-dimethylformamide, zinc cyanide (0.997 g, 8.50 mmol) is added and the mixture is vigorously stirred while purging the mixture with an argon stream for 5 min. (Tris(dibenzylideneacetone)-dipalladium (0) (0.642 g, 0.701 mmol) and 1,1'-bis(diphenylphosphino) ferrocene (0.784 g, 1.42 mmol) are added and stirred for 10 minutes at 120° C. The mixture is extracted with ethyl acetate and a half saturated aqueous solution of sodium bicarbonate. The organic phase is filtered over silica gel and concentrated. The mixture is purified by silica gel chromatography (eluent: cyclohexane/ethyl acetate 100/0→50/50).

Yield: 1.60 g (66% of theory)

Mass spectrometry (ESI⁺): m/z=154 $[M+H]^+$

HPLC (Method 1): Retention time=0.60 min 24.3 2-Chloro-6-iodo-nicotinonitrile

Analogously to example 19.2 obtained by starting from 6-Amino-2-chloro-nicotinonitrile 24.2 and tert-butyl nitrite.

Yield: 60% of theory

HPLC (Method 4): Retention time=0.87 min.

25.3 3-Fluoro-6-iodo-pyridine-2-carbonitrile

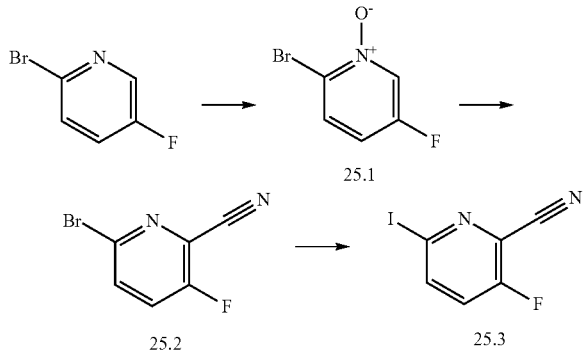

25.1

25.2

25.3

25.1 2-Bromo-5-fluoro-pyridine 1-oxide 2-bromo-5-fluoro-pyridine (purchased from Activate) (8.60 g, 48.9 mmol) is dissolved in 75 mL dichloromethane, then cooled to 0° C. and trifluoroacetic anhydride (20.4 ml, 147 mmol) is added. Hydrogen peroxide (30% aqueous solution, 5.9 ml, 58.6 mmol) is added dropwise and the reaction stirred for 18 hours at room temperature. The mixture is poured carefully on a diluted saturated aqueous solution of sodium bicarbonate. The organic phase is separated, dried and concentrated under reduced pressure.

Yield: 7.18 g (76% of theory)

Mass spectrometry ($ESI^+$): m/z=192, 194 $[M+H]^+$

HPLC (Method 12): Retention time=0.19 min 25.2 6-Bromo-3-fluoro-pyridine-2-carbonitrile 2-Bromo-5-fluoro-pyridine 1-oxide 25.1 (7.18 g, 37.4 mmol) and dimethyl sulfate (3.9 ml, 41.1 mmol) are stirred at room temperature for 72 h. The residue is dissolved in 35 mL water and cooled to 0° C. To this reaction mixture is added a prepared solution of sodium cyanide (7.45 g, 146 mmol) in 35 ml water and the mixture is stirred for 20 minutes at 0° C. The solid is collected by filtration and dried under reduced pressure.

Yield: 6.38 g (85% of theory)

Mass spectrometry ($ESI^+$): m/z=200, 202 $[M+H]^+$

HPLC (Method 12): Retention time=0.79 min 25.3 3-Fluoro-6-iodo-pyridine-2-carbonitrile Analogously to example 4.1 obtained by starting from 6-Bromo-3-fluoro-pyridine-2-carbonitrile 25.2.

Yield: 74% of theory

Mass spectrometry ($ESI^-$): m/z=248 $[M+H]^+$

HPLC (Method 12): Retention time=0.83 min.

26.1 2-Iodo-4-trifluoromethyl-pyridine

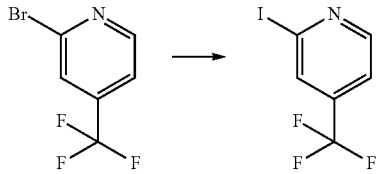

Analogously to intermediate 20.1 obtained by starting from 2-bromo-4-trifluoromethyl-pyridine (purchased from Activate), acetyl chloride and sodium iodide.

Yield: 99% of theory 27.1 5-Bromo-2-iodo-isonicotinonitrile

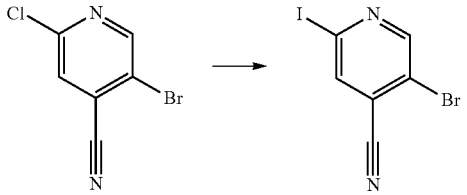

Analogously to intermediate 20.1 obtained by starting from 5-bromo-2-chloro-isonicotinonitrile (purchased from Apollo), acetyl chloride and sodium iodide.

Yield: 86% of theory

HPLC (Method 3): Retention time=0.99 min.

28.1 2-Iodo-isonicotinonitrile

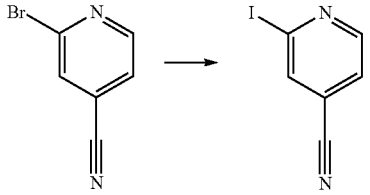

Analogously to intermediate 20.1 obtained by starting from 2-bromo-isonicotinonitrile (purchased from Activate), acetyl chloride and sodium iodide.

Yield: 87% of theory 29.2 2-Iodo-isonicotinamide

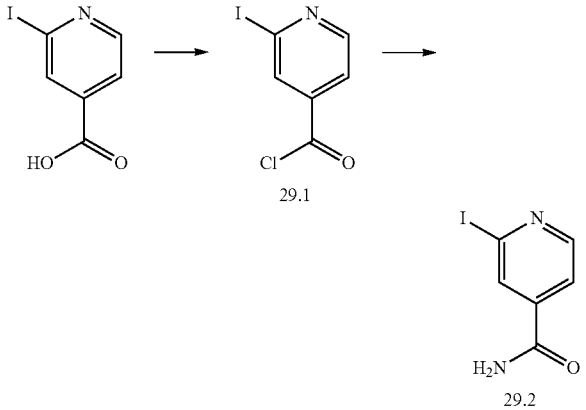

29.1 2-Iodo-isonicotinoyl chloride

To a solution of 2-iodoisonicotinic acid (purchased from Adesis) (0.750 g, 3.01 mmol) dissolved in 10 ml of dichloromethane is added oxalylchloride (0.284 ml, 3.31 mmol). The mixture is stirred at room temperature for 18 hours and used as such for next step.

Yield: 0.80 g (99% of theory)

29.2 2-Iodo-isonicotinamide

To the crude reaction solution containing 2-iodo-isonicotinoyl chloride 29.1 (0.800 g, 2.99 mmol) in 10 mL dichloromethane is added ammonia solution (32% aqueous solution, 1.59 g, 29.9 mmol), stirred for 30 minutes and concentrated under reduced pressure.

Yield: 0.49 g (65% of theory)

32.2 5-Bromo-2-iodo-4-trifluoromethyl-pyridine

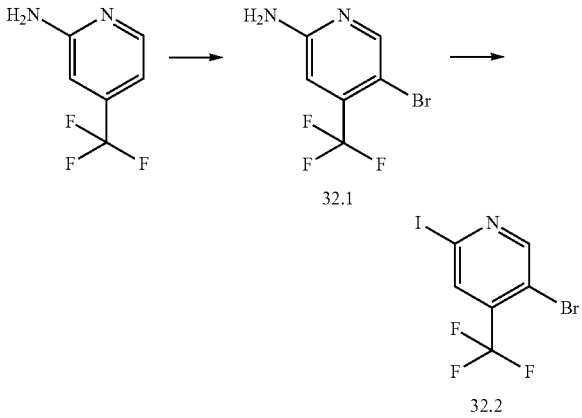

32.1

32.2

32.1 5-Bromo-4-trifluoromethyl-pyridin-2-ylamine

Analogously to example 19.1, obtained by starting from 4-trifluoromethyl-pyridin-2-ylamine (purchased from Manchester) and 1-bromo-pyrrolidine-2,5-dione. The mixture is poured into water, extracted with ethyl acetate and washed with a half saturated aqueous solution of sodium bicarbonate. The organic phase is dried and concentrated under reduced pressure.

Yield: 1.43 g (96% of theory)

Mass spectrometry (ESI$^-$): m/z=240, 242 $[M+H]^+$ 32.2 5-Bromo-2-iodo-4-trifluoromethyl-pyridine Analogously to example 19.2 obtained by starting from 5-bromo-4-trifluoromethyl-pyridin-2-ylamine 32.1 and tert-butyl nitrite.

Yield: 60% of theory 33.3
6-Iodo-3-trifluoromethoxy-pyridine-2-carbonitrile

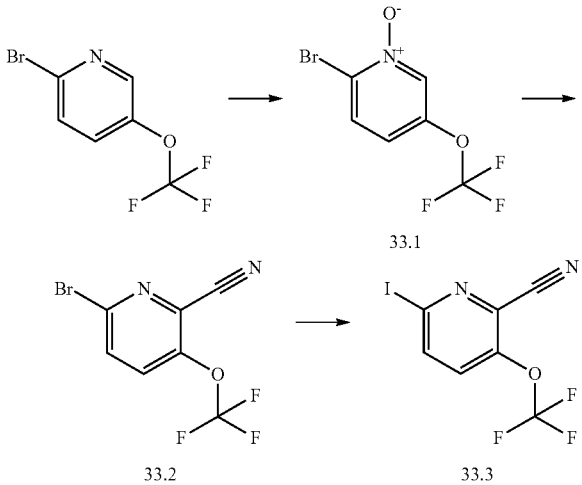

33.1

33.2

33.3

33.1 2-bromo-5-(trifluoromethoxy)pyridin-1-ium-1-olate

Commercially available 2-bromo-5-(trifluoromethoxy)pyridine (Manchester) is dissolved in 20 mL of dichloromethane and cooled to 0° C. Trifluoroacetic acid anhydride (2.26 mL, 16.1 mmol) and hydrogen peroxide (35% solution in water, 0.941 mL, 10.7 mmol) are added and the mixture is stirred for 18 hours. The reaction mixture slowly poured into saturated aqueous sodium bicarbonate solution and extracted with dichloromethane. The combined organic phases are dried and concentrated under reduced pressure.

Yield: 1.40 g (100% of theory)

Mass spectrometry (ESI$^-$): m/z=257, 259 $[M+H]^+$

HPLC (Method 3): Retention time=0.728 min.

33.2 6-Bromo-(3-trifluoromethoxy)pyridine-2-carbonitrile 2-bromo-5-(trifluoromethoxy)pyridin-1-ium-1-olate 33.1 (1.40 g, 5.43 mmol) is dissolved in 10 mL of acetonitrile. Triethylamine (1.14 mL, 8.1 mmol) and trimethylsilylcyanide (1.46 mL, 10.8 mmol) are added and the mixture is stirred at 80° C. for 40 hours. The mixture is diluted with ethyl acetate, concentrated under reduced pressure and purified by chromatography on silica gel (using a solvent gradient of cyclohexane/ethyl acetate from 100/0 to 80/20).

Yield: 0.80 $_g$ (55% of theory)

Mass spectrometry (ESI$^-$): m/z=266, 268 $[M+H]^+$

HPLC (Method 3): Retention time=1.03 min.

33.3
6-Iodo-3-trifluoromethoxy-pyridine-2-carbonitrile

Analogously to example 4.1 obtained by starting from 6-bromo-3-trifluoromethoxy-pyridine-2-carbonitrile 33.2 and stirred at 110° C. for 20 hours. Ammonia (32% solution, 40 mL) is added and the reaction is poured into water and extracted with dichloromethane, dried with sodium sulfate and concentrated under reduced pressure.

Yield: 94% of theory

Mass spectrometry (ESI$^-$): m/z=315 $[M+H]^+$

HPLC (Method 1): Retention time=0.99 min.

34.1 2-Iodo-4-trifluoromethyl-pyrimidine

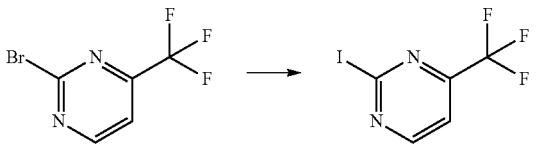

Analogously to example 46.3 obtained by starting from 2-bromo-4-trifluoromethyl-pyrimidine (purchased from Activate) and hydriodic acid (57% aqueous solution). The mixture is dissolved in dioxane (5 mL) and stirred for 3 hours at 50° C. The mixture is then extracted with ethyl acetate and washed with a half saturated aqueous solution of sodium bicarbonate. The organic phases are washed with a 20% aqueous solution of sodium thiosulfate and a half saturated aqueous solution of sodium chloride. The organic phases are dried and concentrated.

Yield: 96% of theory

HPLC (Method 1): Retention time=0.90 min.

35.1 2-iodo-5-(trifluoromethyl)pyrimidine

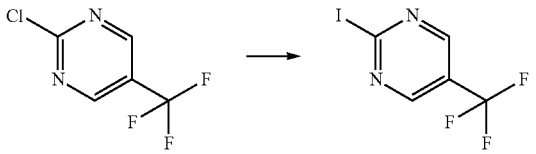

Analogously to example 46.3, obtained by starting from 2-chloro-5-(trifluoromethyl)pyrimidine (purchased from Manchester), sodium iodide and hydriodic acid (57% aqueous solution). The mixture is dissolved in dioxane (30 mL), stirred for 1 hour at 80° C., cooled to room temperature and extracted with ethyl acetate and washed with a half saturated aqueous solution of sodium bicarbonate. The organic phases are washed with a 20% aqueous solution of sodium thiosulfate and a half saturated aqueous solution of sodium chloride. The organic phases are dried and concentrated.

Yield: 100% of theory 36.1

6-iodo-4-(trifluoromethyl)pyridine-2-carbonitrile

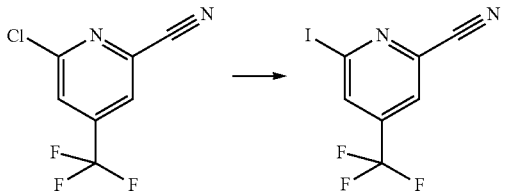

Analogously to intermediate 20.1, obtained by starting from 6-chloro-4-(trifluoromethyl)pyridine-2-carbonitrile (purchased from Arkpharma), acetyl chloride and sodium iodide. The mixture is stirred at 50° C. for 18 hours. The mixture is poured into an aqueous solution of sodium bicarbonate and extracted with dichloromethane. The organic phase is dried and concentrated. The residue is purified by flash column chromatography on silica gel (using a solvent gradient from cyclohexane/ethyl acetate 100/0 to 90/10).

Yield: 66% of theory

Mass spectrometry (ESI$^-$): m/z=299 $[M+H]^+$

HPLC (Method 1): Retention time=0.98 min.

37.3

3-(difluoromethyl)-6-iodopyridine-2-carbonitrile

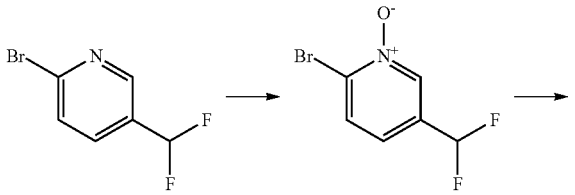

37.1

-continued

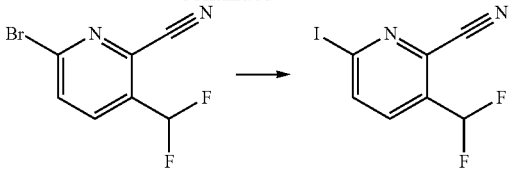

37.2 37.3

37.1

2-bromo-5-(difluoromethyl)pyridin-1-ium-1-olate

Analogously to example 33.1, obtained by starting from 2-bromo-5-difluoromethyl-pyridine (purchased from Manchester).

Yield: 79% of theory 37.2

6-bromo-3-(difluoromethyl)pyridine-2-carbonitrile

To a solution of 2-bromo-5-(difluoromethyl)pyridin-1-ium-1-olate 37.1 (10.0 g, 44.6 mmol) in 10 mL acetonitrile is added triethylamine (9.4 ml, 67.0 mmol) and trimethylsilyl cyanide (12.0 ml, 89.3 mmol). The mixture is stirred at 80° C. for 18 hours, silica gel is added and the solvent is concentrated under reduced pressure. The mixture is purified by silica gel chromatography (eluent: cyclohexane/ethyl acetate 100/0→75/25).

Yield: 6.3 g (61% of theory)

37.3

3-(difluoromethyl)-6-iodopyridine-2-carbonitrile

Analogously to intermediate 20.1, obtained by starting from 6-bromo-3-(difluoromethyl)pyridine-2-carbonitrile 37.2, acetyl chloride and sodium iodide. The mixture is stirred at 50° C. for 30 minutes. Ethyl acetate is added and the mixture is washed with a half concentrated aqueous sodium bicarbonate solution, a 20% aqueous solution of sodium thiosulfate solution and brine. The organic phase is dried and concentrated.

Yield: 95% of theory

Mass spectrometry (ESI$^-$): m/z=280 $[M+H]^+$ 38.1 4-chloro-6-iodopyridine-2-carbonitrile

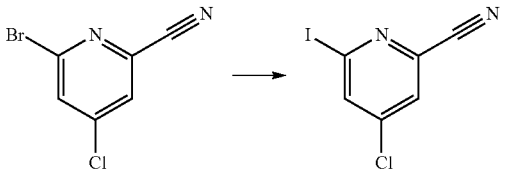

Analogously to example 4.1, obtained by starting from 6-bromo-4-chloropyridine-2-carbonitrile (purchased from Enamine) and stirred at 110° C. for 20 hours. Ammonia (32% in water, 40 mL) is added and the reaction is diluted with water. The aqueous phase is extract with dichloromethane, dried with sodium sulfate and concentrated under reduced pressure.

Yield: 95% of theory 39.1 5-cyclopropyl-2-iodopyridine

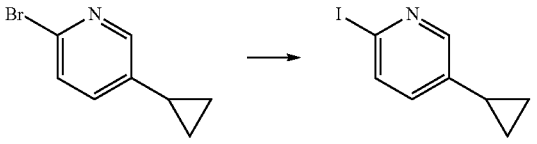

2-bromo-5-cyclopropylpyridine (purchased from Combi-Phos) (500 mg, 2.52 mmol) is dissolved in 5 mL of dioxane. Copper (I) iodide (96.2 mg, 0.50 mmol), sodium iodide (946 mg, 6.31 mmol) and N,N'-dimethylethylenediamine (105 mg, 1.01 mmol) are added and the mixture is stirred at 130° C. for 2 hours. Ethyl acetate is added and the mixture is washed with half concentrated aqueous sodium bicarbonate solution. The organic phase is dried and concentrated under reduced pressure.

Yield: 541 mg (87% of theory)

Mass spectrometry (ESI$^+$): m/z=245 $[M+H]^+$

HPLC (Method 2): Retention time=0.97 min.

40.2 5-cyclopropyl-2-iodopyridine-4-carbonitrile

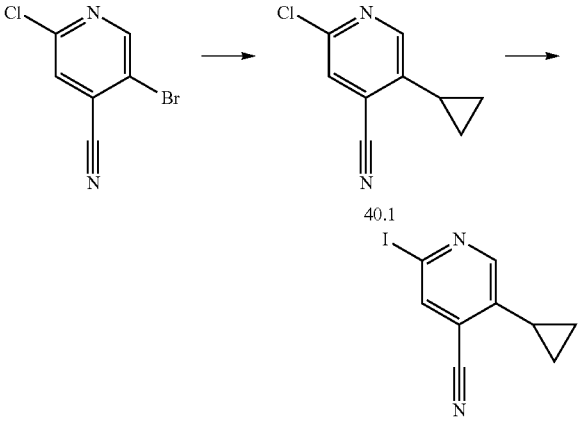

40.1

40.2

40.1 2-chloro-5-cyclopropylpyridine-4-carbonitrile

Under an atmosphere of argon 5-bromo-2-chloropyridine-4-carbonitrile (purchased from Apollo) (100 mg, 0.46 mmol) is dissolved in 2.5 mL of tetrahydrofuran. 1,1'-Bis-(diphenylphosphino)-ferrocenedichloropalladium (11) (110 mg, 0.15 mmol) and cyclopropylzinc bromide (4.6 mL, 2.30 mmol) are added and the mixture is stirred at 50° C. for 18 hours. The reaction is quenched with sodium bicarbonate solution and extracted with dichloromethane. The organic phase is dried and concentrated under reduced pressure. The residue is purified by flash column chromatography on silica gel (using a solvent gradient from petrolether/ethyl acetate 99/1 to 62/38).

Yield: 35 mg (43% of theory)

Mass spectrometry (ESI$^+$): m/z=179 $[M+H]^+$

HPLC (Method 2): Retention time=0.97 min.

40.2 5-cyclopropyl-2-iodopyridine-4-carbonitrile

Analogously to intermediate 20.1 obtained by starting from 2-chloro-5-cyclopropylpyridine-4-carbonitrile 40.1, sodium iodide and acetyl chloride. The mixture is stirred at 80° C. for 4 hours. Ethyl acetate is added and the mixture is washed with a half concentrated aqueous sodium bicarbonate solution and 20% aqueous solution of sodium thiosulfate solution and washed with brine. The organic phase is dried and concentrated under reduced pressure. The residue is purified by RP-HPLC (modifier: formic acid)

Yield: 64% of theory

Mass spectrometry (ESI$^-$): m/z=270 $[M+H]^+$

HPLC (Method 2): Retention time=0.999 min.

41.2 5-cyclopropoxy-2-iodopyridine

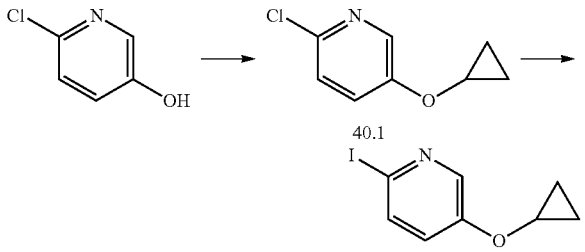

40.1

41.2

41.1

5-cyclopropoxy-2-chloropyridine was prepared as described in WO2014/114578 page 99 and 101

41.2 5-cyclopropoxy-2-iodopyridine

Analogously to intermediate 20.1 obtained by starting from 2-chloro-5-cyclopropoxypyridine 41.1, sodium iodide and acetyl chloride in acetonitrile. The mixture is stirred at 80° C. for 2 days. Ethyl acetate is added and the mixture is washed with a half concentrated aqueous sodium bicarbonate solution, a 10% aqueous sodium thiosulfate solution and brine. The organic phase is dried and concentrated. The residue is purified by RP-HPLC (modifier: formic acid)

Yield: 8% of theory

Mass spectrometry (ESI$^-$): m/z=261 $[M+H]^+$

HPLC (Method 2): Retention time=0.99 min.

42.2 3-cyclopropyl-6-iodopyridine-2-carbonitrile

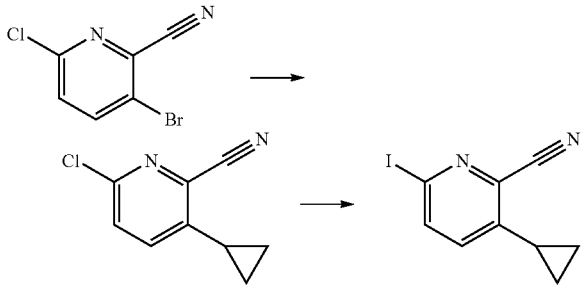

42.1

42.2

42.1 6-chloro-3-cyclopropylpyridine-2-carbonitrile

Analogously to example 40.1 obtained by starting from 3-bromo-6-chloro-pyridine-2-carbonitrile (from Aldrich).

Yield: 1.44 g (87% of theory)

Mass spectrometry (ESI$^+$): m/z=179 [M+H]$^+$

HPLC (Method 1): Retention time=0.98 min.

42.2 3-cyclopropyl-6-iodopyridine-2-carbonitrile

Analogously to intermediate 20.1 obtained by starting from 6-chloro-3-cyclopropylpyridine-2-carbonitrile 42.1, sodium iodide and acetyl chloride in acetonitrile. The mixture is stirred at 80° C. for 2 days. Ethyl acetate is added and the mixture is washed with a half concentrated aqueous sodium bicarbonate solution, a 10% aqueous sodium thiosulfate solution and brine. The organic phase is dried and concentrated under reduced pressure. The residue is purified by chromatography on silica gel (using a solvent gradient from cyclohexane/ethyl acetate 94/6 to 84/16).

Yield: 29% of theory

Mass spectrometry (ESI$^-$): m/z=270 [M+H]$^+$

HPLC (Method 1): Retention time=0.99 min.

43.3 2-cyclopropyl-6-iodopyridine-3-carbonitrile

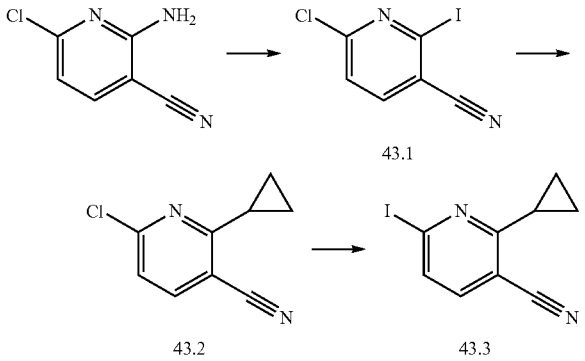

43.1

6-chloro-2-iodopyridine-3-carbonitrile was prepared as described in US2016/0075704 paragraph 287-289

43.2 6-chloro-2-cyclopropylpyridine-3-carbonitrile

Analogously to example 40.1 obtained by starting from 6-chloro-2-iodopyridine-3-carbonitrile 43.1.

Yield: 926 mg (69% of theory)

Mass spectrometry (ESI$^+$): m/z=179 [M+H]$^+$

HPLC (Method 2): Retention time=1.04 min.

43.3 2-cyclopropyl-6-iodopyridine-3-carbonitrile

Analogously to intermediate 20.1 obtained by starting from 6-chloro-2-cyclopropylpyridine-3-carbonitrile 43.2, sodium iodide and acetyl chloride in acetonitrile. The mixture is stirred at 80° C. for 2 days. Ethyl acetate is added and the mixture is washed with a half concentrated aqueous sodium bicarbonate solution, a 10% solution of sodium thiosulfate solution and brine. The organic phase is dried and concentrated under reduced pressure. The residue is purified by chromatography on silica gel (using a solvent gradient from petrolether/dichloromethane 92/8 to 53/47).

Yield: 118 mg (9% of theory)

Mass spectrometry (ESI$^-$): m/z=270 [M+H]$^+$

HPLC (Method 1): Retention time=1.06 min.

44.1 2-Iodo-5-methylsulfanyl-pyridine

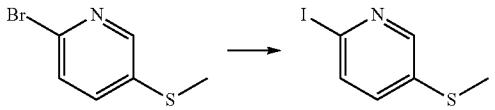

Analogously to example 4.1, obtained by starting from 2-Bromo-5-(methylthio)pyridine (from Chembridge). The reaction mixture is stirred at 110° C. for 20 hours. Ammonia (32% solution, 40 mL) is added, the reaction is poured into water and extracted with dichloromethane. The organic phase is dried and concentrated under reduced pressure.

Yield: 97% of theory

Mass spectrometry (ESI$^-$): m/z=252 [M+H]$^+$

HPLC (Method 1): Retention time=0.93 min.

45.2 (E)-N'-(5-cyano-2-iodopyrimidin-4-yl)-N,N-dimethylmethanimidamide

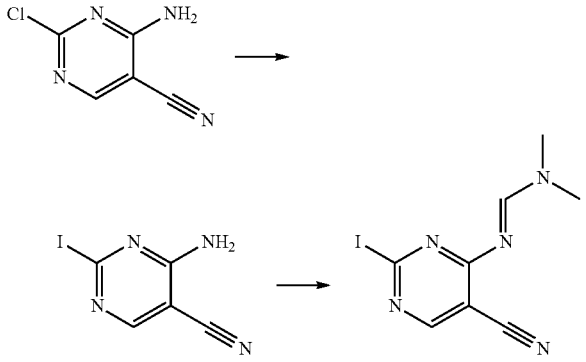

45.1 4-amino-2-iodopyrimidine-5-carbonitrile

4-Amino-2-chloropyrimidine-5-carbonitrile (from Alfa) (0.80 g, 5.18 mmol) is dissolved in 8 mL of acetonitrile. Iodotrimethylsilane (0.7 mL, 5.18 mmol) is added and the mixture is stirred at 80° C. for 4 hours. Ethyl acetate is added and the mixture is washed with a concentrated aqueous sodium bicarbonate solution. The organic phase is dried and concentrated under reduced pressure.

Yield: 1.0 g (81% of theory)

Mass spectrometry (ESI$^+$): m/z=247 [M+H]$^+$ 45.2 (E)-N'-(5-cyano-2-iodopyrimidin-4-yl)-N,N-dimethylmethanimidamide Analogously to example 164.1 obtained by starting from 4-amino-2-iodopyrimidine-5-carbonitrile 45.1. The mixture is stirred for 2 hours. Ethyl acetate is added and the mixture is washed with a half concentrated aqueous sodium bicarbonate solution. The organic phase is dried and concentrated under reduced pressure.

Yield: 490 mg (80% of theory)

46.3 2-iodo-5-(trifluoromethyl)pyrimidin-4-amine

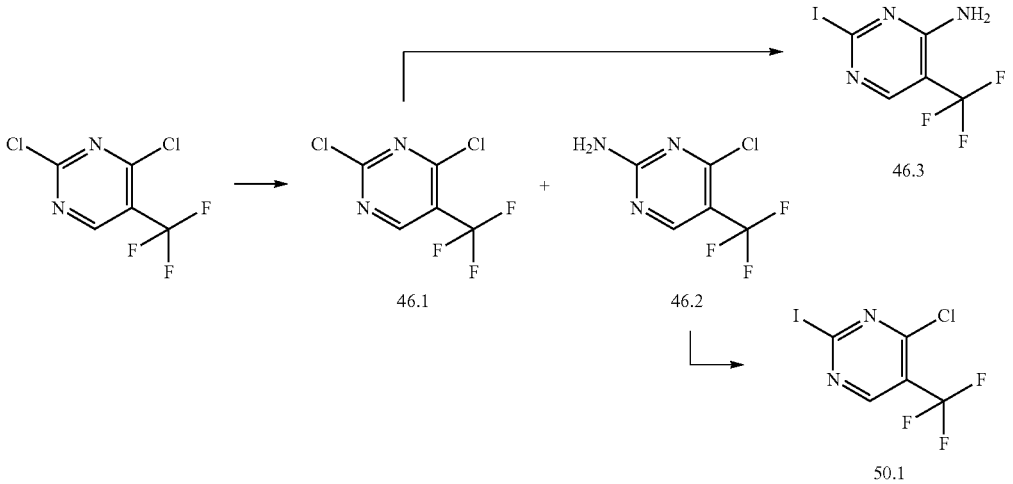

46.1 2-chloro-5-(trifluoromethyl)pyrimidin-4-amine 2,4-dichloro-5-(trifluoromethyl)pyrimidine (from Tosch) (40.0 g, 184 mmol) is dissolved in 300 mL of tetrahydrofuran and the mixture is cooled to 0° C. Ammonia (32% in water; 30.0 mL, 496 mmol) is added dropwise and the mixture is stirred at room temperature for 18 hours. Ethyl acetate is added and the reaction mixture is washed with a saturated aqueous sodium bicarbonate solution. The organic phase is concentrated under reduced pressure and purified by chromatography on silica gel (using a solvent gradient of cyclohexane/ethyl acetate from 100/0 to 50/50).

Yield: 17.6 g (48% of theory)

Mass spectrometry (ESI$^+$): m/z=198 [M+H]$^+$

HPLC (Method 4): Retention time=0.69 min.

46.2 4-chloro-5-(trifluoromethyl)pyrimidin-2-amine

Obtained as a side-product using 2,4-dichloro-5-(trifluoromethyl)pyrimidine and ammonia.

Yield: 18.6 g (48% of theory)

Mass spectrometry (ESI$^+$): m/z=198 [M+H]$^+$

HPLC (Method 4): Retention time=0.81 min.

46.3 2-iodo-5-(trifluoromethyl)pyrimidin-4-amine 2-chloro-5-(trifluoromethyl)pyrimidin-4-amine 46.1 (3.00 g, 15.2 mmol) and sodium iodide (6.83 g, 45.6 mmol) are suspended in 30 mL dioxane. Hydriodic acid (57% aqueous solution; 1.76 mL, 15.2 mmol) is added and the mixture is stirred at 50° C. for 30 minutes. Saturated aqueous sodium bicarbonate solution is added and the precipitate is collected by filtration. The solid is purified by chromatography on silica gel (using a solvent gradient from cyclohexane/ethyl acetate 100/0 to 80/20).

Yield: 1.90 g (43% of theory)

Mass spectrometry (ESI$^-$): m/z=290 [M+H]$^+$

HPLC (Method 1): Retention time=0.75 min.

50.1 4-chloro-2-iodo-5-(trifluoromethyl)pyrimidine 4-chloro-5-(trifluoromethyl)pyrimidin-2-amine 46.2 (5.00 g, 25.31 mmol) is dissolved in 5 mL acetonitrile. Diiodomethane (20.0 mL, 248.3 mmol) and tert-butylnitrite (6.02 mL, 50.62 mmol) are added and the mixture is stirred at 70° C. for 2 hours. The mixture is concentrated under reduced pressure, the residue is dissolved in ethyl acetate and washed with a 10% aqueous sodium thiosulfate solution and a saturated aqueous sodium bicarbonate solution. The organic phase is washed with brine, dried, concentrated under reduced pressure and purified by chromatography on silica gel (using a solvent gradient of cyclohexane/ethyl acetate from 100/0 to 80/20).

Yield: 3.74 g (48% of theory)

Mass spectrometry (ESI$^+$): m/z=308 [M+H]$^+$

HPLC (Method 4): Retention time=0.98 min.

47.1 3-chloro-6-iodopyridine-2-carbonitrile

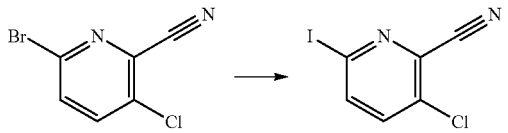

Analogously to intermediate 20.1 obtained by starting from 6-bromo-3-chloro-2-cyanopyridine (from Matrix), sodium iodide and acetyl chloride in acetonitrile. Stirred 18 hours at 50° C. and cooled, extracted with ethyl acetate and washed with a half saturated aqueous solution of sodium bicarbonate. The organic phases are extracted with a 20% aqueous solution of sodium thiosulfate and a half saturated aqueous solution of sodium chloride. The organic phases are dried and concentrated under reduced pressure. The residue is purified by RP-HPLC (modifier: trifluoroacetic acid)

Yield: 45% of theory

Mass spectrometry (ESI$^-$): m/z=265 [M+H]$^+$

HPLC (Method 2): Retention time=0.98 min.

48.3
6-iodo-3-(trifluoromethyl)pyridine-2-carbonitrile

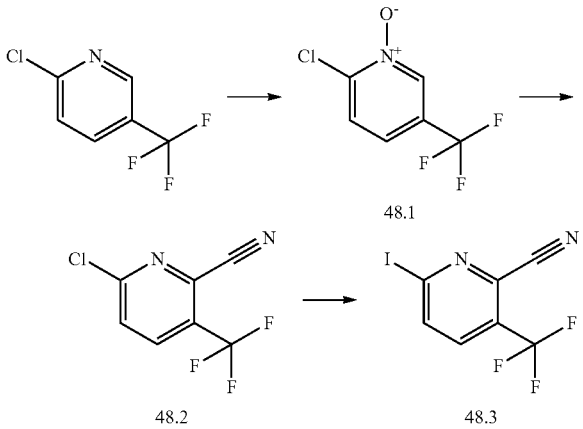

48.2

6-chloro-3-(trifluoromethyl)pyridine-2-carbonitrile was prepared as described in US2008/275057 page 81

48.3
6-iodo-3-(trifluoromethyl)pyridine-2-carbonitrile

Analogously to intermediate 20.1, obtained by starting from 6-chloro-3-(trifluoromethyl)pyridine-2-carbonitrile 48.2, acetyl chloride and sodium iodide. The mixture is stirred at 50° C. for 3 days. Diethyl ether is added and the mixture is washed with a saturated aqueous solution of sodium bicarbonate, a saturated aqueous solution of sodium thiosulfate and a saturated aqueous solution of sodium chloride.

The organic phases are dried and concentrated under reduced pressure.

Yield: 59% of theory

Mass spectrometry (ESI$^-$): m/z=299 $[M+H]^+$

HPLC (Method 1): Retention time=0.97 min.

51.1 2-iodopyrimidine-4-carbonitrile

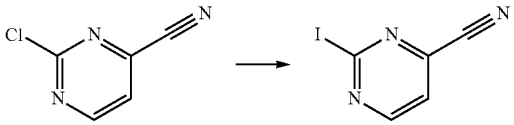

Analogously to example 46.3 obtained by starting from 2-chloropyrimidine-4-carbonitrile (from Activate), sodium iodide and hydriodic acid (57% aqueous solution). The mixture is dissolved in dioxane (15 mL) and stirred for 1.5 hours at 100° C. The mixture is cooled to room temperature, extracted with ethyl acetate and washed with a half saturated aqueous solution of sodium bicarbonate. The organic phases are washed a 20% aqueous solution of sodium thiosulfate and a half saturated aqueous solution of sodium chloride. The organic phases are dried and concentrated. The residue is purified by flash column chromatography on silica gel (using a solvent gradient from cyclohexane/ethyl acetate 100/0 to 80/20).

Yield: 72% of theory

Mass spectrometry (ESI$^-$): m/z=231 $[M+H]^+$

HPLC (Method 1): Retention time=0.58 min.

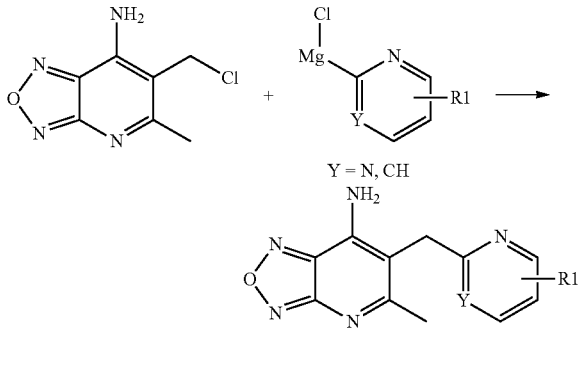

Example 1

6-(5-Methoxy-pyridin-2-ylmethyl)-5-methyl-[1,2,5]oxadiazolo[3,4-b]pyridin-7-ylamine

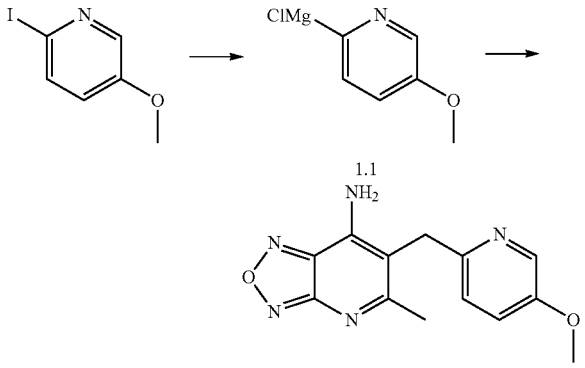

Ex. 1

1.1 (5-methoxypyridin-2-yl)magnesium Chloride

Commercially available (from Activate) 2-iodo-5-methoxypyridine (0.50 g, 2.13 mmol) is dissolved in 3.0 mL of tetrahydrofuran and the mixture is cooled to −40° C. Isopropyl-magnesium chloride lithiumchloride complex (1.3 M solution, 1.64 mL, 2.13 mmol) is added at −40° C. and the mixture is stirred for 30 minutes. The crude mixture is kept at −40° C. and directly used for the next step.

Final Step (Example 1)

To (5-methoxypyridin-2-yl)magnesium chloride 1.1 (350 mg, 2.08 mmol) at −40° C. is added copper(I)cyanide di(lithium chloride) complex (1 mol/L in tetrahydrofuran, 0.18 mL, 0.18 mmol) and the reaction mixture is stirred for 5 minutes at −40° C. 6-chloromethyl-5-methyl-[1,2,5]oxadiazolo[3,4-b]pyridin-7-ylamine C (110 mg, 0.44 mmol) in 1.0 mL of tetrahydrofuran is slowly added and the mixture is stirred at −40° C. When complete conversion is observed by HPLC-MS, the reaction mixture is diluted with methanol, concentrated under reduced pressure and purified by RP-HPLC (modifier: ammonium hydroxide)

Yield: 38 mg (32% of theory)

Mass spectrometry (ESI$^+$): m/z=272 [M+H]$^+$

HPLC (Method 1): Retention time=0.80 min.

Example 2

2-(7-Amino-5-methyl-[1,2,5]oxadiazolo[3,4-b]pyridin-6-ylmethyl)-5-trifluoromethyl-isonicotinonitrile

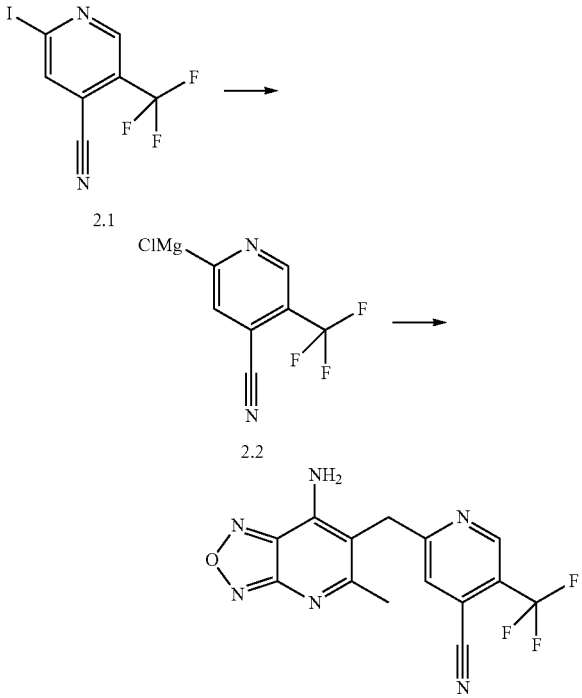

Ex. 2

2.2 4-cyano-5-(trifluoromethyl)-2-pyridyl]-magnesium Chloride

Analogously to example 1.1, obtained by starting from 2-iodo-5-(trifuoromethyl)pyridine-4-carbonitrile 2.1 and isopropylmagnesium chloride lithiumchloride complex (1.3 M solution) at −62° C.

Final Step (Example 2)

Obtained analogously to example 1 by reacting 6-chloromethyl-5-methyl-[1,2,5]oxadiazolo[3,4-b]pyridin-7-ylamine C with [4-cyano-5-(trifluoromethyl)-2-pyridyl] magnesium chloride 2.2 at −65° C. When complete conversion is observed by HPLC-MS, the reaction mixture is quenched with methanol. The reaction mixture is concentrated under reduced pressure and the residue is partitioned between dichloromethane and water. The organic phase is dried over magnesium sulfate and concentrated. The residue is purified by RP-HPLC (modifier: ammonium hydroxide).

Yield: 4% of theory

Mass spectrometry (ESI$^+$): m/z=335 [M+H]$^+$

HPLC (Method 1): Retention time=0.87 min.

Example 3

6-(6-Chloro-pyridin-2-ylmethyl)-5-methyl-[1,2,5]oxadiazolo[3,4-b]pyridin-7-ylamine

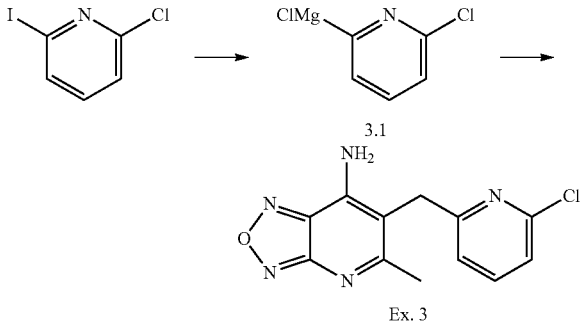

Ex. 3

3.1 (6-chloro-2-pyridyl)-magnesium Chloride

Analogously to example 1.1 obtained by starting from 2-chloro-6-iodo-pyridine (from Anichem) and isopropylmagnesium chloride lithiumchloride complex (1.3 M solution in tetrahydrofuran) at −45° C.

Final Step (Example 3)

Obtained analogously to example 1 by reacting 6-chloromethyl-5-methyl-[1,2,5]oxadiazolo[3,4-b]pyridin-7-ylamine C with (6-chloro-2-pyridyl)-magnesium chloride 3.1 at −45° C. When complete conversion is observed by HPLC-MS the reaction mixture is diluted with methanol, concentrated under reduced pressure and purified by RP-HPLC (modifier: ammonium hydroxide)

Yield: 33% of theory

Mass spectrometry (ESI$^+$): m/z=276 [M+H]$^+$

HPLC (Method 1): Retention time=0.86 min.

Example 4

6-(7-Amino-5-methyl-[1,2,5]oxadiazolo[3,4-b]pyridin-6-ylmethyl)-nicotinonitrile

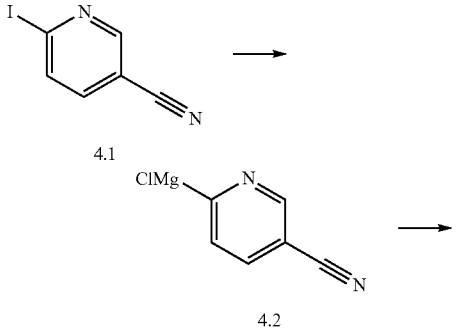

-continued

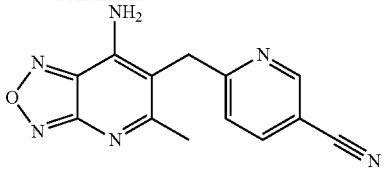

Ex. 4

4.2 (5-cyano-2-pyridyl)-magnesium Chloride

Analogously to example 1.1 obtained by starting from 6-Iodo-nicotinonitrile 4.1 and isopropylmagnesium chloride lithiumchloride complex (1.3 M solution) at −60° C.

Final Step (Example 4)

Obtained analogously to example 1 by reacting 6-chloromethyl-5-methyl-[1,2,5]oxadiazolo-[3,4-b]pyridin-7-ylamine C with (5-cyano-2-pyridyl)-magnesium chloride 4.2 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The combined organic phase are dried, concentrated and purified by silica gel chromatography (eluent: cyclohexane/ethyl acetate 0%→65%). The product is recrystallized from ethyl acetate.

Yield: 20% of theory

Mass spectrometry (ESI$^+$): m/z=267 [M+H]$^+$

HPLC (Method 1): Retention time=0.73 min.

Example 5

6-(5-Bromo-pyridin-2-ylmethyl)-5-methyl-[1,2,5]oxadiazolo[3,4-b]pyridin-7-ylamine

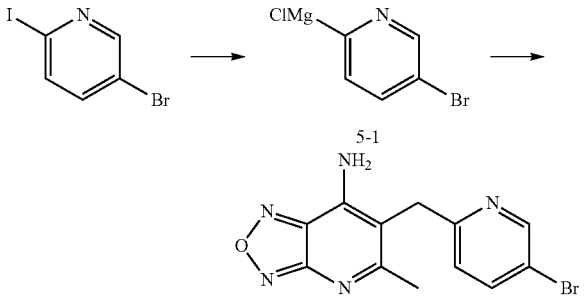

5-1

Ex. 5

5.1 (5-bromo-2-pyridyl)-magnesium Chloride

Analogously to example 1.1 obtained by starting from 5-Bromo-2-iodopyridine (from ABCR) and isopropylmagnesium chloride lithiumchloride complex (1.3 M solution) at −60° C.

Final Step (Example 5)

Obtained analogously to example 1 by reacting 6-chloromethyl-5-methyl-[1,2,5]oxadiazolo-[3,4-b]pyridin-7-ylamine C with (5-bromo-2-pyridyl)-magnesium chloride 5.1 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 54% of theory

Mass spectrometry (ESI$^+$): m/z=320, 322 [M+H]$^+$

HPLC (Method 1): Retention time=0.84 min.

Example 6

5-Methyl-6-(5-trifluoromethyl-pyridin-2-ylmethyl)-[1,2,5]oxadiazolo[3,4-b]pyridin-7-ylamine

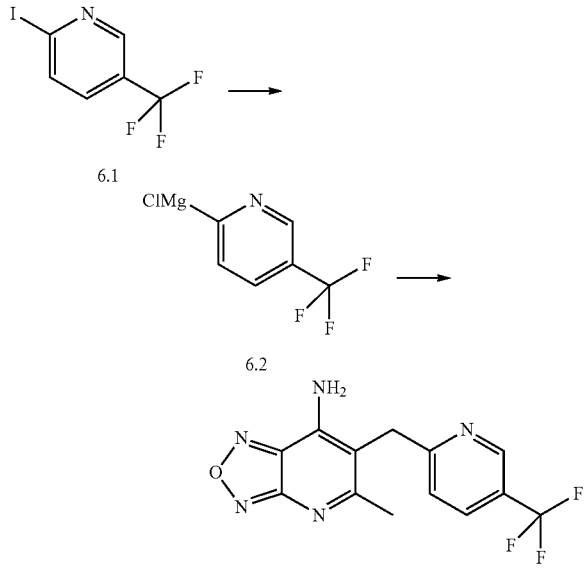

6.1

6.2

Ex. 6

6.2 [5-(trifluoromethyl)-2-pyridyl]-magnesium Chloride

Analogously to example 1.1 obtained by starting from 2-Iodo-5-trifluoromethyl-pyridine 6.1 and isopropylmagnesium chloride lithiumchloride complex (1.3 M solution) at −60° C.

Final Step (Example 6)

Obtained analogously to example 1 by starting from 6-chloromethyl-5-methyl-[1,2,5]oxadiazolo-[3,4-b]pyridin-7-ylamine C and [5-(trifluoromethyl)-2-pyridyl]-magnesium chloride 6.2. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 49% of theory

Mass spectrometry (ESI$^+$): m/z=310 [M+H]$^+$

HPLC (Method 1): Retention time=0.88 min.

Example 7

6-(6-Bromo-pyridin-2-ylmethyl)-5-methyl-[1,2,5]oxadiazolo[3,4-b]pyridin-7-ylamine

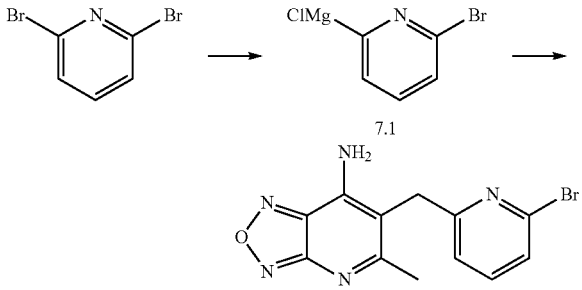

Ex. 7

7.1 (6-bromo-2-pyridyl)-magnesium Chloride

Analogously to example 1.1, obtained by starting from 2,6-Dibromo-pyridine (from Aldrich) and isopropylmagnesium chloride lithiumchloride complex (1.3 M solution) at −60° C.

Final Step (Example 7)

Obtained analogously to example 1 by reacting 6-chloromethyl-5-methyl-[1,2,5]oxadiazolo-[3,4-b]pyridin-7-ylamine C with (6-bromo-2-pyridyl)-magnesium chloride 7.1 at −25° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: trifluoroacetic acid).

Yield: 49% of theory

Mass spectrometry (ESI$^+$): m/z=320, 322 $[M+H]^+$

HPLC (Method 3): Retention time=0.87 min.

Example 8

6-(5-Chloro-pyridin-2-ylmethyl)-5-methyl-[1,2,5]oxadiazolo[3,4-b]pyridin-7-ylamine

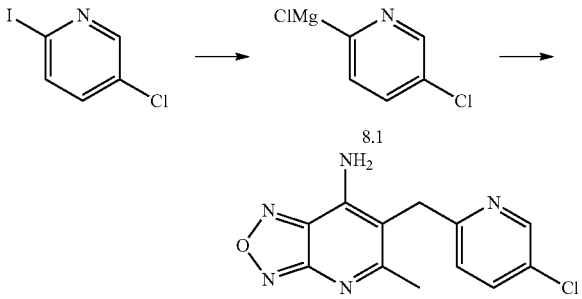

Ex. 8

8.1 (5-chloro-2-pyridyl)-magnesium Chloride

Analogously to example 1.1 obtained by starting from 5-Chloro-2-iodo-pyridine (from Activate) and isopropylmagnesium chloride lithiumchloride complex (1.3 M solution) at −60° C.

Final Step (Example 8)

Obtained analogously to example 1 by reacting 6-chloromethyl-5-methyl-[1,2,5]oxadiazolo[3,4-b]pyridin-7-ylamine C with (5-chloro-2-pyridyl)-magnesium chloride 8.1 at −25° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 59% of theory

Mass spectrometry (ESI$^+$): m/z=276 $[M+H]^+$

HPLC (Method 1): Retention time=0.62 min.

Example 9

6-(5-Difluoromethyl-pyridin-2-ylmethyl)-5-methyl-[1,2,5]oxadiazolo[3,4-b]pyridin-7-ylamine

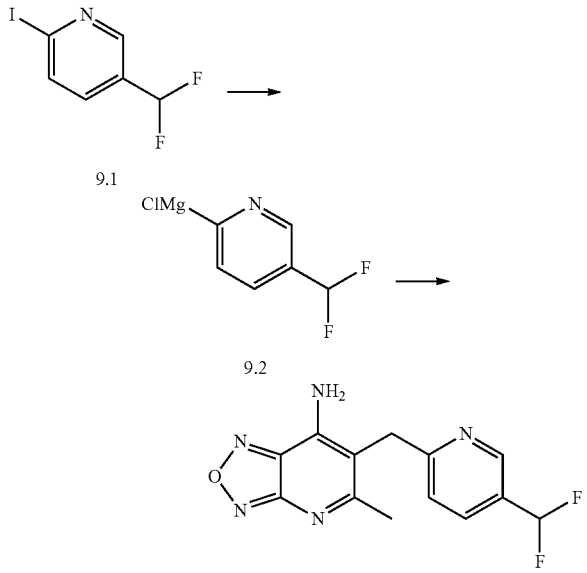

Ex. 9

9.2 [5-(difluoromethyl)-2-pyridyl]-magnesium Chloride

Analogously to example 1.1 obtained by starting from 5-Difluoromethyl-2-iodo-pyridine 9.1 and isopropylmagnesium chloride lithiumchloride complex (1.3 M solution) at −60° C.

Final Step (Example 9)

Obtained analogously to example 1 by reacing 6-chloromethyl-5-methyl-[1,2,5]oxadiazolo-[3,4-b]pyridin-7-ylamine C with [5-(difluoromethyl)-2-pyridyl]-magnesium chloride 9.2 at −25° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 40% of theory

Mass spectrometry (ESI$^+$): m/z=292 [M+H]$^+$

HPLC (Method 1): Retention time=0.78 min.

Example 10

[6-(7-Amino-5-methyl-[1,2,5]oxadiazolo[3,4-b]pyridin-6-ylmethyl)-pyridin-3-yl]-acetic Acid Methyl Ester

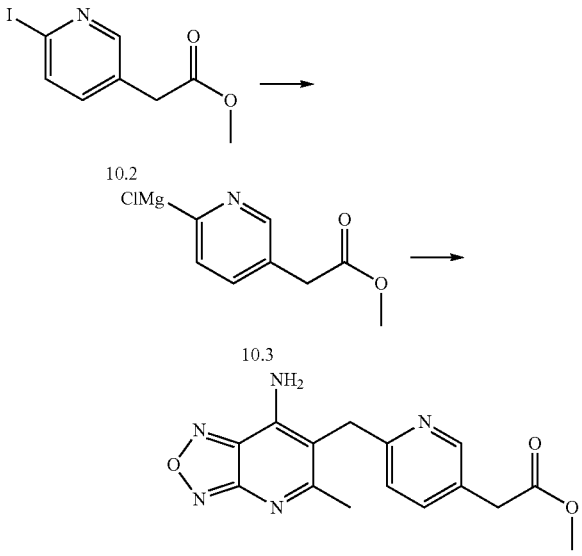

Ex. 10

10.3 [5-(2-methoxy-2-oxo-ethyl)-2-pyridyl]-magnesium Chloride

Analogously to example 1.1, obtained by starting from (6-Iodo-pyridin-3-yl)acetic acid methyl ester 10.2 and isopropylmagnesium chloride lithiumchloride complex (1.3 M solution) at −60° C.

Final Step (Example 10)

Obtained analogously to example 1 by reacting 6-chloromethyl-5-methyl-[1,2,5]oxadiazolo-[3,4-b]pyridin-7-ylamine C with [5-(2-methoxy-2-oxo-ethyl)-2-pyridyl]magnesium chloride 10.3. at −25° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 28% of theory

Mass spectrometry (ESI$^+$): m/z=314 [M+H]$^+$

HPLC (Method 1): Retention time=0.76 min.

Example 11

6-[5-(1,1-Difluoro-ethyl)-pyridin-2-ylmethyl]-5-methyl-[1,2,5]oxadiazolo[3,4-b]pyridin-7-ylamine

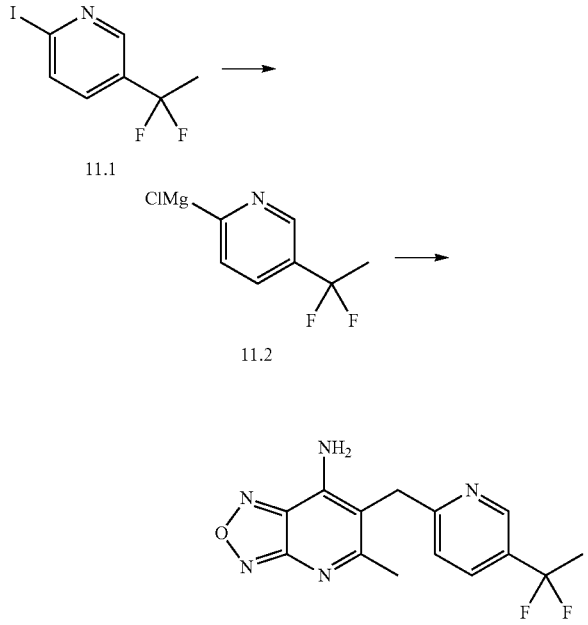

Ex. 11

11.2 [5-(1,1-difluoroethyl)-2-pyridyl]-magnesium Chloride

Analogously to example 1.1, obtained by starting from 5-(1,1-difluoro-ethyl)-2-iodo-pyridine 11.1 and isopropylmagnesium chloride lithiumchloride complex (1.3 M solution) at −60° C.

Final Step (Example 11)

Obtained analogously to example 1 by reacting 6-chloromethyl-5-methyl-[1,2,5]oxadiazolo[3,4-b]pyridin-7-ylamine C with [5-(1,1-difluoroethyl)-2-pyridyl]-magnesium chloride 11.2 at −25° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 44% of theory

Mass spectrometry (ESI$^+$): m/z=306 [M+H]$^+$

HPLC (Method 1): Retention time=0.85 min.

Example 12

6-(5-Fluoro-pyridin-2-ylmethyl)-5-methyl-[1,2,5]oxadiazolo[3,4-b]pyridin-7-ylamine

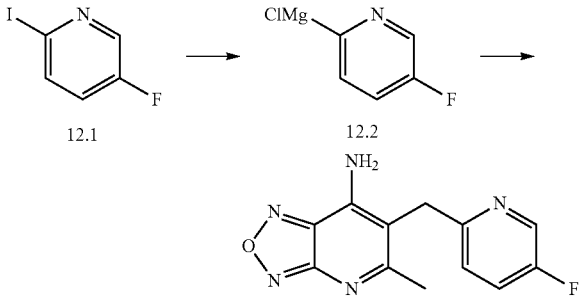

Ex. 12

12.2 (5-fluoro-2-pyridyl)-magnesium Chloride

Analogously to example 1.1 obtained by starting from 5-Fluoro-2-iodo-pyridine 12.1 and isopropylmagnesium chloride lithiumchloride complex (1.3 M solution) at −60° C.

Final Step (Example 12)

Obtained analogously to example 1 by reacting 6-chloromethyl-5-methyl-[1,2,5]oxadiazolo-[3,4-b]pyridin-7-ylamine C with (5-fluoro-2-pyridyl)-magnesium chloride 12.2 at −65° C. When complete conversion is observed by HPLC-MS the reaction mixture is diluted with methanol, concentrated under reduced pressure and purified by RP-HPLC (modifier: ammonium hydroxide).

Yield: 19% of theory

Mass spectrometry ($ESI^+$): m/z=260 $[M+H]^+$

HPLC (Method 1): Retention time=0.76 min.

Example 13

6-(6-Fluoro-pyridin-2-ylmethyl)-5-methyl-[1,2,5]oxadiazolo[3,4-b]pyridin-7-ylamine

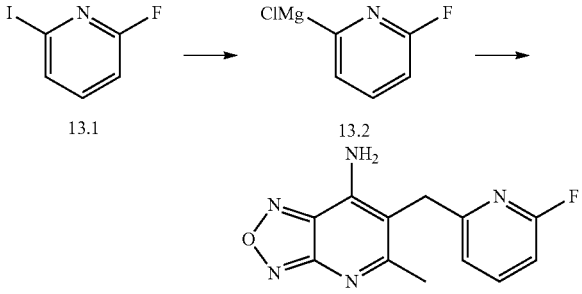

Ex. 13

13.2 (6-fluoro-2-pyridyl)-magnesium Chloride

Analogously to example 1.1 obtained by starting from 2-Fluoro-6-iodo-pyridine 13.1 and isopropylmagnesium chloride lithiumchloride complex (1.3 M solution) at −60° C.

Final Step (Example 13)

Obtained analogously to example 1 by reacting 6-chloromethyl-5-methyl-[1,2,5]oxadiazolo-[3,4-b]pyridin-7-ylamine C with (6-fluoro-2-pyridyl)-magnesium chloride 13.2. at −65° C. When complete conversion is observed by HPLC-MS the reaction mixture is diluted with methanol, concentrated under reduced pressure and purified by RP-HPLC (modifier: ammonium hydroxide).

Yield: 8% of theory

Mass spectrometry ($ESI^+$): m/z=260 $[M+H]^+$

HPLC (Method 1): Retention time=0.78 min.

Example 14

6-(5-Difluoromethoxy-pyridin-2-ylmethyl)-5-methyl-[1,2,5]oxadiazolo[3,4-b]pyridin-7-ylamine

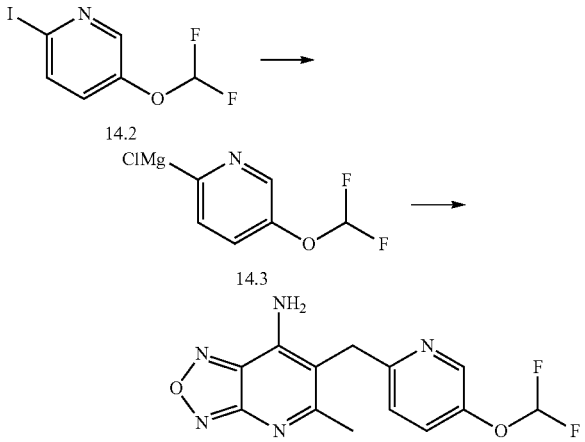

Ex. 14

14.3 [5-(difluoromethoxy)-2-pyridyl]-magnesium Chloride

Analogously to example 1.1 obtained by starting from 5-Difluoromethoxy-2-iodo-pyridine 14.2 and isopropylmagnesium chloride lithiumchloride complex (1.3 M solution) at −45° C.

Final Step (Example 14)

Obtained analogously to example 1 by reacting 6-chloromethyl-5-methyl-[1,2,5]oxadiazolo-[3,4-b]pyridin-7-ylamine C with [5-(difluoromethoxy)-2-pyridyl]-magnesium chloride 14.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: trifluoroacetic acid).

Yield: 7% of theory

Mass spectrometry (ESI$^+$): m/z=308 [M+H]$^+$

HPLC (Method 2): Retention time=0.76 min.

Example 15

6-(6-Bromo-5-difluoromethoxy-pyridin-2-ylmethyl)-5-methyl-[1,2,5]oxadiazolo[3,4-b]pyridin-7-ylamine

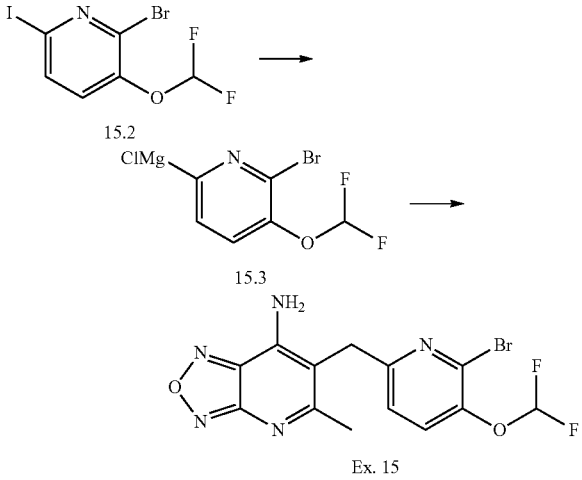

15.3 [6-bromo-5-(difluoromethoxy)-2-pyridyl]-magnesium Chloride

Analogously to example 1.1 obtained by starting from 2-Bromo-3-difluoromethoxy-6-iodo-pyridine 15.2 and isopropylmagnesium chloride lithiumchloride complex (1.3 M solution) at −65° C.

Final Step (Example 15)

Obtained analogously to example 1 by reacting 6-chloromethyl-5-methyl-[1,2,5]oxadiazolo[3,4-b]pyridin-7-ylamine C with [6-bromo-5-(difluoromethoxy)-2-pyridyl]-magnesium chloride 15.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 74% of theory

Mass spectrometry (ESI$^+$): m/z=386, 388 [M+H]$^+$

HPLC (Method 1): Retention time=0.91 min.

Example 16

5-Methyl-6-(6-methylsulfanyl-pyridin-2-ylmethyl)-[1,2,5]oxadiazolo[3,4-b]pyridin-7-ylamine

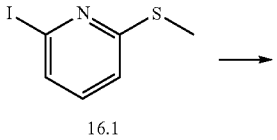

-continued

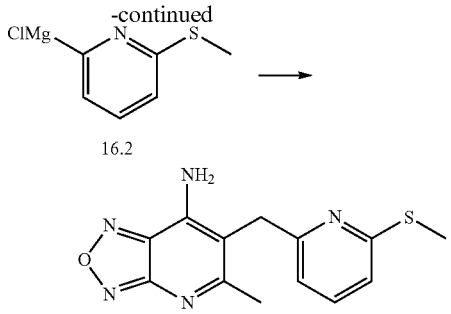

16.2 (6-methylsulfanyl-2-pyridyl)-magnesium Chloride

Analogously to example 1.1 obtained by starting from 2-iodo-6-methylsulfanyl-pyridine 16.1 and isopropylmagnesium chloride lithiumchloride complex (1.3 M solution) at −60° C.

Final Step (Example 16)

Obtained analogously to example 1 by reacting 6-chloromethyl-5-methyl-[1,2,5]oxadiazolo-[3,4-b]pyridin-7-ylamine C with (6-methylsulfanyl-2-pyridyl)-magnesium chloride 16.2 at −65° C. When complete conversion is observed by HPLC-MS the reaction mixture is diluted with methanol, concentrated under reduced pressure and purified by silica gel chromatography (eluent: cyclohexane/ethyl acetate 100/0→20/80).

Yield: 29% of theory

Mass spectrometry (ESI$^+$): m/z=288 [M+H]$^+$

HPLC (Method 3): Retention time=0.90 min.

Example 17

5-Methyl-6-(5-trifluoromethoxy-pyridin-2-ylmethyl)-[1,2,5]oxadiazolo[3,4-b]pyridin-7-ylamine

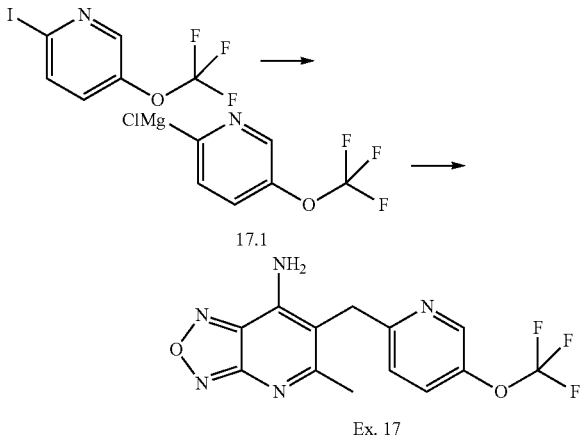

17.1 [5-(trifluoromethoxy)-2-pyridyl]-magnesium Chloride

Analogously to example 1.1, obtained by starting from 5-Difluoromethoxy-2-iodo-pyridine (from GainBiotech) and isopropylmagnesium chloride lithiumchloride complex (1.3 M solution) at −55° C.

Final Step (Example 17)

Obtained analogously to example 1 by reacting 6-chloromethyl-5-methyl-[1,2,5]oxadiazolo[3,4-b]pyridin-7-ylamine C with [5-(trifluoromethoxy)-2-pyridyl]-magnesium chloride 17.1 at −65° C. When complete conversion is observed by HPLC-MS, the reaction mixture is diluted with methanol. The reaction mixture is concentrated under reduced pressure and the residue is partitioned between dichloromethane and water. The organic phase is dried over magnesium sulfate and concentrated. The residue is purified by RP-HPLC (modifier: ammonium hydroxide).

Yield: 26% of theory

Mass spectrometry (ESI$^+$): m/z=326 [M+H]$^+$

HPLC (Method 1): Retention time=0.89 min.

Example 18

6-(2,3-Dihydro-[1,4]dioxino[2,3-b]pyridin-6-ylmethyl)-5-methyl-[1,2,5]oxadiazolo[3,4-b]pyridin-7-ylamine

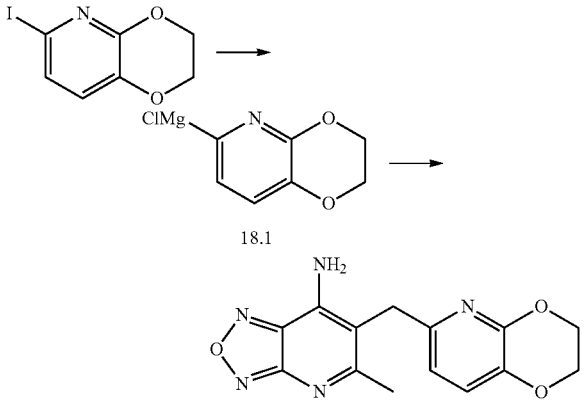

18.1 (2,3-dihydro-)[1,4]dioxino[2,3-b]pyridine-6-yl)-magnesium Chloride

Analogously to example 1.1, obtained by starting from 6-iodo-2,3dihydro-[1,4]dioxino[2,3-b]pyridine (from Adesis) and isopropylmagnesium chloride lithiumchloride complex (1.3 M solution) at −50° C.

Final Step (Example 18)

Obtained analogously to example 1 by starting from 6-chloromethyl-5-methyl-[1,2,5]oxadiazolo[3,4-b]pyridin-7-ylamine C and (2,3-dihydro-)[1,4]dioxino[2,3-b]pyridine-6-yl)-magnesium chloride 18.1. When complete conversion is observed by HPLC-MS, the reaction mixture concentrated under reduced pressure and the residue is purified by silica gel chromatography (eluent: petroleum ether/ethyl acetate 38/62→0/100). The residue is dissolved in methanol, concentrated under reduced pressure and purified by RP-HPLC (modifier: ammonium hydroxide).

Yield: 30% of theory

Mass spectrometry (ESI$^+$): m/z=300 [M+H]$^+$

HPLC (Method 10): Retention time=0.63 min.

Example 19

6-(5-Brom32.2-chloro-pyridin-2-ylmethyl)-5-methyl-[1,2,5]oxadiazolo[3,4-b]pyridin-7-ylamine

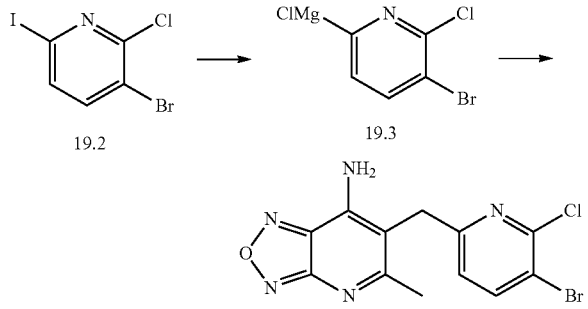

19.3 (5-bromo-6-chloro-2-pyridyl)-magnesium Chloride

Analogously to example 1.1 obtained by starting from 3-bromo-2-chloro-6-iodo-pyridine 19.2 and isopropylmagnesium chloride lithiumchloride complex (1.3 M solution) at −65° C.

Final Step (Example 19)

Obtained analogously to example 1 by reacting 6-chloromethyl-5-methyl-[1,2,5]oxadiazolo-[3,4-b]pyridin-7-ylamine C with (5-bromo-6-chloro-2-pyridyl)-magnesium chloride 19.3 at −55° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 10% of theory

Mass spectrometry (ESI$^+$): m/z=354, 356 [M+H]$^+$

HPLC (Method 4): Retention time=0.90 min.

Example 20

6-(4-Chloro-5-trifluoromethyl-pyridin-2-ylmethyl)-5-methyl-[1,2,5]oxadiazolo[3,4-b]pyridin-7-ylamine

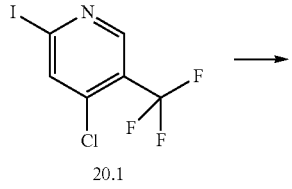

-continued

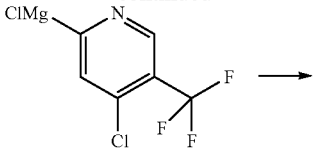

20.2

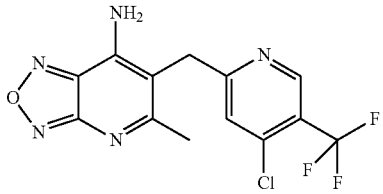

ex. 20

20.2 [4-chloro-5-(trifluoromethyl)-2-pyridyl]-magnesium Chloride

Analogously to example 1.1 obtained by starting from 4-chloro-2-iodo-5-trifluoromethyl-pyridine 20.1 and isopropylmagnesium chloride lithiumchloride complex (1.3 M solution) at −55° C.

Final Step (Example 20)

Obtained analogously to example 1 by reacting 6-chloromethyl-5-methyl-[1,2,5]oxadiazolo-[3,4-b]pyridin-7-ylamine C with [4-chloro-5-(trifluoromethyl)-2-pyridyl]-magnesium chloride 20.2 at −55° C. When complete conversion is observed by HPLC-MS the reaction mixture is diluted with methanol, concentrated under reduced pressure and purified by RP-HPLC (modifier: ammonium hydroxide).

Yield: 24% of theory

Mass spectrometry (ESI$^+$): m/z=344 $[M+H]^+$

HPLC (Method 1): Retention time=0.95 min.

Example 21

6-(5,6-Dibromo-pyridin-2-ylmethyl)-5-methyl-[1,2,5]oxadiazolo[3,4-b]pyridin-7-ylamine

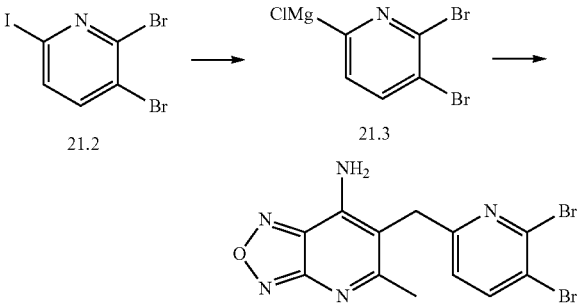

21.2

21.3

Ex. 21

21.3 (5,6-dibromo-2-pyridyl)-magnesium Chloride

Analogously to example 1.1, obtained by starting from 2,3-dibromo-6-iodo-pyridine 21.2 and isopropylmagnesium chloride lithiumchloride complex (1.3 M solution) at −65° C.

Final Step (Example 21)

Obtained analogously to example 1 by reacting 6-chloromethyl-5-methyl-[1,2,5]oxadiazolo-[3,4-b]pyridin-7-ylamine C with (5,6-dibromo-2-pyridyl)-magnesium chloride 21.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by silica gel chromatography (eluent: cyclohexane/ethyl acetate 100/0->50/50).

Yield: 8% of theory

Mass spectrometry (ESI$^+$): m/z=397, 399, 401 $[M+H]^+$

HPLC (Method 4): Retention time=0.91 min.

Example 22

6-(5-Brom32.2-fluoro-pyridin-2-ylmethyl)-5-methyl-[1,2,5]oxadiazolo[3,4-b]pyridin-7-ylamine

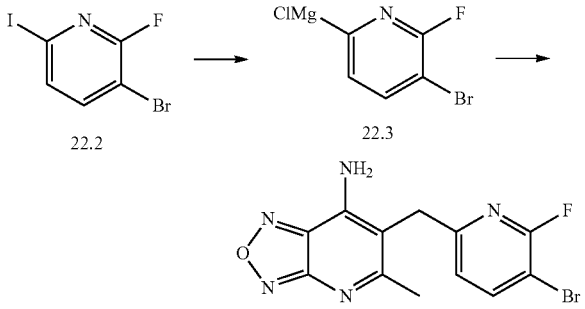

22.2

22.3

Ex. 22

22.3 (5-bromo-6-fluoro-2-pyridyl)-magnesium Chloride

Analogously to example 1.1 obtained by starting from 3-bromo-2-fluoro-6-iodo-pyridine 22.2 and isopropylmagnesium chloride lithiumchloride complex (1.3 M solution) at −65° C.

Final Step (Example 22)

Obtained analogously to example 1 by reacting 6-chloromethyl-5-methyl-[1,2,5]oxadiazolo-[3,4-b]pyridin-7-ylamine C with (5-bromo-6-fluoro-2-pyridyl)-magnesium chloride 22.3 at −70° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by silica gel chromatography (eluent: cyclohexane/ethyl acetate 100/0->50/50).

Yield: 69% of theory

Mass spectrometry (ESI+): m/z=338, 340 $[M+H]^+$

HPLC (Method 4): Retention time=0.84 min.

Example 23

6-(5-Brom32.2-difluoromethoxy-pyridin-2-ylmethyl)-5-methyl-[1,2,5]oxadiazolo[3,4-b]pyridin-7-ylamine

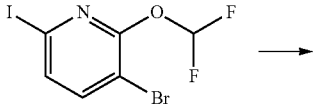

23.3

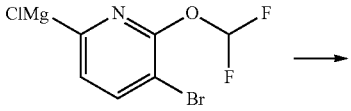

23.4

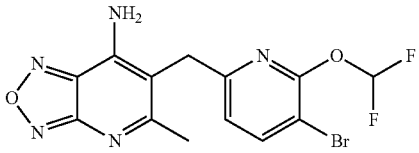

Ex. 23

23.4 [5-bromo-6-(difluoromethoxy)-2-pyridyl]-magnesium Chloride

Analogously to example 1.1 obtained by starting from 3-bromo-2-difluoromethoxy-6-iodo-pyridine 23.3 and isopropylmagnesium chloride lithiumchloride complex (1.3 M solution) at −65° C.

Final Step (Example 23)

Obtained analogously to example 1 by reacting 6-chloromethyl-5-methyl-[1,2,5]oxadiazolo-[3,4-b]pyridin-7-ylamine C with [5-bromo-6-(difluoromethoxy)-2-pyridyl]-magnesium chloride 23.4 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 76% of theory

Mass spectrometry (ESI+): m/z=386, 388 $[M+H]^+$

HPLC (Method 1): Retention time=0.97 min.

Example 24

6-(7-Amino-5-methyl-[1,2,5]oxadiazolo[3,4-b]pyridin-6-ylmethyl)-2-chloro-nicotinonitrile

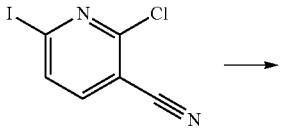

24.3

-continued

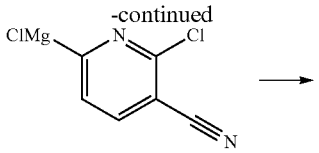

24.4

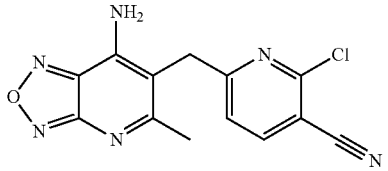

Ex. 24

24.4 (6-chloro-5-cyano-2-pyridyl)-magnesium Chloride

Analogously to example 1.1 obtained by starting from 2-Chloro-6-iodo-nicotinonitrile 24.3 and isopropylmagnesium chloride lithiumchloride complex (1.3 M solution) at −65° C.

Final Step (Example 24)

Obtained analogously to example 1 by reacting 6-chloromethyl-5-methyl-[1,2,5]oxadiazolo-[3,4-b]pyridin-7-ylamine C with (6-chloro-5-cyano-2-pyridyl)-magnesium chloride 24.4 at −70° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by silica gel chromatography (eluent: cyclohexane/ethyl acetate 100/0->50/50).

Yield: 84% of theory

Mass spectrometry (ESI+): m/z=301 $[M+H]^+$

HPLC (Method 4): Retention time=0.79 min.

Example 25

6-(7-Amino-5-methyl-[1,2,5]oxadiazolo[3,4-b]pyridin-6-ylmethyl)-3-fluoro-pyridine-2-carbonitrile

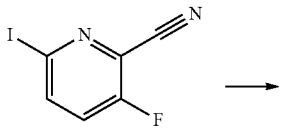

25.3

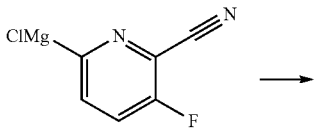

25.4

-continued

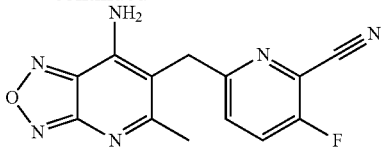

Ex. 25

25.4 (6-cyano-5-fluoro-2-pyridyl)-magnesium Chloride

Analogously to example 1.1 obtained by starting from 3-Fluoro-6-iodo-pyridine-2-carbonitrile 25.3 and isopropylmagnesium chloride lithiumchloride complex (1.3 M solution) at −65° C.

Final Step (Example 25)

Obtained analogously to example 1 by reacting 6-chloromethyl-5-methyl-[1,2,5]oxadiazolo-[3,4-b]pyridin-7-ylamine C with (6-cyano-5-fluoro-2-pyridyl)-magnesium chloride 25.4 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by silica gel chromatography (eluent: cyclohexane/ethyl acetate 100/0->50/50).

Yield: 75% of theory

Mass spectrometry (ESI$^+$): m/z=285 $[M+H]^+$

HPLC (Method 1): Retention time=0.83 min.

Example 26

5-Methyl-6-(4-trifluoromethyl-pyridin-2-ylmethyl)-[1,2,5]oxadiazolo[3,4-b]pyridin-7-ylamine

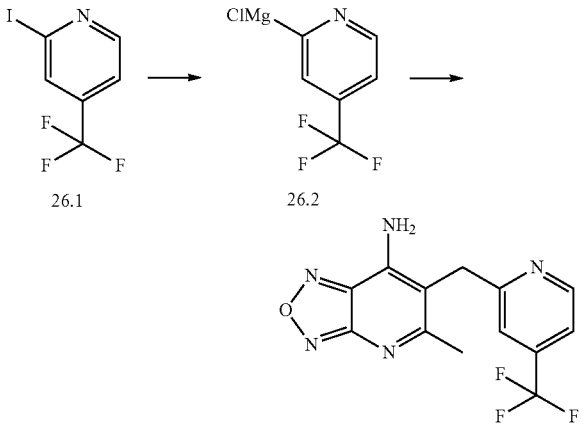

26.1 26.2 ex. 26

26.2 [4-(trifluoromethyl)-2-pyridyl]-magnesium Chloride

Analogously to example 1.1 obtained by starting from 2-iodo-4-trifluoromethyl-pyridine 26.1 and isopropylmagnesium chloride lithiumchloride complex (1.3 M solution) at −55° C.

Final Step (Example 26)

Obtained analogously to example 1 by reacting 6-chloromethyl-5-methyl-[1,2,5]oxadiazolo-[3,4-b]pyridin-7-ylamine C with [4-(trifluoromethyl)-2-pyridyl]-magnesium chloride 26.2. at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 50% of theory

Mass spectrometry (ESI$^+$): m/z=310 $[M+H]^+$

HPLC (Method 1): Retention time=0.89 min.

Example 27

2-(7-Amino-5-methyl-[1,2,5]oxadiazolo[3,4-b]pyridin-6-ylmethyl)-5-bromo-isonicotinonitrile

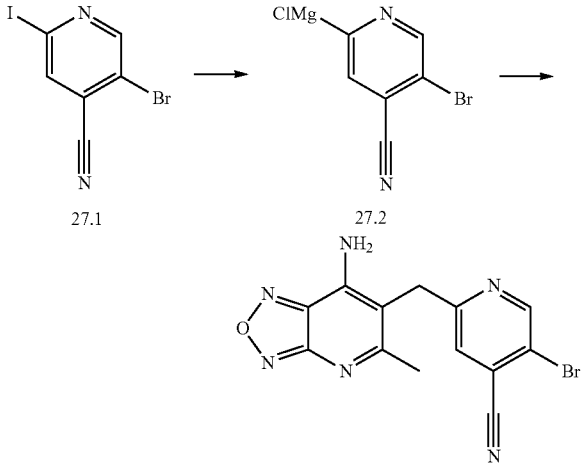

27.1 27.2 ex. 27

27.2 (5-bromo-4-cyano-2-pyridyl)-magnesium Chloride

Analogously to example 1.1 obtained by starting from 5-bromo-2-iodo-isonicotinonitrile 27.1 and isopropylmagnesium chloride lithiumchloride complex (1.3 M solution) at −65° C.

Final Step (Example 27)

Obtained analogously to example 1 by reacting 6-chloromethyl-5-methyl-[1,2,5]oxadiazolo-[3,4-b]pyridin-7-ylamine C with (5-bromo-4-cyano-2-pyridyl)-magnesium chloride 27.2 at −60° C. When complete conversion is observed by HPLC-MS the reaction mixture is diluted with methanol, concentrated under reduced pressure and purified by RP-HPLC (modifier: ammonium hydroxide).

Yield: 4% of theory

Mass spectrometry (ESI$^+$): m/z=344, 346 $[M+H]^+$

HPLC (Method 1): Retention time=0.84 min.

Example 28

2-(7-Amino-5-methyl-[1,2,5]oxadiazolo[3,4-b]pyridin-6-ylmethyl)-isonicotinonitrile

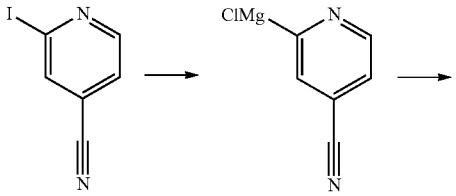

28.1 28.2

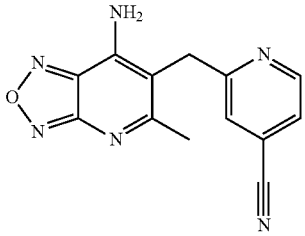

Ex. 28

28.2 (4-cyano-2-pyridyl)-magnesium Chloride

Analogously to example 1.1 obtained by starting from 2-iodo-isonicotinonitrile 28.1 and isopropylmagnesium chloride lithiumchloride complex (1.3 M solution) at −65° C.

Final Step (Example 28)

Obtained analogously to example 1 by reacting 6-chloromethyl-5-methyl-[1,2,5]oxadiazolo-[3,4-b]pyridin-7-ylamine C with (4-cyano-2-pyridyl)-magnesium chloride 28.2 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 46 mg (34% of theory)

Mass spectrometry (ESI$^+$): m/z=267 $[M+H]^+$

HPLC (Method 1): Retention time=0.74 min.

Example 29

2-(7-Amino-5-methyl-[1,2,5]oxadiazolo[3,4-b]pyridin-6-ylmethyl)-isonicotinamide

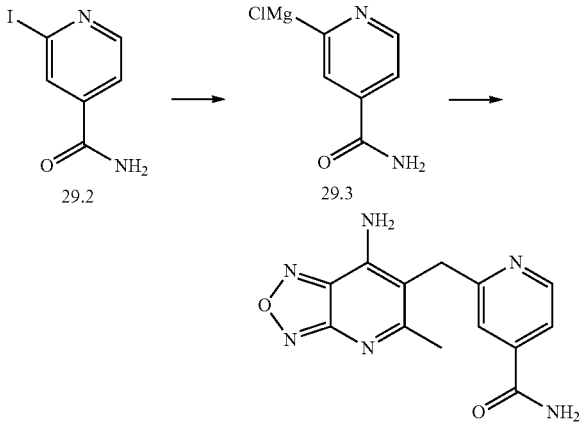

29.2 29.3

Ex. 29

29.3 (4-carbamoyl-2-pyridyl)-magnesium Chloride

Analogously to example 1.1 obtained by starting from 2-iodo-isonicotinamide 29.2 and isopropylmagnesium chloride lithiumchloride complex (1.3 M solution) at −70° C.

Final Step (Example 29)

Obtained analogously to example 1 by reacting 6-chloromethyl-5-methyl-[1,2,5]oxadiazolo-[3,4-b]pyridin-7-ylamine C with (4-carbamoyl-2-pyridyl)-magnesium chloride 29.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 48% of theory

Mass spectrometry (ESI$^+$): m/z=285 $[M+H]^+$

HPLC (Method 1): Retention time=0.62 min.

Example 30

6-(5-Chloro-pyrimidin-2-ylmethyl)-5-methyl-[1,2,5]oxadiazolo[3,4-b]pyridin-7-ylamine

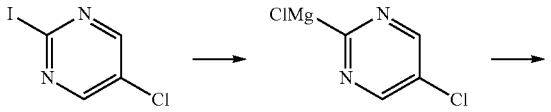

30.1

-continued

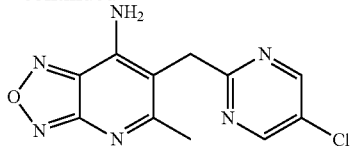

Ex. 30

30.1 (5-chloropyrimidin-2-yl)-magnesium Chloride

Analogously to example 1.1 obtained by starting from 5-chloro-2-iodo-pyrimidine (from Activate) and isopropylmagnesium chloride lithiumchloride complex (1.3 M solution) at −65° C.

Final Step (Example 30)

Obtained analogously to example 1 by reacting 6-chloromethyl-5-methyl-[1,2,5]oxadiazolo-[3,4-b]pyridin-7-ylamine C with (5-chloropyrimidin-2-yl)-magnesium chloride 30.1 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 32% of theory

Mass spectrometry (ESI$^+$): m/z=277 [M+H]$^+$

HPLC (Method 1): Retention time=0.79 min.

Example 31

6-(5-Bromo-pyrimidin-2-ylmethyl)-5-methyl-[1,2,5]oxadiazolo[3,4-b]pyridin-7-ylamine

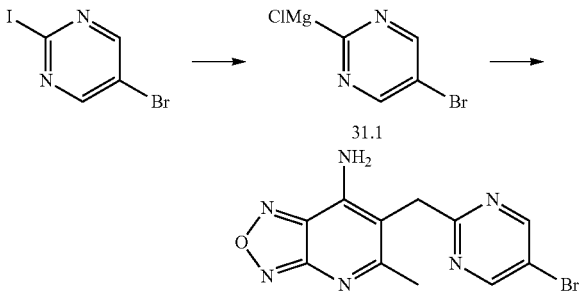

Ex. 31

31.1 (5-bromopyrimidin-2-yl)-magnesium Chloride

Analogously to example 1.1 obtained by starting from 5-bromo-2-iodo-pyrimidine (from Aldrich) and isopropylmagnesium chloride lithiumchloride complex (1.3 M solution) at −45° C.

Final Step (Example 31)

Obtained analogously to example 1 by reacting 6-chloromethyl-5-methyl-[1,2,5]oxadiazolo-[3,4-b]pyridin-7-ylamine C with (5-bromopyrimidin-2-yl)-magnesium chloride 31.1 at −65° C.

When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: trifluoroacetic acid).

Yield: 0.03 g (14% of theory)

Mass spectrometry (ESI$^+$): m/z=320, 322 [M+H]$^+$

HPLC (Method 1): Retention time=0.82 min.

Example 32

6-(5-Bromo-4-trifluoromethyl-pyridin-2-ylmethyl)-5-methyl-[1,2,5]oxadiazolo[3,4-b]pyridin-7-ylamine

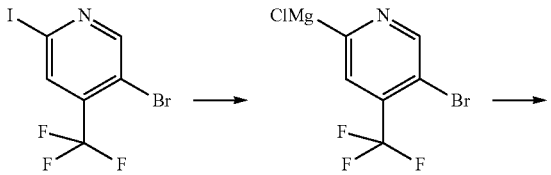

32.2 32.2

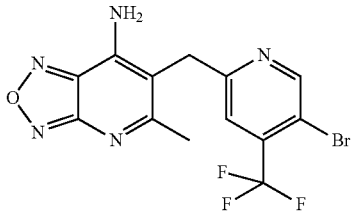

Ex. 32

32.3 [5-bromo-4-(trifluoromethyl)-2-pyridyl]-magnesium Chloride

Analogously to example 1.1 obtained by starting from 5-Bromo-2-iodo-4-trifluoromethyl-pyridine 32.2 and isopropylmagnesium chloride lithiumchloride complex (1.3 M solution) at −65° C.

Final Step (Example 32)

Obtained analogously to example 1 by reacting 6-chloromethyl-5-methyl-[1,2,5]oxadiazolo-[3,4-b]pyridin-7-ylamine C with [5-bromo-4-(trifluoromethyl)-2-pyridyl]-magnesium chloride 32.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: ammonium hydroxide).

Yield: 23% of theory

Mass spectrometry (ESI$^+$): m/z=387, 389 [M+H]$^+$

HPLC (Method 1): Retention time=0.98 min.

Example 33

6-(7-Amino-5-methyl-[1,2,5]oxadiazolo[3,4-b]pyridin-6-ylmethyl)-3-trifluoromethoxy-pyridine-2-carbonitrile

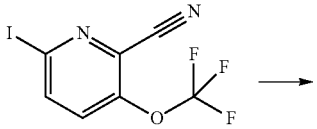

33.3

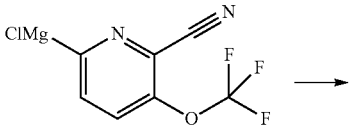

33.4

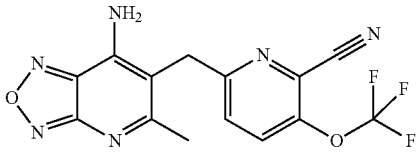

Ex. 33

33.4 [6-cyano-5-(trifluoromethoxy)-2-pyridyl]-magnesium Chloride

Analogously to example 1.1 obtained by starting from 6-Iodo-3-trifluoromethoxy-pyridine-2-carbonitrile 33.3 and isopropylmagnesium chloride lithiumchloride complex (1.3 M solution) at −70° C.

Final Step (Example 33)

Obtained analogously to example 1 by reacting 6-chloromethyl-5-methyl-[1,2,5]oxadiazolo[3,4-b]pyridin-7-ylamine C with [6-cyano-5-(trifluoromethoxy)-2-pyridyl]-magnesium chloride 33.4. at −70° C. When complete conversion is observed by HPLC-MS the reaction mixture is diluted with methanol, concentrated under reduced pressure and purified by silica gel chromatography (eluent: cyclohexane/ethyl acetate 0%→40%).

Yield: 62% of theory

Mass spectrometry (ESI$^+$): m/z=351 $[M+H]^+$

HPLC (Method 1): Retention time=0.91 min.

Example 34

5-Methyl-6-(4-trifluoromethyl-pyrimidin-2-ylmethyl)-[1,2,5]oxadiazolo[3,4-b]pyridin-7-ylamine

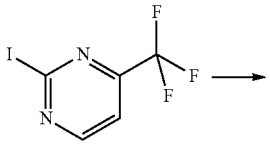

34.1

-continued

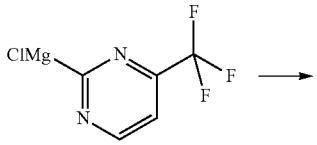

34.2

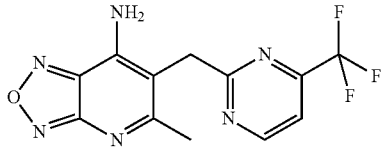

Ex. 34

34.2 [4-(trifluoromethyl)pyrimidin-2-yl]-magnesium Chloride

Analogously to example 1.1 obtained by starting from 2-Iodo-4-trifluoromethyl-pyrimidine 34.1 and isopropylmagnesium chloride lithiumchloride complex (1.3 M solution) at −55° C.

Final Step (Example 34)

Obtained analogously to example 1 by reacting 6-chloromethyl-5-methyl-[1,2,5]oxadiazolo-[3,4-b]pyridin-7-ylamine C with [4-(trifluoromethyl)pyrimidin-2-yl]-magnesium chloride 34.2 at −70° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by silica gel chromatography (eluent: cyclohexane/ethyl acetate 0%→50%).

Yield: 35% of theory

Mass spectrometry (ESI$^+$): m/z=311 $[M+H]^+$

HPLC (Method 1): Retention time=0.81 min.

Example 35

5-methyl-6-[5-(trifluoromethyl)pyrimidin-2-yl]methyl-[1,2,5]oxadiazolo[3,4-b]pyridin-7-amine

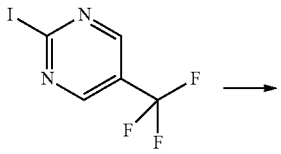

35.1

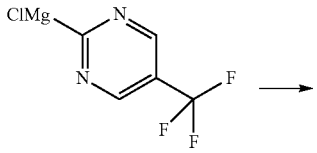

35.2

-continued

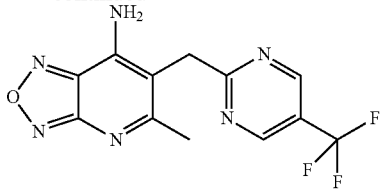

Ex. 35

35.2
2-(chloromagnesio)-5-(trifluoromethyl)pyrimidine

Analogously to example 1.1, obtained by starting from 2-iodo-5-(trifluoromethyl)pyrimidine 35.1 and isopropylmagnesium chloride lithiumchloride complex (1.3 M solution) at −65° C.

Final Step (Example 35)

Obtained analogously to example 1 by reacting 6-chloromethyl-5-methyl-[1,2,5]oxadiazolo-[3,4-b]pyridin-7-ylamine C with 2-(chloromagnesio)-5-(trifluoromethyl)pyrimidine 35.2 at −70° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by chromatography on silica gel (using a solvent gradient from cyclohexane/ethyl acetate 100/0 to 50/50).

Yield: 9% of theory

Mass spectrometry (ESI$^+$): m/z=311 $[M+H]^+$

HPLC (Method 1): Retention time=0.83 min.

Example 36

6-(7-amino-5-methyl-[1,2,5]oxadiazolo[3,4-b]pyridin-6-ylmethyl)-4-(trifluoromethyl)pyridine-2-carbonitrile

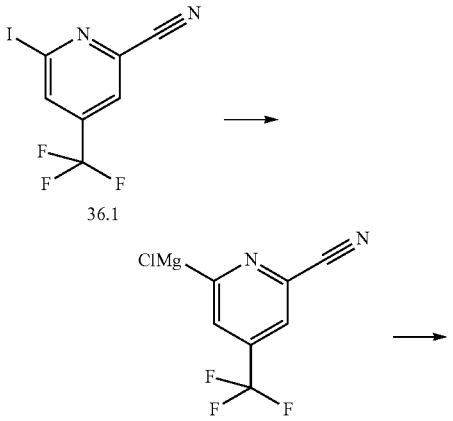

36.1

36.2

-continued

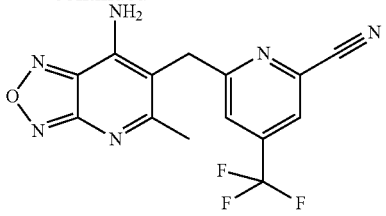

Ex. 36

36.2 6-(chloromagnesio)-4-(trifluoromethyl)pyridine-2-carbonitrile

Analogously to example 1.1, obtained by starting from 6-iodo-4-(trifluoromethyl)pyridine-2-carbonitrile 36.1 and isopropylmagnesium chloride lithiumchloride complex (1.3 M solution) at −70° C.

Final Step (Example 36)

Obtained analogously to example 1 by reacting 6-chloromethyl-5-methyl-[1,2,5]oxadiazolo-[3,4-b]pyridin-7-ylamine C with 6-(chloromagnesio)-4-(trifluoromethyl)pyridine-2-carbonitrile 36.2 at −70° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by chromatography on silica gel (using a solvent gradient from cyclohexane/ethyl acetate 100/0 to 50/50).

Yield: 48% of theory

Mass spectrometry (ESI$^+$): m/z=335 $[M+H]^+$

HPLC (Method 1): Retention time=0.90 min.

Example 37

6-(7-amino-5-methyl-[1,2,5]oxadiazolo[3,4-b]pyridin-6-ylmethyl)-4-(trifluoromethyl)pyridine-2-carbonitrile

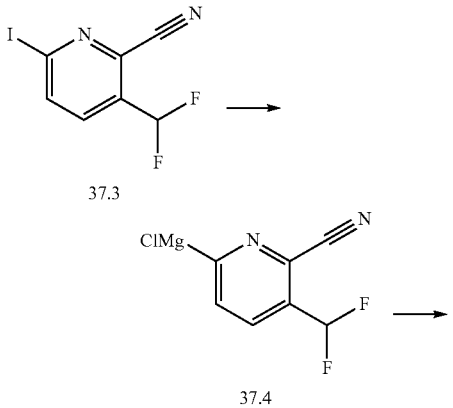

37.3

37.4

-continued

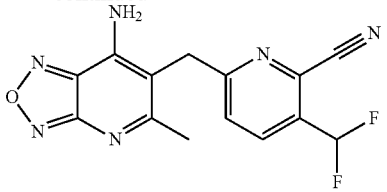

Ex. 37

37.4 6-(chloromagnesio)-3-(difluoromethyl)pyridine-2-carbonitrile

Analogously to example 1.1 obtained by starting from 3-(difluoromethyl)-6-iodopyridine-2-carbonitrile 37.3 and isopropylmagnesium chloride lithiumchloride complex (1.3 M solution) at −70° C.

Final Step (Example 37)

Obtained analogously to example 1 by reacting 6-chloromethyl-5-methyl-[1,2,5]oxadiazolo-[3,4-b]pyridin-7-ylamine C and 6-(chloromagnesio)-3-(difluoromethyl)pyridine-2-carbonitrile 37.4 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by chromatography on silica gel (using a solvent gradient from cyclohexane/ethyl acetate 100/0 to 50/50).

Yield: 32% of theory

Mass spectrometry (ESI$^+$): m/z=317 $[M+H]^+$

HPLC (Method 1): Retention time=0.86 min.

Example 38

6-(7-amino-5-methyl-[1,2,5]oxadiazolo[3,4-b]pyridin-6-ylmethyl)-4-chloropyridine-2-carbonitrile

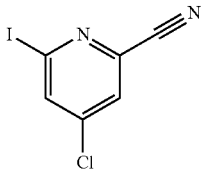

38.1

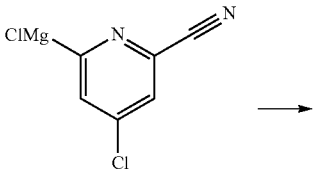

38.2

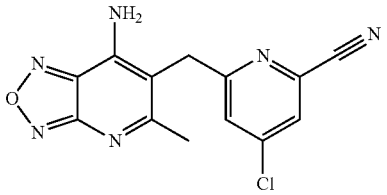

Ex. 38

38.2 4-chloro-6-(chloromagnesio)pyridine-2-carbonitrile

Analogously to example 1.1 obtained by starting from 4-chloro-6-iodopyridine-2-carbonitrile 38.1 and isopropylmagnesium chloride lithiumchloride complex (1.3 M solution) at −70° C.

Final Step (Example 38)

Obtained analogously to example 1 by reacting 6-chloromethyl-5-methyl-[1,2,5]oxadiazolo-[3,4-b]pyridin-7-ylamine C with 4-chloro-6-(chloromagnesio)pyridine-2-carbonitrile 38.2 at −70° C. When complete conversion is observed by HPLC-MS the reaction mixture is diluted with methanol, concentrated under reduced pressure and purified by chromatography on silica gel (using a solvent gradient from cyclohexane/ethyl acetate 100/0 to 50/50).

Yield: 26% of theory

Mass spectrometry (ESI$^+$): m/z=301 $[M+H]^+$

HPLC (Method 1): Retention time=0.84 min.

Example 39

6-[(5-cyclopropylpyridin-2-yl)methyl]-5-methyl-[1,2,5]oxadiazolo[3,4-b]pyridin-7-amine

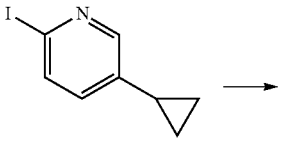

39.1

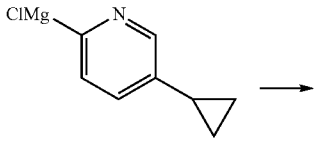

39.2

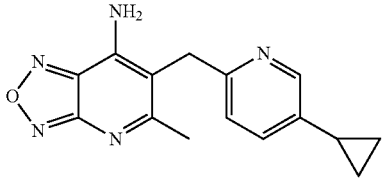

Ex. 39

39.2 2-(chloromagnesio)-5-cyclopropylpyridine

Analogously to example 1.1 obtained by starting from 5-cyclopropyl-2-iodopyridine 39.1 and isopropylmagnesium chloride lithiumchloride complex (1.3 M solution) at −70° C.

Final Step (Example 39)

Obtained analogously to example 1 by reacting 6-chloromethyl-5-methyl-[1,2,5]oxadiazolo-[3,4-b]pyridin-7-ylamine C and 2-(chloromagnesio)-5-cyclopropylpyridine 39.2 at −65° C.

When complete conversion is observed by HPLC-MS the reaction mixture is diluted with methanol, concentrated under reduced pressure and purified by RP-HPLC (modifier: ammonium hydroxide).

Yield: 18% of theory

Mass spectrometry (ESI$^+$): m/z=282 [M+H]$^+$

HPLC (Method 1): Retention time=0.89 min.

Example 40

6-[(5-cyclopropylpyridin-2-yl)methyl]-5-methyl-[1,2,5]oxadiazolo[3,4-b]pyridin-7-amine

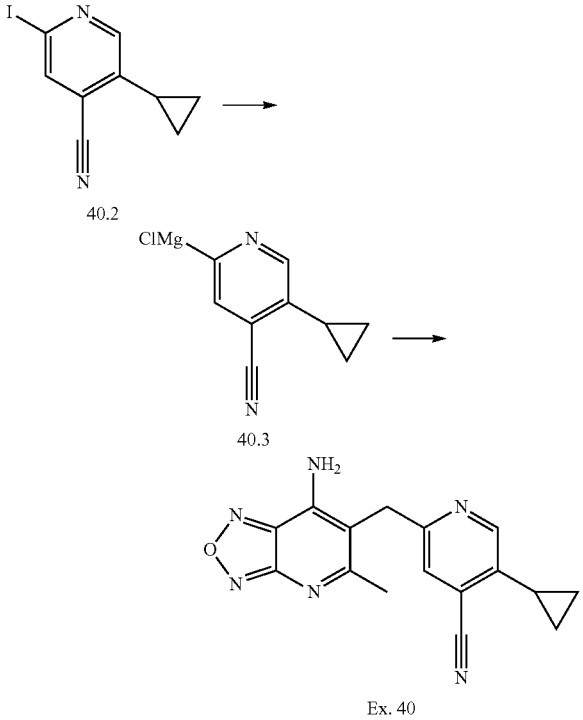

40.3 2-(chloromagnesio)-5-cyclopropylpyridine-4-carbonitrile

Analogously to example 1.1 obtained by starting from 5-cyclopropyl-2-iodopyridine-4-carbonitrile 40.2 and isopropylmagnesium chloride lithiumchloride complex (1.3 M solution) at −70° C.

Final Step (Example 40)

Obtained analogously to example 1 by reacting 6-chloromethyl-5-methyl-[1,2,5]oxadiazolo-[3,4-b]pyridin-7-ylamine C with 2-(chloromagnesio)-5-cyclopropylpyridine-4-carbonitrile 40.3 at −65° C. When complete conversion is observed by HPLC-MS the reaction mixture is diluted with methanol, concentrated under reduced pressure and purified by RP-HPLC (modifier: ammonium hydroxide). The residue is purified by flash column chromatography on silica gel (using a solvent gradient from dichloromethane/methanol 99/1 to 86/14).

Yield: 5% of theory

Mass spectrometry (ESI$^+$): m/z=307 [M+H]$^+$

HPLC (Method 2): Retention time=0.76 min.

Example 41

6-[(5-cyclopropoxypyridin-2-yl)methyl]-5-methyl-[1,2,5]oxadiazolo[3,4-b]pyridin-7-amine

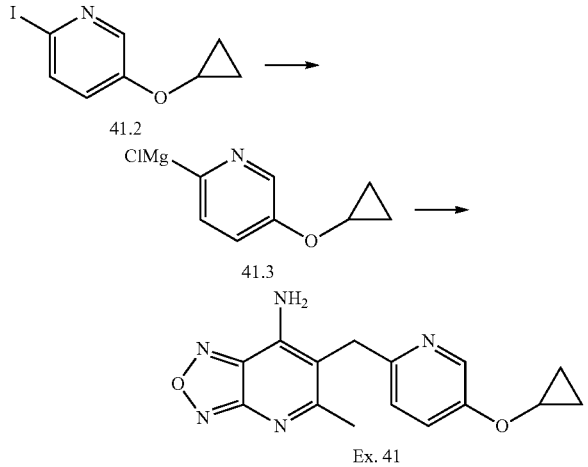

41.3 2-(chloromagnesio)-5-cyclopropoxypyridine

Analogously to example 1.1 obtained by starting from 5-cyclopropoxy-2-iodopyridine 41.2 and isopropylmagnesium chloride lithiumchloride complex (1.3 M solution) at −70° C.

Final Step (Example 41)

Obtained analogously to example 1 by reacting 6-chloromethyl-5-methyl-[1,2,5]oxadiazolo-[3,4-b]pyridin-7-ylamine C with 2-(chloromagnesio)-5-cyclopropoxypyridine 41.3 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by chromatography on silica gel (using a solvent gradient from petrolether/ethyl acetate 88/12 to 0/100).

Yield: 3% of theory

Mass spectrometry (ESI$^+$): m/z=298 [M+H]$^+$

HPLC (Method 1): Retention time=0.88 min.

Example 42

6-(7-amino-5-methyl-[1,2,5]oxadiazolo[3,4-b]pyridin-6-yl methyl)-3-cyclopropylpyridine-2-carbonitrile

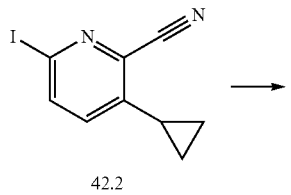

-continued

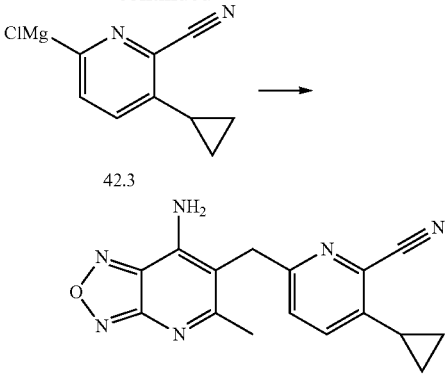

42.3

Ex. 42

42.3 6-(chloromagnesio)-3-cyclopropylpyridine-2-carbonitrile

Analogously to example 1.1 obtained by starting from 3-cyclopropyl-6-iodopyridine-2-carbonitrile 42.2 and isopropylmagnesium chloride lithiumchloride complex (1.3 M solution) at −70° C.

Final Step (Example 42)

Obtained analogously to example 1 by reacting 6-chloromethyl-5-methyl-[1,2,5]oxadiazolo-[3,4-b]pyridin-7-ylamine C and 6-(chloromagnesio)-3-cyclopropylpyridine-2-carbonitrile 42.3 at −75° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by chromatography on silica gel (using a solvent gradient from dichloromethane/methanol 88/12 to 0/100).

Yield: 38% of theory

Mass spectrometry (ESI$^+$): m/z=307 $[M+H]^+$

HPLC (Method 1): Retention time=0.90 min.

Example 43

6-(7-amino-5-methyl-[1,2,5]oxadiazolo[3,4-b]pyridin-6-ylmethyl)-2-cyclopropylpyridine-3-carbonitrile

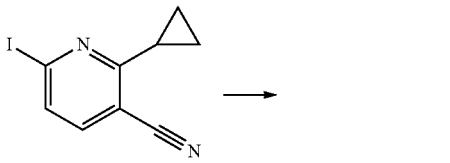

43.3

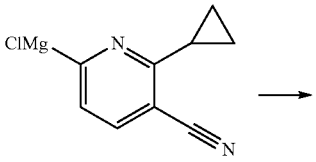

43.4

-continued

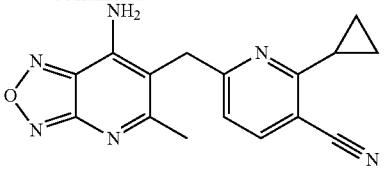

Ex. 43

43.4 6-(chloromagnesio)-2-cyclopropylpyridine-3-carbonitrile

Analogously to example 1.1 obtained by starting from 2-cyclopropyl-6-iodopyridine-3-carbonitrile 43.3 and isopropylmagnesium chloride lithiumchloride complex (1.3 M solution) at −70° C.

Final Step (Example 43)

Obtained analogously to example 1 by reacting 6-(bromomethyl)-5-methyl-[1,2,5]oxadiazolo[3,4-b]pyridin-7-amine hydrobromide D with 6-(chloromagnesio)-2-cyclopropylpyridine-3-carbonitrile 43.4 at −65° C. When complete conversion is observed by HPLC-MS the reaction mixture is partitioned between with ethyl acetate and a half saturated aqueous solution of sodium bicarbonate. The phases are separated and the aqueous phase is extracted with ethyl acetate. The organic phase is dried, concentrated and purified by RP-HPLC (modifier: trifluoroacetic acid).

Yield: 9% of theory

Mass spectrometry (ESI$^+$): m/z=307 $[M+H]^+$

HPLC (Method 2): Retention time=0.81 min.

Example 44

5-Methyl-6-(5-methylsulfanyl-pyridin-2-ylmethyl)-[1,2,5]oxadiazolo[3,4-b]pyridin-7-ylamine

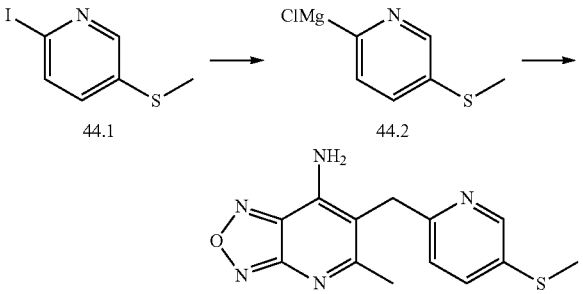

44.1

44.2

Ex. 44

44.2 (5-methylsulfanyl-2-pyridyl)-magnesium Chloride

Analogously to example 1.1 obtained by starting from 2-iodo-5-methylsulfanyl-pyridine 44.1 and isopropylmagnesium chloride lithiumchloride complex (1.3 M solution) at −60° C.

Final Step (Example 44)

Obtained analogously to example 1 by reacting 6-chloromethyl-5-methyl-[1,2,5]oxadiazolo-[3,4-b]pyridin-7-ylamine C and (5-methylsulfanyl-2-pyridyl)-magnesium chloride 44.2 at −65° C. When complete conversion is observed by HPLC-MS the reaction mixture is diluted with methanol, concentrated under reduced pressure and purified by silica gel chromatography (eluent: cyclohexane/ethyl acetate 0%→80%).

Yield: 11% of theory

Mass spectrometry (ESI$^+$): m/z=288 $[M+H]^+$

HPLC (Method 3): Retention time=0.80 min.

Example 45

4-amino-2-(7-amino-5-methyl-[1,2,5]oxadiazolo[3,4-b]pyridin-6-ylmethyl)pyrimidine-5-carbonitrile

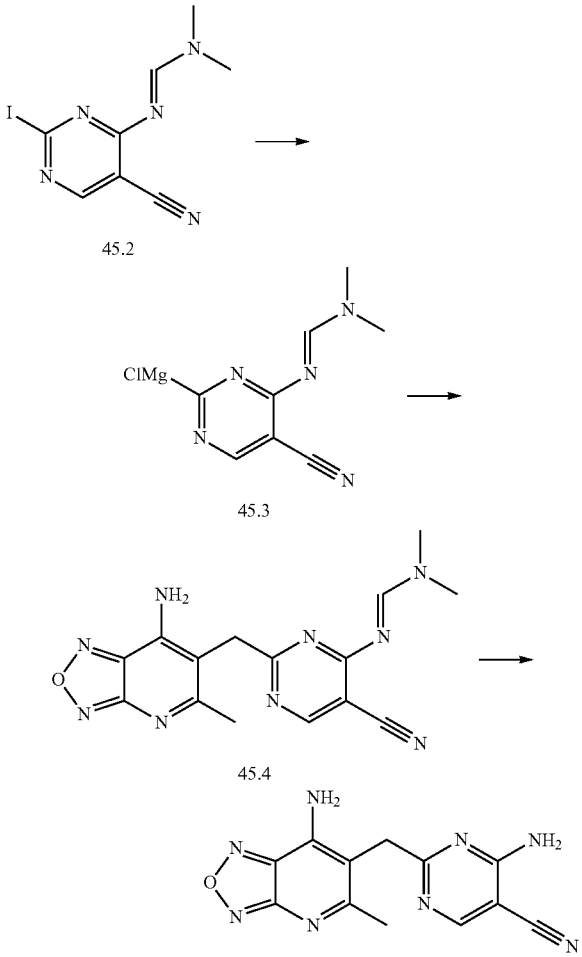

45.3 (E)-N'-[2-(chloromagnesio)-5-cyanopyrimidin-4-yl]-N,N-dimethylmethanimidamide Analogously to example 1.1, obtained by starting from (E)-N'-(5-cyano-2-iodopyrimidin-4-yl)-N,N-dimethylmethanimidamide 45.2 and isopropylmagnesium chloride lithiumchloride complex (1.3 M solution) at −70° C.

45.4 (E)-N'-[2-({7-amino-5-methyl-[1,2,5]oxadiazolo[3,4-b]pyridin-6-yl}methyl)-5-cyanopyrimidin-4-yl]-N,N-dimethylmethanimidamide Obtained analogously to example 1 by reacting 6-chloromethyl-5-methyl-[1,2,5]oxadiazolo-[3,4-b]pyridin-7-ylamine C with (E)-N'-[2-(chloromagnesio)-5-cyanopyrimidin-4-yl]-N,N-dimethylmethanimidamide 45.3 at −65° C. When complete conversion is observed by HPLC-MS the reaction mixture is diluted with methanol, concentrated under reduced pressure and purified by RP-HPLC (modifier: ammonium hydroxide).

Yield: 13% of theory

Mass spectrometry (ESI$^+$): m/z=338 $[M+H]^+$

HPLC (Method 1): Retention time=0.81 min.

Final Step (Example 45)

(E)-N'-[2-({7-amino-5-methyl-[1,2,5]oxadiazolo[3,4-b]pyridin-6-yl}methyl)-5-cyanopyrimidin-4-yl]-N,N-dimethylmethanimidamide 45.4 (20.0 mg, 0.06 mmol) and 0.2 mL HCl (32% aqueous solution) are dissolved in 2.0 mL methanol and the mixture is stirred for 10 minutes. The mixture is purified by RP-HPLC (modifier: ammonium hydroxide).

Yield: 5.9 mg (35% of theory)

Mass spectrometry (ESI$^+$): m/z=283 $[M+H]^+$

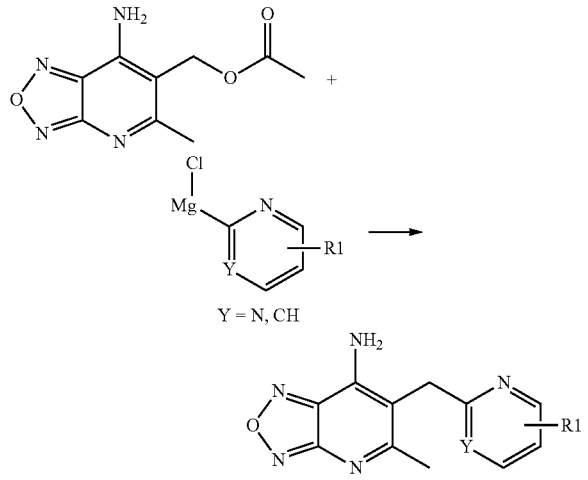

Example 46

2-(7-amino-5-methyl-[1,2,5]oxadiazolo[3,4-b]pyridin-6-ylmethyl)-5-(trifluoromethyl)pyrimidin-4-amine

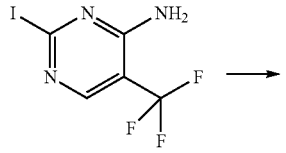

-continued

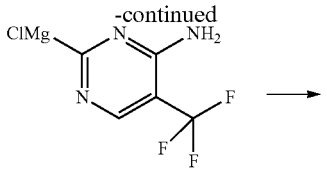

46.4

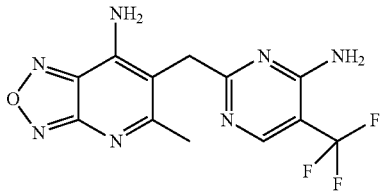

Ex. 46

Solution #1: 2-iodo-5-(trifluoromethyl)pyrimidin-4-amine 46.3 (2.00 g, 6.93 mmol) is dissolved in 30 mL of tetrahydrofuran and the mixture is cooled to −60° C. Isopropylmagnesium chloride lithium complex (1.3 M solution, 11.15 mL, 14.49 mmol) is added dropwise and the mixture is stirred for 20 minutes.

Solution #2: 7-amino-5-methyl-[1,2,5]oxadiazolo[3,4-b] pyridin-6-ylmethyl acetate E (1.40 g, 6.30 mmol) is dissolved in 20 mL of tetrahydrofuran and cooled to −70° C. Copper cyanide lithium chloride complex (1 M solution, 6.62 mL, 6.62 mmol) is added.

Under argon atmosphere solution #1 containing 46.4 is slowly added via cannula to solution #2 keeping the internal temperature below −60° C. Lithium bis(trimethylsilyl)amide (1 M solution in tetrahydrofuran, 6.30 mL, 6.30 mmol) is slowly added at −60° C. and the mixture is warmed to −30° C. The mixture is acidified with 4 M hydrochloric acid, poured into saturated aqueous ammonium chloride/ammonia (9/1 v/v solution) and extracted with ethyl acetate. The combined organic phases are dried and concentrated under reduced pressure. The residue is purified by chromatography on silica gel (using a solvent gradient cyclohexane/ethyl acetate from 100/0 to 40/60).

Yield: 736 mg (36% of theory)

Mass spectrometry (ESI$^+$): m/z=326 $[M+H]^+$

HPLC (Method 1): Retention time=0.80 min.

Example 47

6-(7-amino-5-methyl-[1,2,5]oxadiazolo[3,4-b]pyridin-6-ylmethyl)-3-chloropyridine-2-carbonitrile

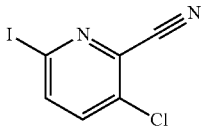

47.1

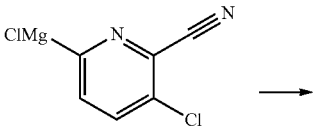

47.2

-continued

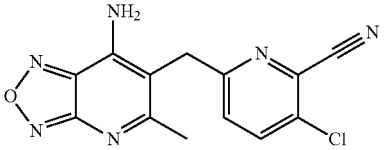

Ex. 47

47.2 3-chloro-6-(chloromagnesio)pyridine-2-carbonitrile

Analogously to example 46 obtained by starting from 3-chloro-6-iodopyridine-2-carbonitrile 47.1 and isopropylmagnesium chloride lithiumchloride complex (1.3 M solution) at −70° C.

Final Step (Example 47)

Analogously to example 46, obtained by starting from 3-chloro-6-(chloromagnesio)pyridine-2-carbonitrile 47.2 and 7-amino-5-methyl-[1,2,5]oxadiazolo[3,4-b]pyridin-6-ylmethyl acetate E. The mixture is purified by flash column chromatography on silica gel (using a solvent gradient cyclohexane/ethyl acetate from 100/0 to 20/80).

Yield: 49% of theory

Mass spectrometry (ESI$^+$): m/z=301 $[M+H]^+$

HPLC (Method 1): Retention time=0.85 min.

Example 48

6-(7-Amino-5-methyl-[1,2,5]oxadiazolo[3,4-b]pyridin-6-ylmethyl)-3-trifluoromethyl-pyridine-2-carbonitrile

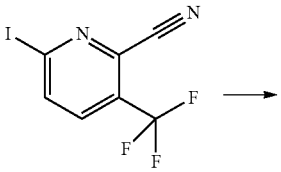

48.3

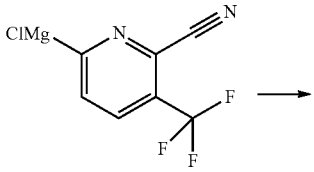

48.4

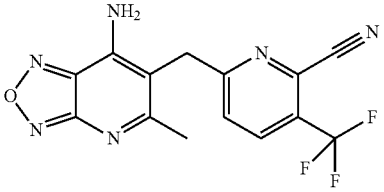

Ex. 48

48.4 6-(chloromagnesio)-3-(trifluoromethyl)pyridine-2-carbonitrile

Analogously to example 46 obtained by starting from 6-Iodo-(3-trifluoromethyl)pyridine-2-carbonitrile 48.3 and isopropylmagnesium chloride lithiumchloride complex (1.3 M solution) at −70° C.

Final Step (Example 48)

Analogously to example 46 obtained by starting from 6-(chloromagnesio)-3-(trifluoromethyl)-pyridine-2-carbonitrile 48.4 and 7-amino-5-methyl-[1,2,5]oxadiazolo-[3,4-b]pyridin-6-ylmethyl acetate E. The mixture is purified by flash column chromatography on silica gel (using a solvent gradient from cyclohexane/ethyl acetate 100/0 to 20/80).

Yield: 73% of theory

Mass spectrometry (ESI$^+$): m/z=335 $[M+H]^+$

HPLC (Method 1): Retention time=0.91 min.

Example 49

1-[6-(7-Amino-5-methyl-[1,2,5]oxadiazolo[3,4-b]pyridin-6-ylmethyl)-3-trifluoromethyl-pyridin-2-yl]-2-methyl-propan-1-one

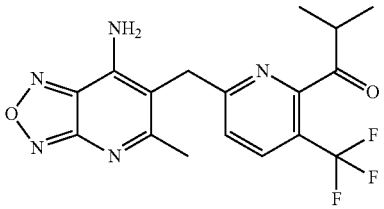

Analogously to example 48 obtained aside from example 48 when 1.5 equivalents of Grignard reagent are used and lithium bis(trimethylsilyl)amide is not added to the reaction mixture. The mixture is purified by RP-HPLC (modifier: ammonium hydroxide).

Yield: 20% of theory

Mass spectrometry (ESI$^+$): m/z=380 $[M+H]^+$

HPLC (Method 1): Retention time=0.93 min.

Example 50

6-[4-chloro-5-(trifluoromethyl)pyrimidin-2-yl]methyl-5-methyl-[1,2,5]oxadiazolo[3,4-b]pyridin-7-amine

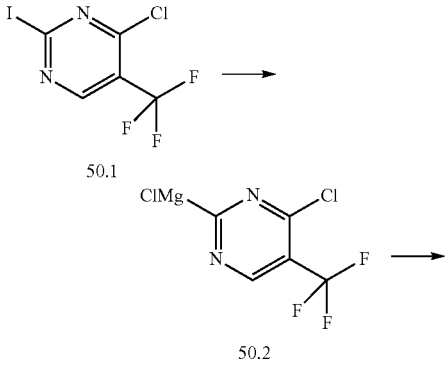

-continued

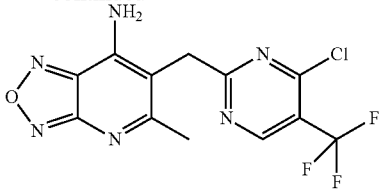

Ex. 50

Analogously to example 46, obtained by starting from 4-chloro-2-iodo-5-(trifluoromethyl)pyrimidine 50.1 and 7-amino-5-methyl-[1,2,5]oxadiazolo[3,4-b]pyridin-6-ylmethyl acetate E. The mixture is purified by RP-HPLC (modifier: ammonium hydroxide)

Yield: 6% of theory

Mass spectrometry (ESI$^+$): m/z=345 $[M+H]^+$

HPLC (Method 1): Retention time=0.94 min.

Example 51

2-(7-amino-5-methyl-[1,2,5]oxadiazolo[3,4-b]pyridin-6-ylmethyl)pyrimidine-4-carbonitrile

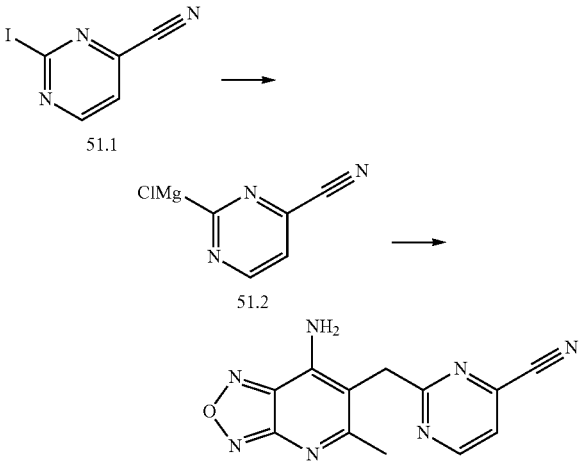

Ex. 51

Analogously to example 46, obtained by starting from 2-iodopyrimidine-4-carbonitrile 51.1 and 7-amino-5-methyl-[1,2,5]oxadiazolo[3,4-b]pyridin-6-ylmethyl acetate E. The mixture is purified by flash column chromatography on silica gel (using a solvent gradient from cyclohexane/ethyl acetate 100/0 to 20/80).

Yield: 10% of theory

Mass spectrometry (ESI$^+$): m/z=268 $[M+H]^+$

HPLC (Method 1): Retention time=0.73 min.

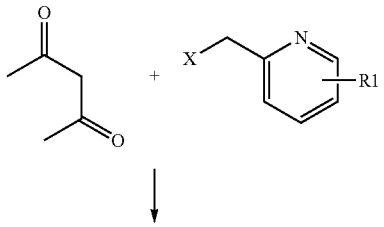

-continued

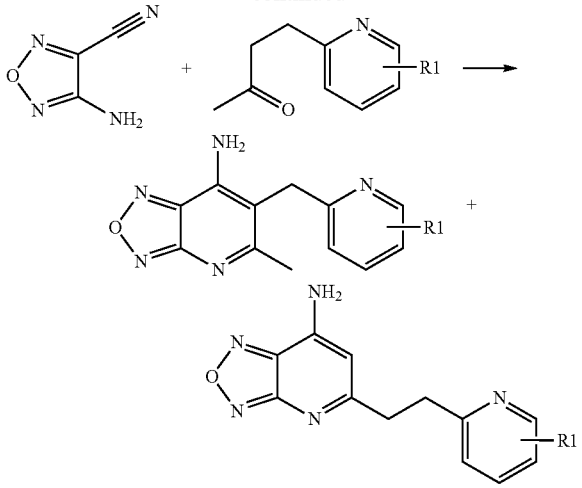

Example 52

5-Methyl-6-(6-trifluoromethyl-pyridin-2-ylmethyl)[1,2,5]oxadiazolo[3,4-b]pyridin-7-ylamine

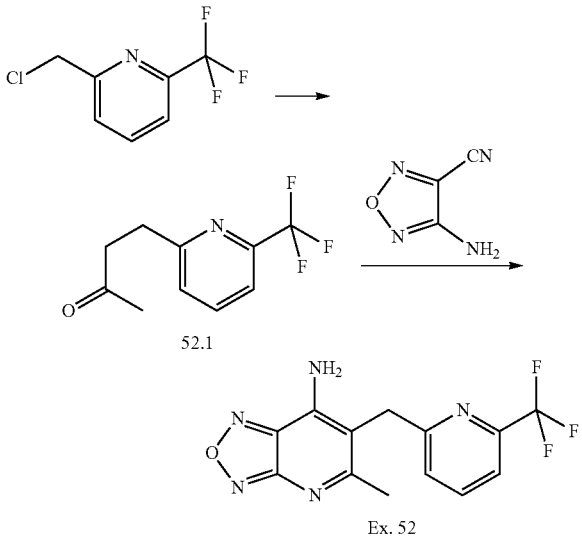

52.1

Ex. 52

52.1 4-(6-Trifluoromethyl-pyridin-2-yl)-butan-2-one

A mixture of commercially available (Frontier) 2-(chloromethyl)-6-(trifluoromethyl)pyridine (1.00 g, 5.11 mmol), acetyl acetone (0.53 mL, 5.11 mmol) and potassium carbonate (710 mg, 5.11 mmol) in 25 mL methanol is stirred at 80° C. for 18 hours. Water is added and the product is extracted with dichloromethane. The organic layer is dried and concentrated under reduced pressure. The residue is purified by silica gel chromatography (eluent: petrol ether/ethyl acetate 100/0->85/15)

Mass spectrometry (ESI$^+$): m/z=192 [M+H]$^+$

HPLC (Method 3): Retention time=0.94 min.

Final Step (Example 52)

Under nitrogen atmosphere commercially available 4-amino-1,2,5-oxadiazole-3-carbonitrile (ABCR) (45.0 mg, 0.41 mmol) and 4-(6-trifluoromethyl-pyridin-2-yl)-butan-2-one 52.1 (88.79 mg, 0.41 mmol) are dissolved in 2.0 mL of toluene. Tin(IV)chloride (0.10 mL, 0.82 mmol) is added and the mixture is stirred at room temperature for 30 minutes. The mixture is stirred at 110° C. for 18 hours. The solid is filtered and purified by RP-HPLC (modifier: trifluoroacetic acid).

Yield: 6 mg (5% of theory)

Mass spectrometry (ESI$^+$): m/z=310 [M+H]$^+$

HPLC (Method 2): Retention time=0.82 min.

Example 53

5-Methyl-6-(6-methyl-pyridin-2-yl methyl)-[1,2,5]oxadiazolo[3,4-b]pyridin-7-ylamine

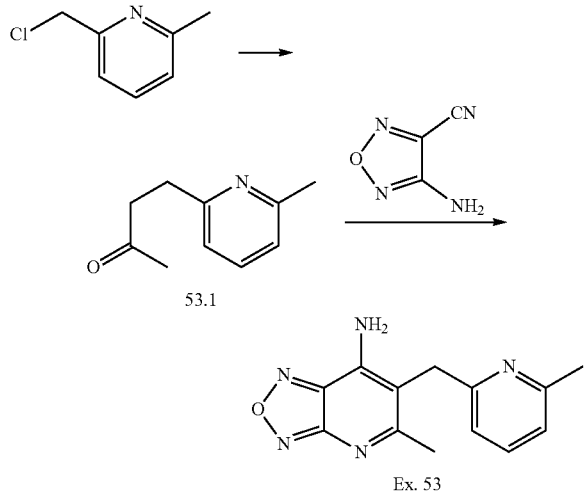

53.1

Ex. 53

53.1 4-(6-Methyl-pyridin-2-yl)-butan-2-one

Analogously to intermediate 52.1, obtained by starting from commercially available (BroadPharma) 2-(chloromethyl)-6-(methyl)pyridine and acetyl acetone. The mixture is purified by RP-HPLC (modifier: $NH_4OH$).

Mass spectrometry (ESI$^+$): m/z=164 [M+H]$^+$

HPLC (Method 1): Retention time=0.73 min.

Final Step (Example 53)

Analogously to Example 52, obtained by starting from commercially available 4-amino-1,2,5-oxadiazole-3-carbonitrile (ABCR) and 4-(6-methyl-pyridin-2-yl)-butan-2-one 53.1. The mixture is stirred at reflux for 1 hour. The precipitate is collected via filtration and suspended in 1 M sodium hydroxide solution. The suspension is extracted with ethyl acetate. The organic phase is dried and concentrated under reduced pressure. The residue is purified by RP-HPLC (modifier: $NH_4OH$).

Yield: 4% of theory

Mass spectrometry (ESI$^+$): m/z=256 [M+H]$^+$

HPLC (Method 1): Retention time=0.82 min.

Example 54

6-(7-Amino-5-methyl-[1,2,5]oxadiazolo[3,4-b]pyridin-6-ylmethyl)-pyridine-2-carboxylic acid methylamide

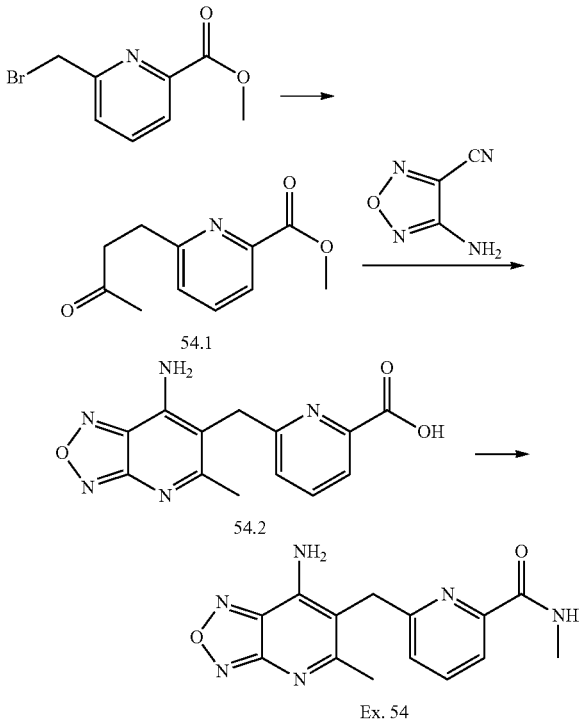

54.1 6-(3-Oxo-butyl)-pyridine-2-carboxylic Acid Methyl Ester

Analogously to intermediate 52.1 obtained by starting from commercially available (Activate) 6-bromomethylpyridine-2-carboxylic acid methyl ester and acetyl acetone.

Yield: 32% of theory

Mass spectrometry (ESI$^+$): m/z=208 $[M]^+$

HPLC (Method 3): Retention time=0.74 min.

54.2 6-(7-Amino-5-methyl-[1,2,5]oxadiazolo[3,4-b]pyridin-6-ylmethyl)-pyridine-2-carboxylic Acid Commercially available 4-Amino-1,2,5-oxadiazole-3-carbonitrile (ABCR) (303 mg, 2.76 mmol) and 6-(3-Oxobutyl)-pyridine-2-carboxylic acid methyl ester 54.1 (571 mg, 2.76 mmol) are dissolved in 20 mL of toluene. Tin(IV) chloride (0.65 mL, 5.51 mmol) is added and the mixture is stirred at room temperature for 30 minutes and then for 19 hours at reflux. The mixture is concentrated under reduced pressure and the residue is taken up in methanol. An aqueous solution of sodium hydroxide is added and tin salts are filtered. The filtrate is purified by RP-HPLC (modifier: trifluoroacetic acid).

Yield: 170 mg (22% of theory)

Mass spectrometry (ESI$^+$): m/z=286 $[M+H]^+$

HPLC (Method 3): Retention time=0.61 min.

Final Step (Example 54)

6-(7-Amino-5-methyl-[1,2,5]oxadiazolo[3,4-b]pyridin-6-ylmethyl)-pyridine-2-carboxylic acid 54.2 (50.0 mg, 0.18 mmol), O-(7-azabenzotriazol-1-yl)-N,N,N',N'-tetramethyluronium hexafluoro-phosphate (73.3 mg, 0.19 mmol) and N,N-diisopropylethylamine (70 μL, 0.39 mmol) in 0.5 mL N,N-dimethylformamide are stirred at room temperature for 15 minutes. Methyl amine (2 M solution in tetrahydrofuran; 0.18 mL, 0.35 mmol) is added and the mixture is stirred at room temperature for 18 hours. The mixture is diluted with methanol, acidified with trifluoroacetic acid and purified by RP-HPLC (modifier: trifluoroacetic acid). The product is obtained after another purification by RP-HPLC (modifier: ammonium hydroxide)

Yield: 21 mg (40% of theory)

Mass spectrometry (ESI$^+$): m/z=299 $[M+H]^+$

HPLC (Method 1): Retention time=0.73 min.

Example 55

6-(7-Amino-5-methyl-[1,2,5]oxadiazolo[3,4-b]pyridin-6-ylmethyl)-pyridine-2-carboxylic Acid Dimethylamide

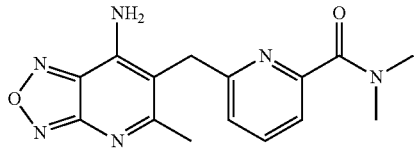

Obtained by starting from 6-(7-Amino-5-methyl-[1,2,5]oxadiazolo[3,4-b]pyridin-6-ylmethyl)-pyridine-2-carboxylic acid 54.2 and dimethyl amine (2 M solution in tetrahydrofuran).

Yield: 5.5 mg (10% of theory)

Mass spectrometry (ESI$^+$): m/z=313 $[M+H]^+$

HPLC (Method 1): Retention time=0.72 min.

Final Step (Example 56)

6-(7-Amino-5-methyl-[1,2,5]oxadiazolo[3,4-b]pyridin-6-ylmethyl)-pyridine-2-carboxylic Acid Amide

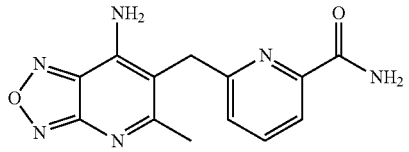

6-(7-Amino-5-methyl-[1,2,5]oxadiazolo[3,4-b]pyridin-6-ylmethyl)-pyridine-2-carboxylic acid 54.2 (320 mg, 1.1 mmol) is taken in 5 mL N,N-dimethylformamide and N,N'-carbonyldiimidazole (190 mg, 1.2 mmol). The mixture is stirred for 2 hours at room temperature. The mixture is cooled to 0° C. before ammonia (32% aqueous solution, 1.9 mL) is added. The mixture is stirred for 18 hours at room temperature. The mixture is purified by RP-HPLC (modifier: ammonium hydroxide).

Yield: 130 mg (41% of theory)

Mass spectrometry (ESI$^+$): m/z=285 $[M+H]^+$

HPLC (Method 3): Retention time=0.63 min.

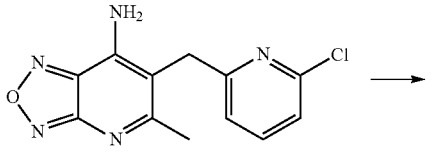

Ex.3

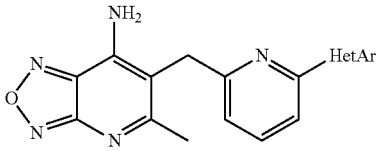

Examples 57-62

Example 57

6-(6-Furan-2-yl-pyridin-2-ylmethyl)-5-methyl-[1,2,5]oxadiazolo[3,4-b]pyridin-7-ylamine

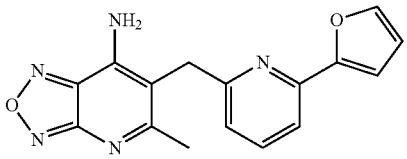

6-(6-Chloro-pyridin-2-ylmethyl)-5-methyl-[1,2,5]oxadiazolo[3,4-b]pyridin-7-ylamine (example 3) (50.0 mg, 0.18 mmol), 2-Furanboronic acid (30.4 mg, 0.27 mmol), potassium carbonate (2 M aqueous solution, 200 μL, 0.40 mmol) and 1,1'-bis(di-tert-butylphosphino)ferrocene palladium dichloride (35.5 mg, 54.4 μmol) are dissolved in 2.0 mL dioxane. The mixture is stirred at 100° C. for 1 hour. The mixture is purified by RP-HPLC (modifier: ammonium hydroxide).

Yield: 8 mg (14% of theory)

Mass spectrometry (ESI$^+$): m/z=308 $[M+H]^+$

HPLC (Method 1): Retention time=0.92 min.

Example 58

5-methyl-6-[(pyridin-2-yl)methyl]-[1,2,5]oxadiazolo[3,4-b]pyridin-7-amine

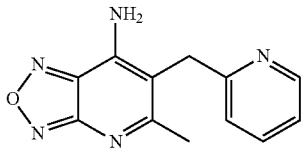

Obtained as a by-product when synthesizing Example 57. The mixture is purified by RP-HPLC (modifier: ammonium hydroxide).

Yield: 16 mg (37% of theory)

Mass spectrometry (ESI$^+$): m/z=242 $[M+H]^+$

HPLC (Method 1): Retention time=0.72 min.

Example 59

5-Methyl-6-[6-(3-methyl-3H-imidazol-4-yl)-pyridin-2-yl methyl]-[1,2,5]oxadiazolo[3,4-b]pyridin-7-ylamine

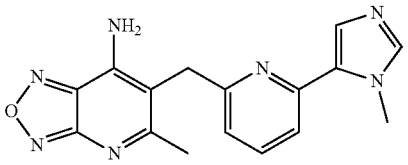

Obtained by starting from 6-(6-Chloro-pyridin-2-ylmethyl)-5-methyl-[1,2,5]oxadiazolo[3,4-b]pyridin-7-ylamine (example 3) and (1-Methyl-1H-imidazol-5-yl)boronic acid pinacol ester. The mixture is purified by RP-HPLC (modifier: ammonium hydroxide).

Yield: 15 mg (25% of theory)

Mass spectrometry (ESI$^+$): m/z=322 $[M+H]^+$

HPLC (Method 1): Retention time=0.76 min.

Example 60

6-[6-(3,5-Dimethyl-isoxazol-4-yl)-pyridin-2-ylmethyl]-5-methyl-[1,2,5]oxadiazolo[3,4-b]pyridin-7-ylamine

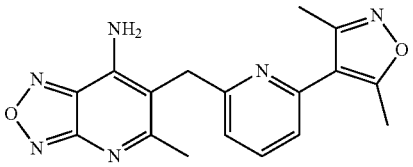

Obtained by starting from 6-(6-Chloro-pyridin-2-ylmethyl)-5-methyl-[1,2,5]oxadiazolo[3,4-b]pyridin-7-ylamine (example 3) and 3,5-Dimethyl-4-isoxazolboronic acid. The mixture filtered over silica gel and purified by RP-HPLC (modifier: trifluoroacetic acid).

Yield: 28 mg (47% of theory)

Mass spectrometry (ESI$^+$): m/z=337 $[M+H]^+$

HPLC (Method 1): Retention time=0.87 min.

Example 61

5-Methyl-6-[6-(1-methyl-3-trifluoromethyl-1H-pyrazol-4-yl)-pyridin-2-ylmethyl]-[1,2,5]oxadiazolo[3,4-b]pyridin-7-ylamine

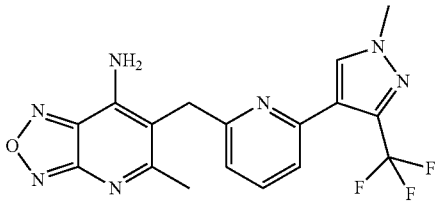

Obtained by starting from 6-(6-Chloro-pyridin-2-ylmethyl)-5-methyl-[1,2,5]oxadiazolo[3,4-b]pyridin-7-ylamine (example 3) and 1-Methyl-3-trifluoromethylpyrazole-4-boronic acid. The mixture filtered and purified by RP-HPLC (modifier: ammonium hydroxide).

Yield: 14 mg (39% of theory)

Mass spectrometry (ESI$^+$): m/z=390 $[M+H]^+$

HPLC (Method 3): Retention time=0.91 min.

Example 62

5-Methyl-6-[6-(3-trifluoromethyl-1H-pyrazol-4-yl) pyridin-2-ylmethyl]-[1,2,5]oxadiazolo[3,4-b]pyridin-7-ylamine

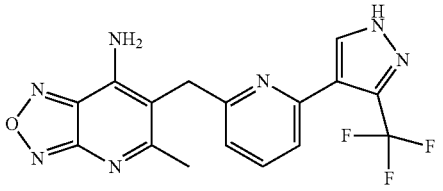

Obtained by starting from 6-(6-Chloro-pyridin-2-ylmethyl)-5-methyl-[1,2,5]oxadiazolo[3,4-b]pyridin-7-ylamine (example 3) and 3-(Trifluoromethyl)-1H-pyrazole-4-boronic acid pinacol ester. The mixture is quenched with methanol, filtered and purified by RP-HPLC (modifier: ammonium hydroxide).

Yield: 61 mg (90% of theory)

Mass spectrometry (ESI$^+$): m/z=376 $[M+H]^+$

HPLC (Method 3): Retention time=0.86 min.

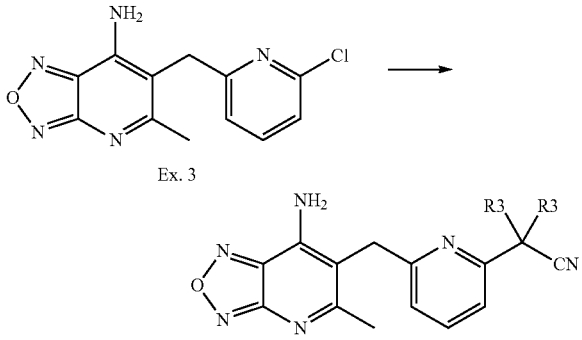

Example 63

2-[6-(7-Amino-5-methyl-[1,2,5]oxadiazolo[3,4-b] pyridin-6-ylmethyl)-pyridin-2-yl]-2-methyl-propionitrile

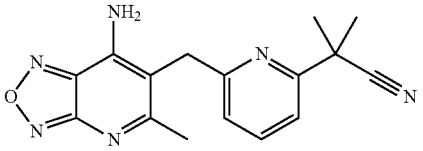

6-(6-Chloro-pyridin-2-ylmethyl)-5-methyl-[1,2,5]oxadiazolo[3,4-b]pyridin-7-ylamine (example 3) (50.00 mg, 0.181 mmol), isobutyronitrile (0.100 mg, 1.447 mmol) and sodium bis(trimethylsilyl)amide 1 M solution in THF (0.500 ml, 0.50 mmol) are dissolved in 1.0 mL of tetrahydrofuran. The mixture is stirred at 100° C. for 15 minutes in a microwave. The mixture is purified by RP-HPLC (modifier: ammonium hydroxide).

Yield: 21 mg (37% of theory)

Mass spectrometry (ESI$^-$): m/z=309 $[M+H]^+$

HPLC (Method 1): Retention time=0.88 min.

Example 64

1-[6-(7-Amino-5-methyl-[1,2,5]oxadiazolo[3,4-b] pyridin-6-ylmethyl)-pyridin-2-yl]-cyclopentanecarbonitrile

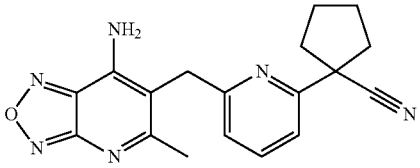

Analogously to example 63, obtained by starting from 6-(6-Chloro-pyridin-2-ylmethyl)-5-methyl-[1,2,5]oxadiazolo[3,4-b]pyridin-7-ylamine (example 3) and cyclopentanecarbonitrile.

Yield: 34% of theory

Mass spectrometry (ESI$^-$): m/z=335 $[M+H]^+$

HPLC (Method 1): Retention time=0.93 min.

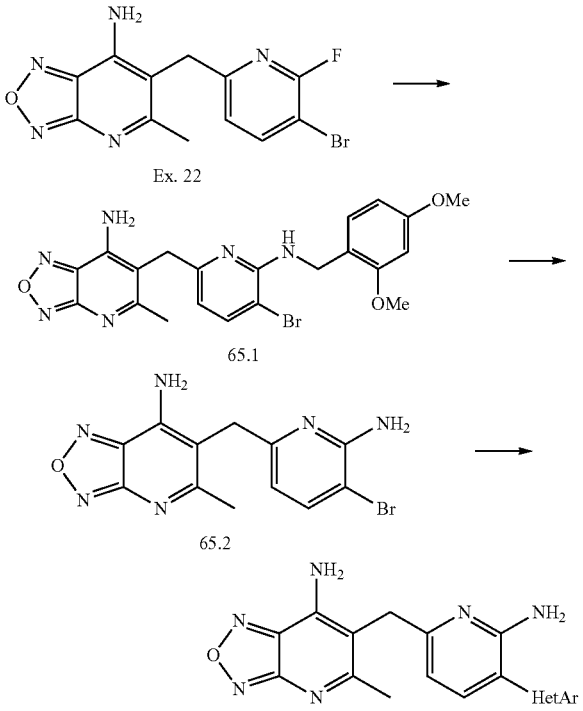

65.1 6-[5-Bromo-6-(2,4-dimethoxy-benzylamino)-pyridin-2-ylmethyl]-5-methyl-[1,2,5]oxadiazolo[3,4-b]pyridin-7-ylamine Obtained by starting from 6-(5-Bromo-6-fluoro-pyridin-2-ylmethyl)-5-methyl-[1,2,5]oxadiazolo[3,4-b]pyridin-7-ylamine (example 22) and 2,4-dimethoxy-benzylamine using diisopropylethylamine instead of potassium fluoride. Stirred for 18 hours at 120° C. and purified by RP-HPLC (modifier: trifluoroacetic acid).

Yield: 0.15 g (58% of theory)

Mass spectrometry ($ESI^+$): m/z=484, 486 $[M+H]^+$

HPLC (Method 4): Retention time=1.07 min.

65.2 6-(6-Amino-5-bromo-pyridin-2-ylmethyl)-5-methyl-[1,2,5]oxadiazolo[3,4-b]pyridin-7-ylamine To 6-[5-Bromo-6-(2,4-dimethoxy-benzylamino)-pyridin-2-ylmethyl]-5-methyl-[1,2,5]-oxadiazolo-[3,4-b]-pyridin-7-ylamine 65.1 (0.271 g, 0.558 mmol) in 10 mL dichloromethane, is added 2.0 mL trifluoroacetic acid. The mixture is stirred for 18 h, partitioned between saturated aqueous sodium bicarbonate solution and dichloromethane. The phases are separated and the aqueous phase is extracted with dichloromethane. The combined organic phase are dried and concentrated under reduced pressure.

Yield: 0.20 g (107% of theory)

Mass spectrometry ($ESI^+$): m/z=334, 336 $[M+H]^+$

HPLC (Method 4): Retention time=0.83 min

Final Step (Example 65)

6-[6-Amino-5-(5,6-dihydro-4H-pyrrolo[1,2-b]pyrazol-3-yl)-pyridin-2-ylmethyl]-5-methyl-[1,2,5]oxadiazolo[3,4-b]pyridin-7-ylamine

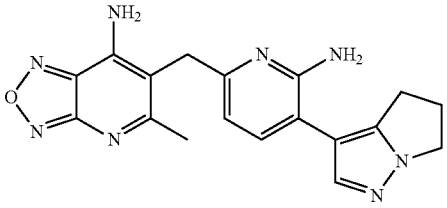

Obtained by starting from 6-(6-Amino-5-bromo-pyridin-2-ylmethyl)-5-methyl-[1,2,5]oxadiazolo[3,4-b]pyridin-7-ylamine 65.2 and 3-(4,4,5,5-tetramethyl-[1,3,2]dioxaborolan-2-yl)-5,6-dihydro-4H-pyrrolo[1,2-b]pyrazole. The mixture is filtered over silica gel und washed with ethyl acetate. The mixture is purified by RP-HPLC (modifier: ammonium hydroxide).

Yield: 15 mg (34% of theory)

Mass spectrometry ($ESI^+$): m/z=363 $[M+H]^+$

HPLC (Method 1): Retention time=0.81 min.

Example 66

6-[6-Amino-5-(3,5-dimethyl-isoxazol-4-yl)-pyridin-2-ylmethyl]-5-methyl-[1,2,5]oxadiazolo[3,4-b]pyridin-7-ylamine

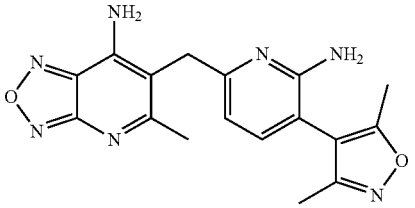

Obtained by starting from 6-(6-Amino-5-bromo-pyridin-2-ylmethyl)-5-methyl-[1,2,5]oxadiazolo[3,4-b]pyridin-7-ylamine 65.2 and 3,5-dimethylisoxazole-4-boronic acid pinacol ester and additional methanol. The mixture is filtered over silica gel und washed with ethyl acetate. The mixture is purified by RP-HPLC (modifier: trifluoroacetic acid).

Yield: 18 mg (43% of theory)

Mass spectrometry ($ESI^+$): m/z=352 $[M+H]^+$

HPLC (Method 1): Retention time=0.91 min.

Example 67

6-(6-Amino-5-thiazol-5-yl-pyridin-2-ylmethyl)-5-methyl-[1,2,5]oxadiazolo[3,4-b]pyridin-7-ylamine

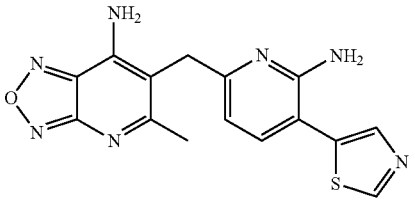

Obtained by starting from 6-(6-Amino-5-bromo-pyridin-2-ylmethyl)-5-methyl-[1,2,5]oxadiazolo[3,4-b]pyridin-7-ylamine 65.2 and 5-(4,4,5,5-tetramethyl-[1,3,2]dioxaborolan-2-yl)-thiazole. The mixture is filtered over silica gel und washed with ethyl acetate. The mixture is purified by RP-HPLC (modifier: trifluoroacetic acid).

Yield: 12 mg (29% of theory)

Mass spectrometry ($ESI^+$): m/z=340 $[M+H]^+$

HPLC (Method 1): Retention time=0.63 min.

Example 68

6-[6-Amino-5-(2,4-dimethyl-2H-pyrazol-3-yl)-pyridin-2-ylmethyl]-5-methyl-[1,2,5]oxadiazolo[3,4-b]pyridin-7-ylamine

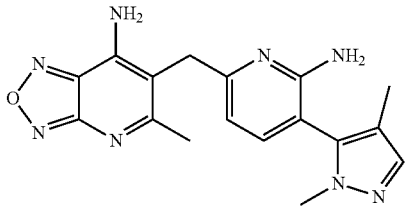

Obtained by starting from 6-(6-Amino-5-bromo-pyridin-2-ylmethyl)-5-methyl-[1,2,5]oxadiazolo[3,4-b]pyridin-7-ylamine 65.2 and 1,4-dimethyl-5-(4,4,5,5-tetramethyl-1,3,2-dioxaborolan-2-yl)-1H-pyrazole and additional methanol. The mixture is filtered over silica gel and washed with ethyl acetate. The organic phase is dried, concentrated under reduced pressure and purified by RP-HPLC (modifier: trifluoroacetic acid). The residue is diluted in acetonitrile, basified with triethylamine and purified by RP-HPLC (modifier: ammonium hydroxide).

Yield: 8 mg (24% of theory)

Mass spectrometry (ESI$^+$): m/z=351 [M+H]$^+$

HPLC (Method 1): Retention time=0.82 min.

Example 69

6-(6-Amino-5-pyrazin-2-yl-pyridin-2-ylmethyl)-5-methyl-[1,2,5]oxadiazolo[3,4-b]pyridin-7-ylamine

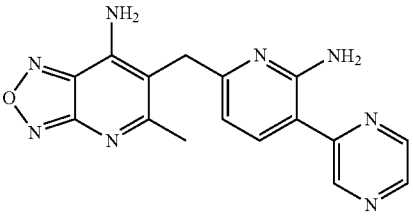

Obtained by starting from 6-(6-Amino-5-bromo-pyridin-2-ylmethyl)-5-methyl-[1,2,5]oxadiazolo[3,4-b]pyridin-7-ylamine 65.2 and pyrazine-2-boronic acid pinacol ester and additional methanol. The mixture is diluted with methanol, filtered over silica gel. and purified by RP-HPLC (modifier ammonium hydroxide).

Yield: 9 mg (22% of theory)

Mass spectrometry (ESI$^+$): m/z=335 [M+H]$^+$

HPLC (Method 1): Retention time=0.79 min.

Example 70

6-(7-Amino-5-methyl-[1,2,5]oxadiazolo[3,4-b]pyridin-6-ylmethyl)-3-difluoromethoxy-pyridine-2-carbonitrile

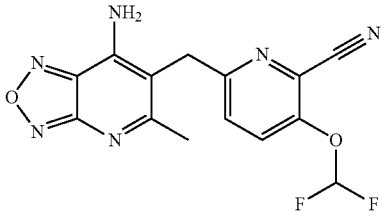

6-(6-Bromo-5-difluoromethoxy-pyridin-2-ylmethyl)-5-methyl-[1,2,5]oxadiazolo[3,4-b]pyridin-7-ylamine (example 15) (45.0 mg, 0.12 mmol) is dissolved in 1.0 mL of N,N-dimethylformamide. Bis(diphenylphosphino)ferrocene (6.48 mg, 0.01 mmol) and zinc cyanide (14.9 mg, 0.13 mmol) are added and argon is bubbled through the reaction mixture for 10 minutes. (Tris(dibenzylideneacetone)dipalladium(0) (5.35 mg, 0.01 mmol) is added and the reaction mixture is stirred at 120° C. for 10 minutes. The mixture is purified by RP-HPLC (modifier: ammonium hydroxide).

Yield: 25 mg (64% of theory)

Mass spectrometry (ESI$^+$): m/z=333 [M+H]$^+$

HPLC (Method 1): Retention time=0.86 min.

Example 71

6-(7-Amino-5-methyl-[1,2,5]oxadiazolo[3,4-b]pyridin-6-ylmethyl)-3-bromopyridine-2-carbonitrile

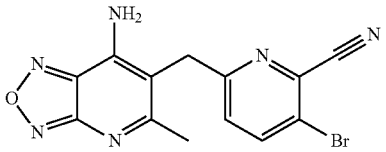

Obtained analogously to example 70 by starting from 6-(5,6-Dibromo-pyridin-2-ylmethyl)-5-methyl-[1,2,5]oxadiazolo[3,4-b]pyridin-7-ylamine (example 21) and zinc cyanide. The mixture is purified by RP-HPLC (modifier: ammonium hydroxide).

Yield: 30% of theory

Mass spectrometry (ESI$^+$): m/z=345, 347 [M+H]$^+$

HPLC (Method 4): Retention time=0.80 min.

Example 72

6-(7-Amino-5-methyl-[1,2,5]oxadiazolo[3,4-b]pyridin-6-ylmethyl)-2-fluoro-nicotinonitrile

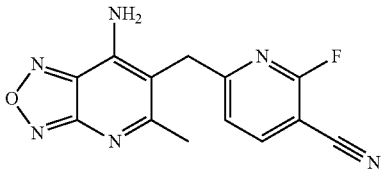

Obtained analogously to example 70 by starting from 6-(5-Bromo-6-fluoro-pyridin-2-ylmethyl)-5-methyl-[1,2,5]oxadiazolo[3,4-b]pyridin-7-ylamine (example 22) and zinc cyanide. The mixture is purified by RP-HPLC (modifier: ammonium hydroxide).

Yield: 89% of theory

Mass spectrometry (ESI$^+$): m/z=285 [M+H]$^+$

HPLC (Method 4): Retention time=0.74 min.

Example 73

6-(7-Amino-5-methyl-[1,2,5]oxadiazolo[3,4-b]pyridin-6-ylmethyl)-2-difluoromethoxy-nicotinonitrile

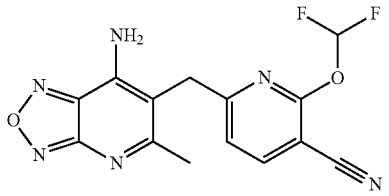

Obtained analogously to example 70 by starting from 6-(5-Bromo-6-difluoromethoxy-pyridin-2-ylmethyl)-5-methyl-[1,2,5]oxadiazolo[3,4-b]pyridin-7-ylamine (example 23) and zinc cyanide. The mixture is purified by RP-HPLC (modifier: ammonium hydroxide).

Yield: 7% of theory

Mass spectrometry (ESI$^+$): m/z=333 [M+H]$^+$

HPLC (Method 1): Retention time=0.89 min.

Example 74

6-(7-Amino-5-methyl-[1,2,5]oxadiazolo[3,4-b]pyridin-6-ylmethyl)-4-trifluoromethyl-nicotinonitrile

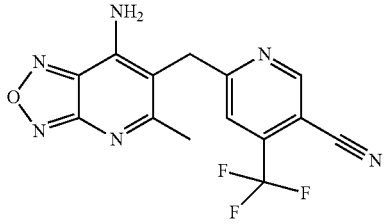

Obtained analogously to example 70 by starting from 6-(5-Bromo-4-trifluoromethyl-pyridin-2-ylmethyl)-5-methyl-[1,2,5]oxadiazolo[3,4-b]pyridin-7-ylamine (example 32) and zinc cyanide. The mixture is purified by RP-HPLC (modifier: ammonium hydroxide).

Yield: 62% of theory

Mass spectrometry (ESI$^+$): m/z=335 [M+H]$^+$

HPLC (Method 1): Retention time=0.89 min.

Example 75

2-(7-amino-5-methyl-[1,2,5]oxadiazolo[3,4-b]pyridin-6-ylmethyl)-5-(trifluoromethyl)pyrimidine-4-carbonitrile

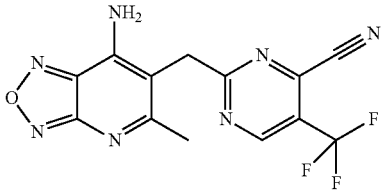

Obtained analogously to example 70 by starting from 6-[4-chloro-5-(trifluoromethyl)pyrimidin-2-yl]methyl-5-methyl-[1,2,5]oxadiazolo[3,4-b]pyridin-7-amine (example 50) and zinc cyanide. The mixture is purified by RP-HPLC (modifier: ammonium hydroxide).

Yield: 23% of theory

Mass spectrometry (ESI$^+$): m/z=336 [M+H]$^+$

HPLC (Method 1): Retention time=0.87 min.

Example 76

6-(7-amino-5-methyl-[1,2,5]oxadiazolo[3,4-b]pyridin-6-ylmethyl)pyridine-3,4-dicarbonitrile

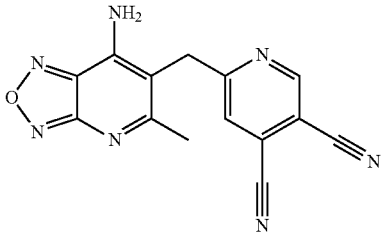

Obtained analogously to example 70 by starting from 2-(7-amino-5-methyl-[1,2,5]oxadiazolo[3,4-b]pyridin-6-ylmethyl)-5-bromopyridine-4-carbonitrile (example 27) and zinc cyanide. The mixture is purified by RP-HPLC (modifier: ammonium hydroxide).

Yield: 76% of theory

Mass spectrometry (ESI$^+$): m/z=292 [M+H]$^+$

HPLC (Method 1): Retention time=0.78 min.

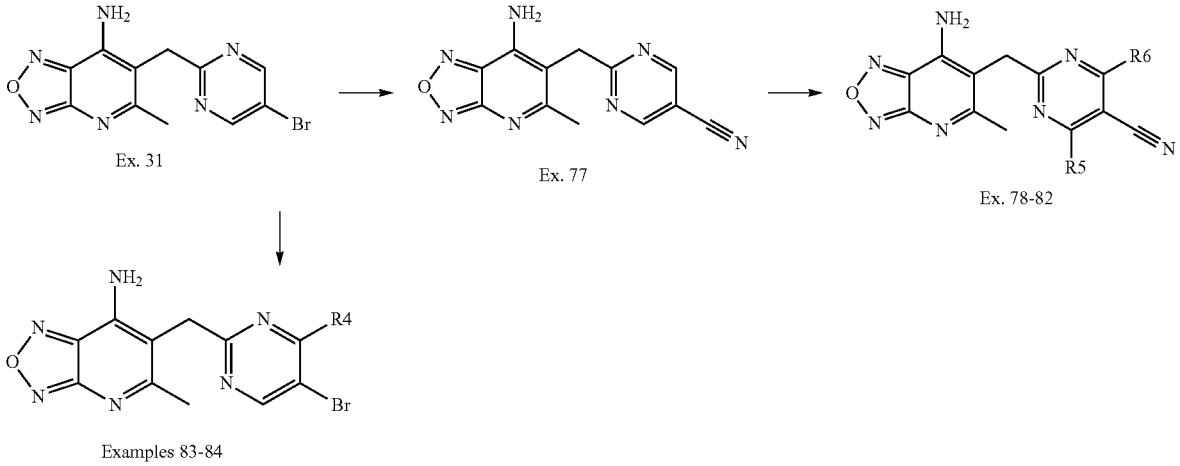

Example 77

2-(7-amino-5-methyl-[1,2,5]oxadiazolo[3,4-b]pyridin-6-ylmethyl)pyrimidine-5-carbonitrile

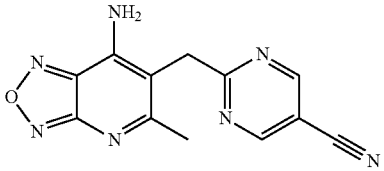

Obtained analogously to example 70 by starting from 6-[(5-bromopyrimidin-2-yl)methyl]-5-methyl-[1,2,5]oxadiazolo[3,4-b]pyridin-7-amine (example 31) and zinc cyanide. The reaction mixture is purified by RP-HPLC (modifier: ammonium hydroxide).

Yield: 87% of theory

Mass spectrometry ($ESI^+$): m/z=268 $[M+H]^+$

HPLC (Method 1): Retention time=0.71 min.

Example 78

2-(7-amino-5-methyl-[1,2,5]oxadiazolo[3,4-b]pyridin-6-ylmethyl)-4-(trifluoromethyl)pyrimidine-5-carbonitril

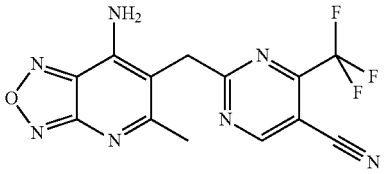

Obtained analogously to example 165 by starting from 2-(7-amino-5-methyl-[1,2,5]oxadiazolo[3,4-b]pyridin-6-ylmethyl)pyrimidine-5-carbonitrile (example 77) and zinc trifluoromethanesulfinate. The mixture is purified by RP-HPLC (modifier: ammonium hydroxide)

Yield: 13% of theory

Mass spectrometry ($ESI^+$): m/z=336 $[M+H]^+$

HPLC (Method 1): Retention time=0.88 min.

Example 79

2-(7-amino-5-methyl-[1,2,5]oxadiazolo[3,4-b]pyridin-6-ylmethyl)-4-(difluoromethyl)pyrimidine-5-carbonitrile

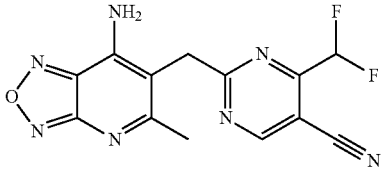

Obtained analogously to example 165 by starting from 2-(7-amino-5-methyl-[1,2,5]oxadiazolo[3,4-b]pyridin-6-ylmethyl)pyrimidine-5-carbonitrile (example 77) and zinc difluoromethanesulfinate. The mixture is purified by RP-HPLC (modifier: ammonium hydroxide)

Yield: 12% of theory

Mass spectrometry ($ESI^+$): m/z=318 $[M+H]^+$

HPLC (Method 1): Retention time=0.81 min.

Example 80

2-(7-amino-5-methyl-[1,2,5]oxadiazolo[3,4-b]pyridin-6-ylmethyl)-4-(oxolan-3-yl)pyrimidine-5-carbonitrile

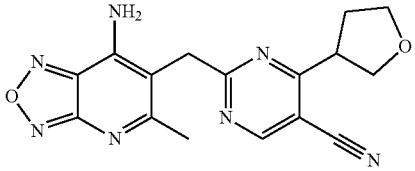

2-(7-amino-5-methyl-[1,2,5]oxadiazolo[3,4-b]pyridin-6-ylmethyl)pyrimidine-5-carbonitrile (example 77) (25.0 mg, 0.09 mmol) is added to a mixture of 1.5 mL diethylcarbonate and 1.0 mL water. Sodium oxolane-3-sulfinate (44.4 mg, 0.28 mmol) is added and the mixture is cooled with an ice bath. 2-methyl-prop-2-yl-hydroperoxid (64.1 μL, 0.47 mmol) is added slowly. The mixture is stirred at 90° C. for 1 hour.

Yield: 8 mg (25% of theory)

Mass spectrometry (ESI$^+$): m/z=338 [M+H]$^+$

HPLC (Method 4): Retention time=0.75 min.

Example 81

2-(7-amino-5-methyl-[1,2,5]oxadiazolo[3,4-b]pyridin-6-ylmethyl)-4-methylpyrimidine-5-carbonitrile

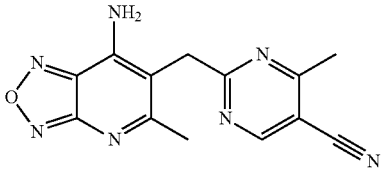

Analogously to example 80 obtained as a by-product by starting from 2-(7-amino-5-methyl-[1,2,5]oxadiazolo[3,4-b]pyridin-6-ylmethyl)pyrimidine-5-carbonitrile (example 77) and sodium trifluoromethanesulfinate. The mixture is purified by RP-HPLC (modifier: trifluoroacetic acid)

Yield: 15% of theory

Mass spectrometry (ESI$^+$): m/z=282 [M+H]$^+$

HPLC (Method 4): Retention time=0.69 min.

Example 82

2-(7-amino-5-methyl-[1,2,5]oxadiazolo[3,4-b]pyridin-6-yl methyl)-4-(1,1-difluoroethyl)pyrimidine-5-carbonitrile

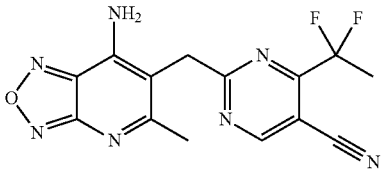

Analogously to example 80 obtained by starting from 2-(7-amino-5-methyl-[1,2,5]oxadiazolo[3,4-b]pyridin-6-ylmethyl)pyrimidine-5-carbonitrile (example 77) and sodium 1,1-difluoroethane-1-sulfinate.

Yield: 36% of theory

Mass spectrometry (ESI$^+$): m/z=332 [M+H]$^+$

HPLC (Method 4): Retention time=0.83 min.

Example 83

6-[5-bromo-4-(trifluoromethyl)pyrimidin-2-yl] methyl-5-methyl-[1,2,5]oxadiazolo[3,4-b]pyridin-7-amine

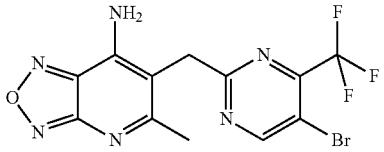

Analogously to example 80 obtained by starting from 6-(5-bromo-pyrimidin-2-ylmethyl)-5-methyl-[1,2,5]oxadiazolo[3,4-b]pyridin-7-ylamine (example 31) and zinc trifluoromethanesulfinate. The mixture is purified by RP-HPLC (modifier: ammonium hydroxide)

Yield: 45% of theory

Mass spectrometry (ESI$^+$): m/z=389, 391 [M+H]$^+$

HPLC (Method 1): Retention time=0.96 min.

Example 84

6-[5-bromo-4-(difluoromethyl)pyrimidin-2-yl] methyl-5-methyl-[1,2,5]oxadiazolo[3,4-b]pyridin-7-amine

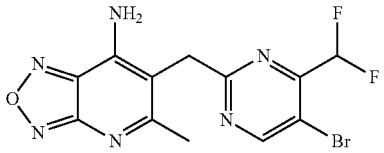

Analogously to example 80 obtained by starting from 6-(5-bromo-pyrimidin-2-ylmethyl)-5-methyl-[1,2,5]oxadiazolo[3,4-b]pyridin-7-ylamine (example 31) and zinc difluoromethanesulfinate. The mixture is purified by RP-HPLC (modifier: ammonium hydroxide)

Yield: 29% of theory

Mass spectrometry (ESI$^+$): m/z=371, 373 [M+H]$^+$

HPLC (Method 1): Retention time=0.89 min.

Example 85

6-(6-Methanesulfinyl-pyridin-2-ylmethyl)-5-methyl-[1,2,5]oxadiazolo[3,4-b]pyridin-7-ylamine

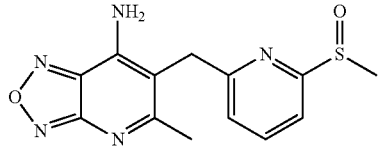

5-Methyl-6-(6-methylsulfanyl-pyridin-2-ylmethyl)-[1,2,5]oxadiazolo[3,4-b]pyridin-7-ylamine (example 16) (200 mg, 0.70 mmol) is dissolved in 10 mL dichloromethane. 3-chloroperoxybenzoic acid (274.5 mg, 1.60 mmol) is added and the mixture is stirred at room temperature for 30 minutes. The reaction mixture is concentrated under reduced pressure and the residue is purified by RP-HPLC (modifier: ammonium hydroxide).

Yield: 75 mg (35% of theory)

Mass spectrometry (ESI$^+$): m/z=304 [M+H]$^+$

HPLC (Method 3): Retention time=0.65 min.

Example 86

6-(6-Methanesulfonyl-pyridin-2-ylmethyl)-5-methyl-[1,2,5]oxadiazolo[3,4-b]pyridin-7-ylamine

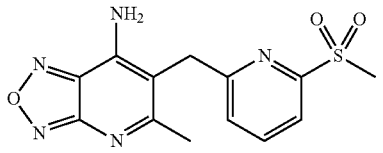

Analogously to example 85 obtained by starting from 5-Methyl-6-(6-methylsulfanyl-pyridin-2-ylmethyl)-[1,2,5]oxadiazolo[3,4-b]pyridin-7-ylamine (example 16) and 3-chloroperoxybenzoic acid. The reaction mixture is concentrated and purified by RP-HPLC (modifier: ammonium hydroxide).

Yield: 33% of theory

Mass spectrometry (ESI$^+$): m/z=320 [M+H]$^+$

HPLC (Method 3): Retention time=0.68 min.

Example 87

6-(5-Methanesulfinyl-pyridin-2-ylmethyl)-5-methyl-[1,2,5]oxadiazolo[3,4-b]pyridin-7-ylamine

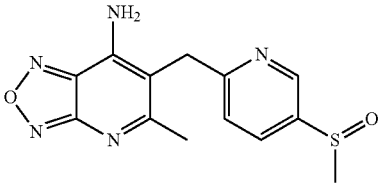

Analogously to example 85 obtained by starting from 5-methyl-6-(5-methylsulfanyl-pyridin-2-ylmethyl)-[1,2,5]oxadiazolo[3,4-b]pyridin-7-ylamine (example 44) and 3-chloroperoxybenzoic acid. The mixture is concentrated and purified by RP-HPLC (modifier: ammonium hydroxide).

Yield: 54% of theory

Mass spectrometry (ESI$^+$): m/z=304 [M+H]$^+$

HPLC (Method 3): Retention time=0.60 min.

Example 88

6-(5-Methanesulfonyl-pyridin-2-ylmethyl)-5-methyl-[1,2,5]oxadiazolo[3,4-b]pyridin-7-ylamine

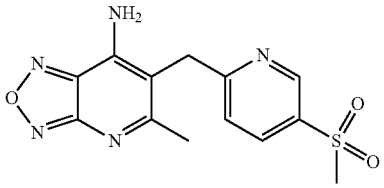

Analogously to example 85 obtained by starting from 5-methyl-6-(5-methylsulfanyl-pyridin-2-ylmethyl)-[1,2,5]oxadiazolo[3,4-b]pyridin-7-ylamine (example 44) and 3-chloroperoxybenzoic acid. The mixture is concentrated and purified by RP-HPLC (modifier: ammonium hydroxide).

Yield: 38% of theory

Mass spectrometry (ESI$^+$): m/z=320 [M+H]$^+$

HPLC (Method 3): Retention time=0.65 min.

Example 89

6-(7-Amino-5-methyl-[1,2,5]oxadiazolo[3,4-b]pyridin-6-ylmethyl)-3-trifluoromethyl-pyridine-2-carboxylic Acid Amide

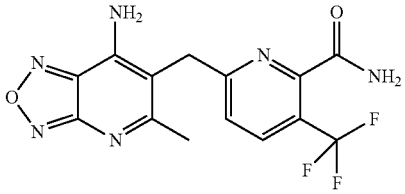

6-(7-Amino-5-methyl-[1,2,5]oxadiazolo[3,4-b]pyridin-6-ylmethyl)-3-trifluoromethyl-pyridine-2-carbonitrile (example 48) (50.0 mg, 0.15 mmol) and sodium hydroxide (2.0 mL, 34.7 mmol) are dissolved in 2.0 mL ethanol and the reaction mixture is stirred at 50° C. for 2 hours. The reaction mixture is cooled to room temperature, acidified with 4 M hydrochloric acid (74.8 μL, 0.30 mmol) and purified by RP-HPLC (modifier: trifluoroacetic acid).

Yield: 14 mg (26% of theory)

Mass spectrometry (ESI$^+$): m/z=353 [M+H]$^+$

HPLC (Method 3): Retention time=0.72 min.

Example 90

6-(7-Amino-5-methyl-[1,2,5]oxadiazolo[3,4-b]pyridin-6-ylmethyl)-3-difluoromethoxy-pyridine-2-carboxylic Acid Amide

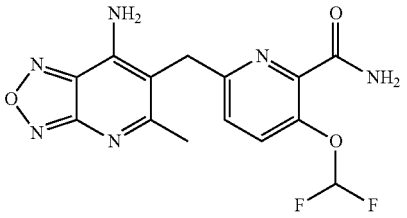

Analogously to example 89 obtained by starting from 6-(7-amino-5-methyl-[1,2,5]oxadiazolo[3,4-b]pyridin-6-ylmethyl)-3-difluoromethoxy-pyridine-2-carbonitrile (example 70). The mixture is purified without addition hydrochloric acid by RP-HPLC (modifier: ammonium hydroxide).

Yield: 50% of theory

Mass spectrometry (ESI$^+$): m/z=351 $[M+H]^+$

HPLC (Method 1): Retention time=0.72 min.

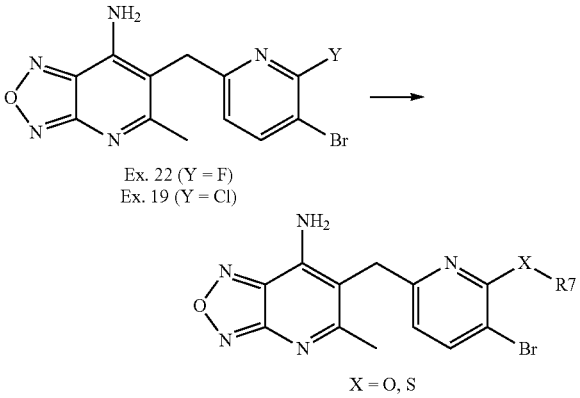

Examples 91-102

Example 91

6-[5-Bromo-6-(3,3,3-trifluoro-propoxy)-pyridin-2-ylmethyl]-5-methyl[-1,2,5]oxadiazolo[3,4-b]pyridin-7-ylamine

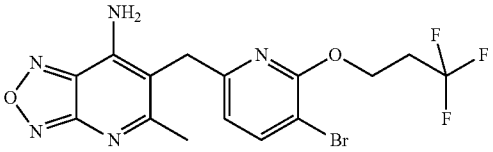

6-(5-Bromo-6-fluoro-pyridin-2-ylmethyl)-5-methyl-[1,2,5]oxadiazolo[3,4-b]pyridin-7-ylamine (example 22) (45.0 mg, 0.13 mmol), 3,3,3-trifluoro-propan-1-ol (151.8 mg, 1.33 mmol)) and cesium carbonate (108.4 mg, 0.33 mmol) are dissolved in 1.0 mL of tetrahydrofuran. and stirred at 120° C. for 15 minutes. The reaction mixture is concentrated under reduced pressure and the residue is purified by RP-HPLC (modifier: ammonium hydroxide).

Yield: 36 mg (62% of theory)

HPLC (Method 5): Retention time=0.89 min.; m/z=431, 433 $[M+H]^+$

Example 92

6-[5-Bromo-6-(2,2-difluoro-ethoxy)-pyridin-2-ylmethyl]-5-methyl-[1,2,5]oxadiazolo[3,4-b]pyridin-7-ylamine

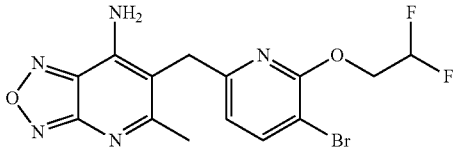

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 2,2-difluoro-ethanol.

Yield: 103% of theory

HPLC (Method 5): Retention time=0.82 min.; m/z=399, 401 $[M+H]^+$

Example 93

6-[5-Bromo-6-(2,2-difluoro-cyclopropylmethoxy)-pyridin-2-yl methyl]-5-methyl-[1,2,5]oxadiazolo[3,4-b]pyridin-7-ylamine

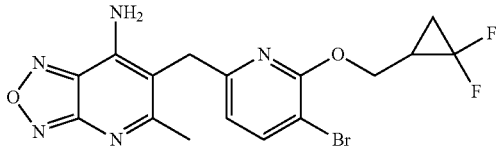

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and (2,2-difluorocyclopropyl)methanol.

Yield: 68% of theory

HPLC (Method 5): Retention time=0.88 min.; m/z=425, 427 $[M+H]^+$

Example 94

1-[6-(7-Amino-5-methyl-[1,2,5]oxadiazolo[3,4-b]pyridin-6-ylmethyl)-3-bromo-pyridin-2-yloxy]-2-methyl-propan-2-ol

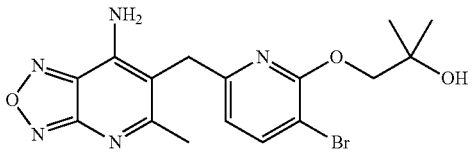

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 2-methyl-propane-1,2-diol.

Yield: 47% of theory

HPLC (Method 5): Retention time=0.76 min.; m/z=409, 411 $[M+H]^+$

Example 95

6-[5-Bromo-6-(3-methyl-oxetan-3-ylmethoxy)-pyridin-2-ylmethyl]-5-methyl-[1,2,5]oxadiazolo[3,4-b]pyridin-7-ylamine

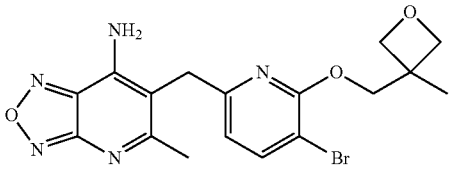

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 3-methyl-3-oxetanemethanol.

Yield: 63% of theory

HPLC (Method 5): Retention time=0.81 min.; m/z=420, 422 $[M+H]^+$

Example 96

6-[5-Bromo-6-(2,2,2-trifluoro-ethoxy)-pyridin-2-ylmethyl]-5-methyl-[1,2,5]oxadiazolo[3,4-b]pyridin-7-ylamine

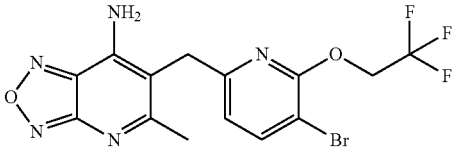

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 2,2,2-trifluoro-ethanol.

Yield: 74% of theory

HPLC (Method 5): Retention time=0.87 min.; m/z=417, 419 $[M+H]^+$

Example 97

6-(5-Bromo-6-methoxy-pyridin-2-ylmethyl)-5-methyl-[1,2,5]oxadiazolo[3,4-b]pyridin-7-ylamine

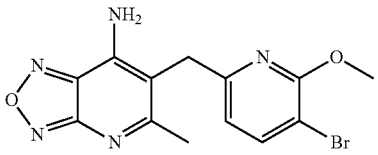

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and methanol, use N-methyl-2-pyrrolidone instead of tetrahydrofuran as solvent.

Yield: 70% of theory

HPLC (Method 5): Retention time=0.83 min.; m/z=350, 352 $[M+H]^+$

Example 98

6-[5-Bromo-6-(oxetan-3-yloxy)-pyridin-2-ylmethyl]-5-methyl-[1,2,5]oxadiazolo[3,4-b]pyridin-7-ylamine

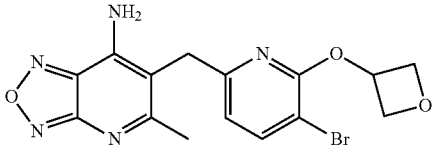

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and oxetan-3-ol.

Yield: 15% of theory

HPLC (Method 10): Retention time=0.82 min.; m/z=392, 394 $[M+H]^+$

Example 99

6-[5-Bromo-6-(2,2-difluoro-propoxy)-pyridin-2-ylmethyl]-5-methyl-[1,2,5]oxadiazolo[3,4-b]pyridin-7-ylamine

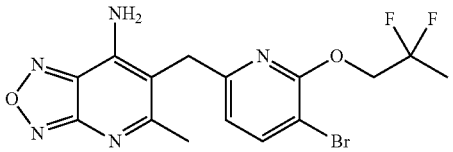

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 2,2-difluoro-propan-1-ol.

Yield: 87% of theory

HPLC (Method 10): Retention time=0.97 min.; 414, 416 $[M+H]^+$

Example 100

6-[5-Bromo-6-(2-fluoro-ethoxy)-pyridin-2-ylmethyl]-5-methyl-[1,2,5]oxadiazolo[3,4-b]pyridin-7-ylamine

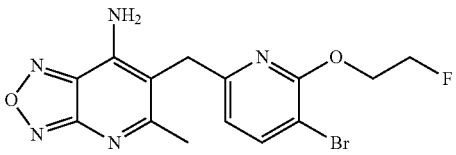

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 2-fluoro-ethanol.

Yield: 62% of theory

HPLC (Method 1): Retention time=0.95 min.; m/z=382, 384 $[M+H]^+$

Example 101

6-[5-Bromo-6-(3-fluoro-propoxy)-pyridin-2-yl methyl]-5-methyl-[1,2,5]oxadiazolo[3,4-b]pyridin-7-ylamine

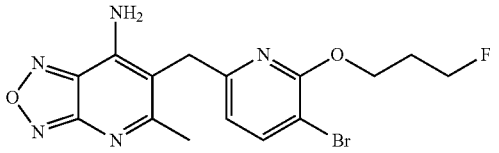

Analogously to example 91 obtained by starting from 6-(5-bromo-6-fluoro-pyridin-2-ylmethyl)-5-methyl-[1,2,5]oxadiazolo[3,4-b]pyridin-7-ylamine (example 22) and 3-fluoro-propan-1-ol.

Yield: 36% of theory

HPLC (Method 1): Retention time=1.00 min.; m/z=396, 398 $[M+H]^+$

Example 102

6-(5-Bromo-6-methylsulfanyl-pyridin-2-ylmethyl)-5-methyl-[1,2,5]oxadiazolo[3,4-b]pyridin-7-ylamine

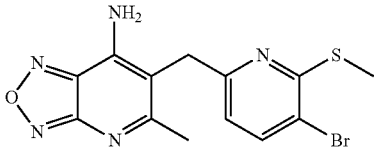

6-(5-Bromo-6-chloro-pyridin-2-ylmethyl)-5-methyl-[1,2,5]oxadiazolo[3,4-b]pyridin-7-ylamine (40.00 mg; 0,113 mmol) (example 19) and sodium methanethiolate (11,860 mg; 0.170 mmol) dissolved in 2 ml tetrahydrofuran/dimethyl formamide=1/1. Stirred at 120° C. for 18 hours. The mixture is purified by RP-HPLC (modifier: ammonium hydroxide).

Yield: 9 mg (21% of theory)

HPLC (Method 4): Retention time=0.96 min.; m/z=366, 368 $[M+H]^+$

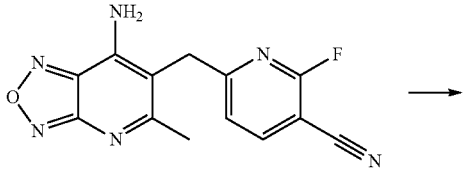

Ex. 72

-continued

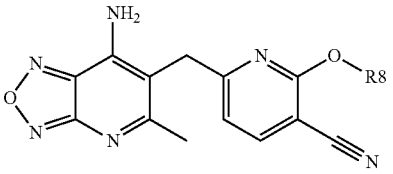

Examples 103-113

Example 103

6-(7-Amino-5-methyl-[1,2,5]oxadiazolo[3,4-b]pyridin-6-ylmethyl)-2-(2,2-difluoro-propoxy)-nicotinonitrile

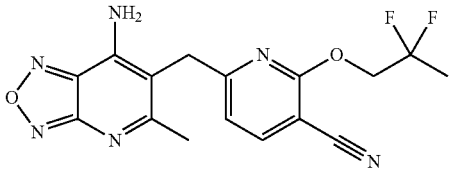

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 2,2-difluoro-propan-1-ol.

Yield: 43% of theory

Mass spectrometry ($ESI^-$): m/z=361 $[M+H]^+$

HPLC (Method 1): Retention time=0.90 min.

Example 104

6-(7-Amino-5-methyl-[1,2,5]oxadiazolo[3,4-b]pyridin-6-ylmethyl)-2-(oxetan-3-yloxy)-nicotinonitrile

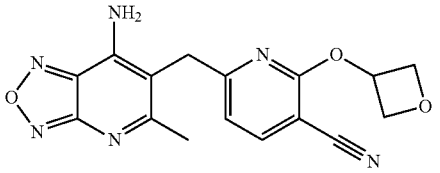

Analogously to example 91 obtained by starting from 6-(7-amino-5-methyl-[1,2,5]oxadiazolo[3,4-b]pyridin-6-ylmethyl)-2-fluoro-nicotinonitrile (example 72) and oxetan-3-ol.

Yield: 55% of theory

Mass spectrometry ($ESI^-$): m/z=339 $[M+H]^+$

HPLC (Method 1): Retention time=0.79 min.

Example 105

6-(7-Amino-5-methyl-[1,2,5]oxadiazolo[3,4-b]pyridin-6-ylmethyl)-2-(2-hydroxy-2-methyl-propoxy) nicotinonitrile

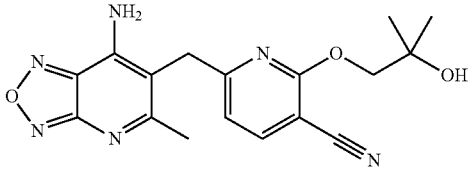

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 2-methylpropane-1,2-diol.

Yield: 49% of theory

Mass spectrometry (ESI⁻): m/z=355 $[M+H]^+$

HPLC (Method 1): Retention time=0.84 min.

Example 106

6-(7-Amino-5-methyl-[1,2,5]oxadiazolo[3,4-b]pyridin-6-ylmethyl)-2-(2-fluoro-ethoxy)-nicotinonitrile

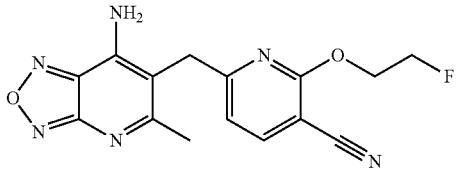

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 2-fluoroethanol.

Yield: 50% of theory

Mass spectrometry (ESI⁻): m/z=329 $[M+H]^+$

HPLC (Method 1): Retention time=0.84 min.

Example 107

6-(7-Amino-5-methyl-[1,2,5]oxadiazolo[3,4-b]pyridin-6-ylmethyl)-2-(2,2,2-trifluoro-ethoxy)-nicotinonitrile

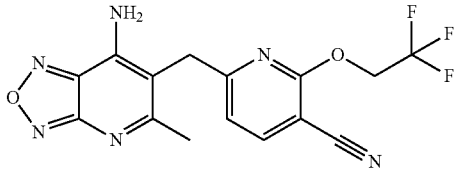

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 2,2,2-trifluoro-ethanol.

Yield: 46% of theory

Mass spectrometry (ESI⁻): m/z=365 $[M+H]^+$

HPLC (Method 1): Retention time=0.91 min.

Example 108

6-(7-Amino-5-methyl-[1,2,5]oxadiazolo[3,4-b]pyridin-6-ylmethyl)-2-(3-fluoro-propoxy)-nicotinonitrile

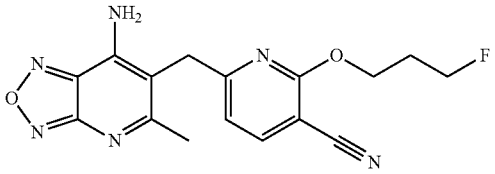

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 3-fluoropropan-1-ol.

Yield: 28% of theory

Mass spectrometry (ESI⁻): m/z=343 $[M+H]^+$

HPLC (Method 1): Retention time=0.89 min.

Example 109

6-(7-Amino-5-methyl-[1,2,5]oxadiazolo[3,4-b]pyridin-6-ylmethyl)-2-(2,2-difluoro-ethoxy)-nicotinonitrile

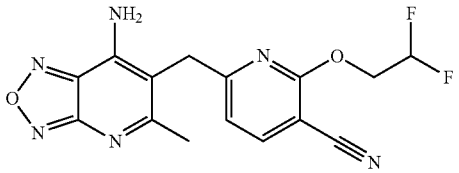

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 2,2-difluoro-ethanol.

Yield: 49% of theory

Mass spectrometry (ESI⁻): m/z=347 $[M+H]^+$

HPLC (Method 1): Retention time=0.87 min.

Example 110

6-(7-Amino-5-methyl-[1,2,5]oxadiazolo[3,4-b]pyridin-6-ylmethyl)-2-(3,3,3-trifluoro-propoxy)-nicotinonitrile

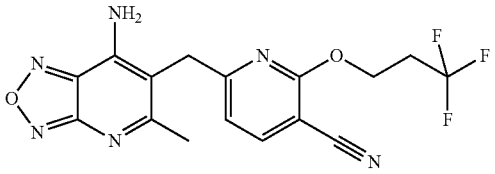

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 3,3,3-trifluoro-propan-1-ol.

Yield: 37% of theory

Mass spectrometry (ESI⁻): m/z=379 [M+H]⁺

HPLC (Method 1): Retention time=0.94 min.

Example 111

6-(7-Amino-5-methyl-[1,2,5]oxadiazolo[3,4-b]pyridin-6-ylmethyl)-2-(3-methyl-oxetan-3-ylmethoxy)-nicotinonitrile

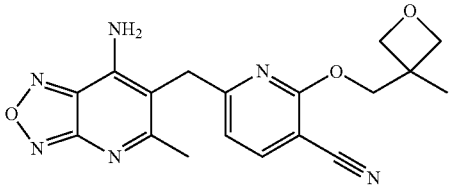

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 3-methyl-3-oxetane-methanol.

Yield: 51% of theory

Mass spectrometry (ESI⁻): m/z=367 [M+H]⁺

HPLC (Method 1): Retention time=0.85 min.

Example 112

6-(7-Amino-5-methyl-[1,2,5]oxadiazolo[3,4-b]pyridin-6-ylmethyl)-2-(2,2-difluoro-cyclopropyl-methoxy)-nicotinonitrile

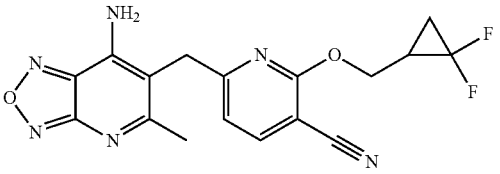

Analogously to example 91 obtained by starting from 6-(7-amino-5-methyl-[1,2,5]oxadiazolo[3,4-b]pyridin-6-ylmethyl)-2-fluoro-nicotinonitrile (example 72) and (2,2-difluorocyclopropyl)-methanol.

Yield: 54% of theory

Mass spectrometry (ES⁻): m/z=373 [M+H]⁻

HPLC (Method 1): Retention time=0.91 min.

Example 113

6-(7-Amino-5-methyl-[1,2,5]oxadiazolo[3,4-b]pyridin-6-ylmethyl)-2-oxo-1,2-dihydro-pyridine-3-carbonitrile

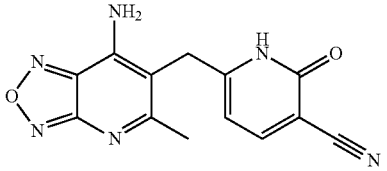

Analogously to example 91 obtained by starting from 6-(7-amino-5-methyl-[1,2,5]oxadiazolo[3,4-b]pyridin-6-ylmethyl)-2-fluoro-nicotinonitrile (example 72) and 3,3,3-trifluoro-propan-1-ol.

Yield: 60% of theory

Mass spectrometry (ESI⁻): m/z=283 [M+H]⁺

HPLC (Method 1): Retention time=0.52 min.

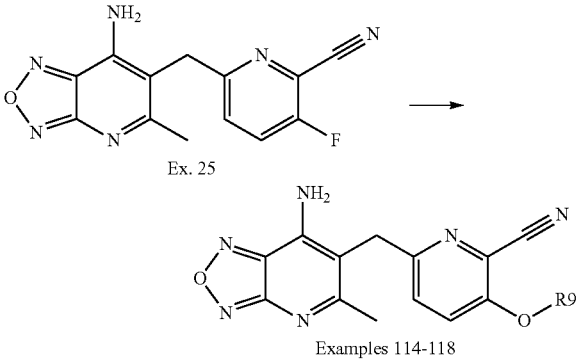

Example 114

6-(7-Amino-5-methyl-[1,2,5]oxadiazolo[3,4-b]pyridin-6-ylmethyl)-3-(2,2,2-trifluoro-ethoxy)-pyridine-2-carbonitrile

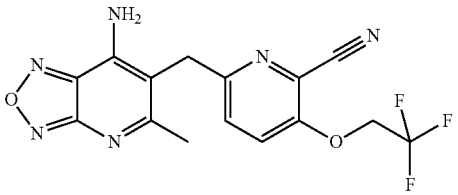

Analogously to example 91 obtained by starting from 6-(7-amino-5-methyl-[1,2,5]oxadiazolo[3,4-b]pyridin-6-ylmethyl)-3-fluoro-pyridine-2-carbonitrile (example 25) and 2,2,2-trifluoro-ethanol. The mixture is purified by RP-HPLC (modifier: trifluoroacetic acid).

Yield: 58% of theory

Mass spectrometry (ESI⁻): m/z=365 [M+H]⁺

HPLC (Method 5): Retention time=0.90 min.

Example 115

6-(7-Amino-5-methyl-[1,2,5]oxadiazolo[3,4-b]pyridin-6-ylmethyl)-3-(2-fluoro-ethoxy)-pyridine-2-carbonitrile

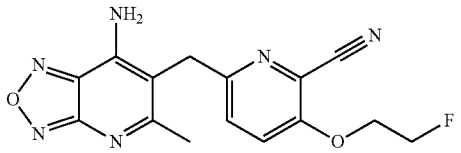

Analogously to example 91 obtained by starting from 6-(7-amino-5-methyl-[1,2,5]oxadiazolo[3,4-b]pyridin-6-ylmethyl)-3-fluoro-pyridine-2-carbonitrile (example 25) and 2-fluoro-ethanol. The mixture is purified by RP-HPLC (modifier: trifluoroacetic acid).

Yield: 50% of theory

Mass spectrometry (ESI$^-$): m/z=329 $[M+H]^+$

HPLC (Method 5): Retention time=0.78 min.

Example 116

6-(7-Amino-5-methyl-[1,2,5]oxadiazolo[3,4-b]pyridin-6-ylmethyl)-3-(2,2-difluoro-ethoxy)-pyridine-2-carbonitrile

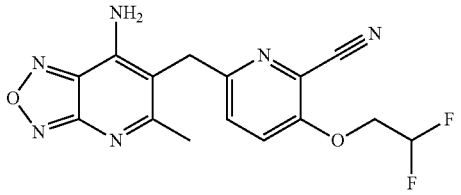

Analogously to example 91 obtained by starting from 6-(7-amino-5-methyl-[1,2,5]oxadiazolo[3,4-b]pyridin-6-ylmethyl)-3-fluoro-pyridine-2-carbonitrile (example 25) and 2,2-difluoro-ethanol.

Yield: 21% of theory

Mass spectrometry (ESI$^-$): m/z=347 $[M+H]^+$

HPLC (Method 12): Retention time=0.71 min.

Example 117

6-(7-Amino-5-methyl-[1,2,5]oxadiazolo[3,4-b]pyridin-6-ylmethyl)-3-(2-methyl-2H-pyrazol-3-yloxy)-pyridine-2-carbonitrile

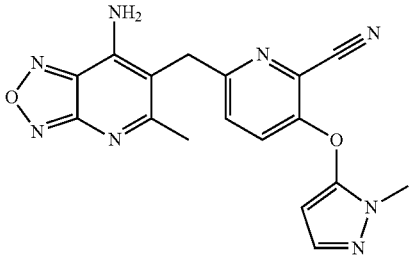

Analogously to example 91 obtained by starting from 6-(7-amino-5-methyl-[1,2,5]oxadiazolo[3,4-b]pyridin-6-ylmethyl)-3-fluoro-pyridine-2-carbonitrile (example 25) and 2-methyl-2H-pyrazol-3-ol.

Yield: 51% of theory

Mass spectrometry (ESI$^-$): m/z=363 $[M+H]^+$

HPLC (Method 1): Retention time=0.86 min.

Example 118

6-(7-Amino-5-methyl-[1,2,5]oxadiazolo[3,4-b]pyridin-6-ylmethyl)-3-phenoxy-pyridine-2-carbonitrile

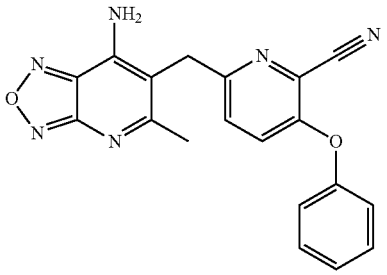

Analogously to example 91 obtained by starting from 6-(7-amino-5-methyl-[1,2,5]oxadiazolo[3,4-b]pyridin-6-ylmethyl)-3-fluoro-pyridine-2-carbonitrile (example 25) and phenol.

Yield: 33% of theory

Mass spectrometry (ESI$^-$): m/z=359 $[M+H]^+$

HPLC (Method 1): Retention time=0.99 min.

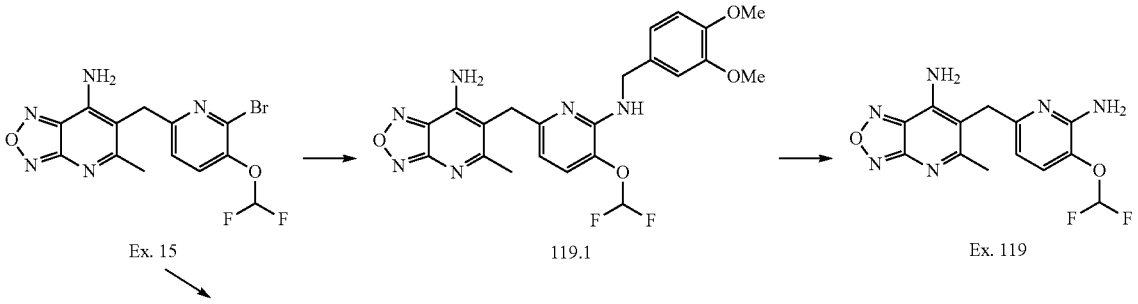

-continued

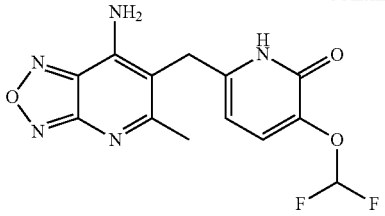

Ex. 120

Example 119

6-(6-Amino-5-difluoromethoxy-pyridin-2-ylmethyl)-5-methyl-[1,2,5]oxadiazolo[3,4-b]pyridin-7-ylamine

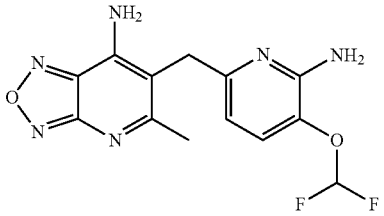

6-(6-Bromo-5-difluoromethoxy-pyridin-2-ylmethyl)-5-methyl-[1,2,5]oxadiazolo[3,4-b]pyridin-7-ylamine (example 15) (50.00 mg, 0.129 mmol), 2,4-dimethoxy-benzylamine (86.601 mg, 0.518 mmol) and N,N-diisopropylethylamine (67.190 μL, 0.388 mmol) in 2 mL dimethylsulfoxide are stirred at 120° C. for 18 hours. The mixture is purified by RP-HPLC (modifier: ammonium hydroxide). The residue is dissolved in 2 mL dichloromethane, acidified with 0.50 mL trifluoroacetic acid, stirred at room temperature for 3 h and concentrated under reduced pressure.

Yield: 24 mg (35% of theory)

Mass spectrometry ($ESI^+$): m/z=323 $[M+H]^+$

HPLC (Method 1): Retention time=0.60 min.

Example 120

6-(7-Amino-5-methyl-[1,2,5]oxadiazolo[3,4-b]pyridin-6-ylmethyl)-3-difluoromethoxy-1H-pyridin-2-one

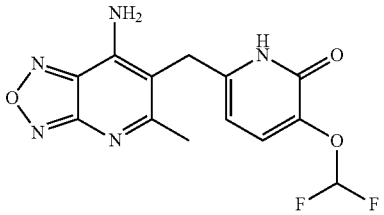

Analogously to example 91 obtained by starting from 6-(6-bromo-5-difluoromethoxy-pyridin-2-ylmethyl)-5-methyl-[1,2,5]oxadiazolo[3,4-b]pyridin-7-ylamine (example 15) and 3,3,3-trifluoro-propan-1-ol.

Yield: 38% of theory

Mass spectrometry ($ESI^-$): m/z=324 $[M+H]^+$

HPLC (Method 1): Retention time=0.63 min.

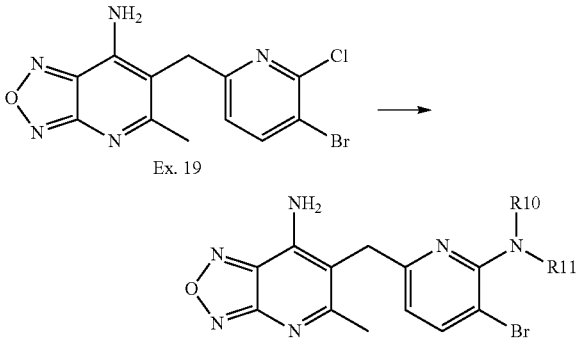

Ex. 19

Examples 121-134

Example 121

6-{5-Bromo-6-[(3-methyl-oxetan-3-ylmethyl)-amino]-pyridin-2-ylmethyl}-5-methyl-[1,2,5]oxadiazolo[3,4-b]pyridin-7-ylamine

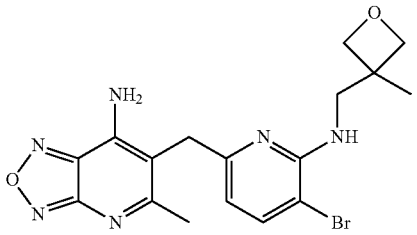

6-(5-Bromo-6-chloro-pyridin-2-ylmethyl)-5-methyl-[1,2,5]oxadiazolo[3,4-b]pyridin-7-ylamine (example 19) (30.00 mg, 0.085 mmol), C-(3-methyl-oxetan-3-yl)-methylamine (128.36 mg, 0.001 mol) and potassium fluoride (24.578 mg, 0.423 mmol) are dissolved in 3 mL N-methyl-2-pyrrolidinon and stirred for 3 hours at 150° C. The mixture is purified by RP-HPLC (modifier: ammonium hydroxide).

Yield: 53% of theory

Mass spectrometry ($ESI^+$): m/z=419, 421 $[M+H]^+$

HPLC (Method 1): Retention time=0.95 min.

Example 122

1-[6-(7-Amino-5-methyl-[1,2,5]oxadiazolo[3,4-b]pyridin-6-ylmethyl)-3-bromo-pyridin-2-yl]-3-methyl-azetidin-3-ol

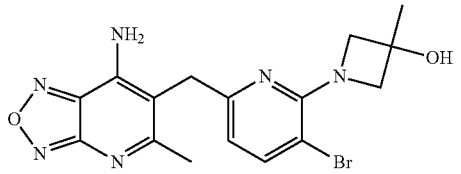

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and 3-methyl-3-azetidinol using triethylamine and acetonitrile instead of potassium fluoride and N-methyl-2-pyrrolidinon.

Yield: 39% of theory

Mass spectrometry (ESI$^+$): m/z=405, 407 $[M+H]^+$

HPLC (Method 1): Retention time=0.92 min.

Example 123

6-(5-Bromo-6-morpholin-4-yl-pyridin-2-ylmethyl)-5-methyl-[1,2,5]oxadiazolo[3,4-b]pyridin-7-ylamine

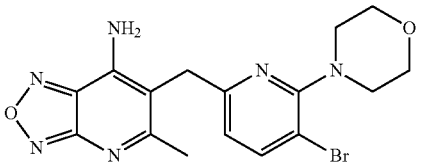

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and morpholine.

Yield: 78% of theory

Mass spectrometry (ESI$^+$): m/z=405, 407 $[M+H]^+$

HPLC (Method 1): Retention time=0.96 min.

Example 124

3-[6-(7-Amino-5-methyl-[1,2,5]oxadiazolo[3,4-b]pyridin-6-ylmethyl)-3-bromo-pyridin-2-ylamino]-2,2-di methyl-propionamide

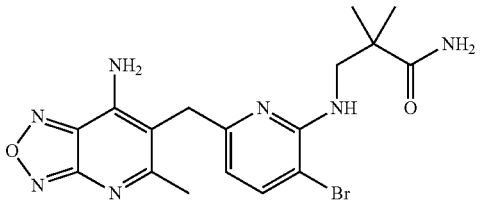

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and 3-amino-2,2-dimethyl-propionamide.

Yield: 32% of theory

Mass spectrometry (ESI$^+$): m/z=434, 436 $[M+H]^+$

HPLC (Method 1): Retention time=0.88 min.

Example 125

6-(5-Bromo-6-cyclopropylamino-pyridin-2-ylmethyl)-5-methyl-[1,2,5]oxadiazolo[3,4-b]pyridin-7-ylamine

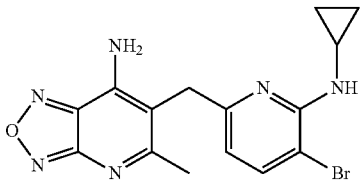

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and cyclopropylamine.

Yield: 30% of theory

Mass spectrometry (ESI$^+$): m/z=375, 377 $[M+H]^+$

HPLC (Method 1): Retention time=1.03 min.

Example 126

6-{5-Bromo-6-[(3-methyl-tetrahydro-furan-3-ylmethyl)-amino]-pyridin-2-ylmethyl}-5-methyl-[1,2,5]oxadiazolo[3,4-b]pyridin-7-ylamine

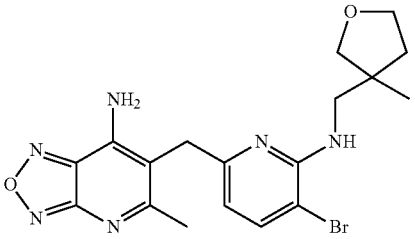

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and C-(3-methyl-tetrahydro-furan-3-yl)methylamine.

Yield: 71% of theory

Mass spectrometry (ESI$^+$): m/z=433, 435 $[M+H]^+$

HPLC (Method 4): Retention time=0.95 min.

Example 127

3-[6-(7-Amino-5-methyl-[1,2,5]oxadiazolo[3,4-b]pyridin-6-ylmethyl)-3-bromo-pyridin-2-ylamino]-2,2-di methyl-propionitrile

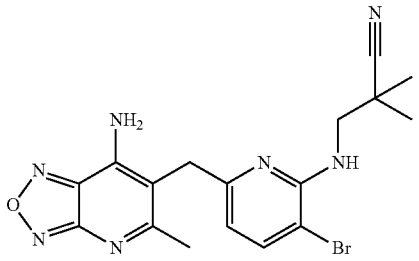

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and 3-amino-2,2-dimethyl-propionitrile.

Yield: 12% of theory

Mass spectrometry (ESI$^+$): m/z=416, 418 $[M+H]^+$

HPLC (Method 4): Retention time=0.90 min.

Example 128

6-[5-Bromo-6-(3,3-difluoro-cyclobutylamino)-pyridin-2-ylmethyl]-5-methyl-[1,2,5]oxadiazolo[3,4-b]pyridin-7-ylamine

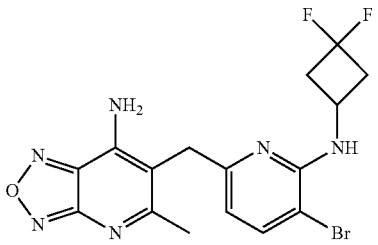

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19), 3,3-difluoro-cyclobutylamine and additional triethylamine. Stirred for 5 hours at 150° C., quenched with methanol, filtered and purified by RP-HPLC (modifier: ammonium hydroxide).

Yield: 10% of theory

Mass spectrometry (ESI$^+$): m/z=425, 427 $[M+H]^+$

HPLC (Method 1): Retention time=0.98 min.

Example 129

6-[5-Bromo-6-(3,3-difluoro-azetidin-1-yl)-pyridin-2-ylmethyl]-5-methyl-[1,2,5]oxadiazolo[3,4-b]pyridin-7-ylamine

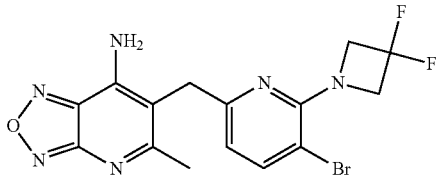

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19), 3,3-difluoroazetidine hydrochloride and additional triethylamine. Stirred for 5 hours at 150° C., quenched with methanol, filtered and purified by RP-HPLC (modifier: ammonium hydroxide).

Yield: 26% of theory

HPLC (Method 5): Retention time=0.88 min., m/z=410, 412 $[M+H]^+$

Example 130

6-[5-Bromo-6-(2-oxa-6-aza-spiro[3.3]hept-6-yl)-pyridin-2-ylmethyl]-5-methyl-[1,2,5]oxadiazolo[3,4-b]pyridine-7-ylamine

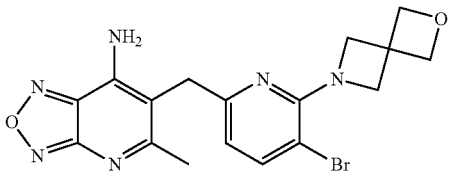

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and 2-oxa-6-aza-spiro[3,3]heptane oxalic acid salt using diisopropylethylamine instead of potassium fluoride. The reaction mixture was stirred for 2 hours at 120° C., cooled to room temperature, diluted with methanol and purified by RP-HPLC (modifier: ammonium hydroxide).

Yield: 47% of theory

HPLC (Method 1): Retention time=0.89 min., m/z=416, 418 $[M+H]^+$

Example 131

1-[6-(7-Amino-5-methyl-[1,2,5]oxadiazolo[3,4-b]pyridin-6-ylmethyl)-3-bromo-pyridin-2-yl]-[1,4]diazepan-5 -one

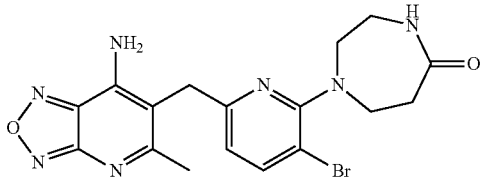

Obtained analogously to example 121 by starting 6-(5-bromo-6-fluoro-pyridin-2-ylmethyl)-5-methyl-[1,2,5]oxadiazolo[3,4-b]pyridin-7-ylamine (example 19) and [1,4]diazepam-5-one using diisopropylethylamine instead of potassium fluoride.

Yield: 46% of theory

HPLC (Method 1): Retention time=0.83 min., m/z=433, 435 $[M+H]^+$

Example 132

6-[5-Bromo-6-(3,3-difluoro-pyrrolidin-1-yl)-pyridin-2-ylmethyl]-5-methyl-[1,2,5]oxadiazolo[3,4-b]pyridin-7-ylamine

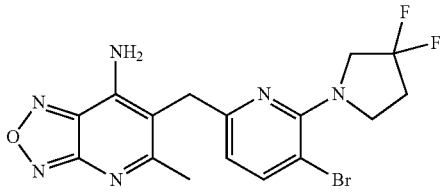

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19), 3,3-Difluoro-pyrrolidine hydrochloric salt and additional diisopropylethylamine.

Yield: 19% of theory

HPLC (Method 1): Retention time=1.04 min., m/z=424, 426 $[M+H]^+$

Example 133

6-[5-Bromo-6-(3,3-difluoro-propylamino)-pyridin-2-ylmethyl]-5-methyl-[1,2,5]oxadiazolo[3,4-b]pyridin-7-ylamine

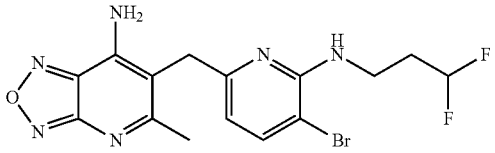

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19) and 3,3-difluoro-propylamine hydrochloride salt. Stirred for 18 hours at 150° C., quenched with methanol, filtered and purified by RP-HPLC (modifier: ammonium hydroxide).

Yield: 17% of theory

HPLC (Method 1): Retention time=0.98 min., m/z=412, 414 $[M+H]^+$

Example 134

6-[5-Bromo-6-(3,3,3-trifluoro-propylamino)-pyridin-2-ylmethyl]-5-methyl-[1,2,5]oxadiazolo[3,4-b]pyridin-7-ylamine

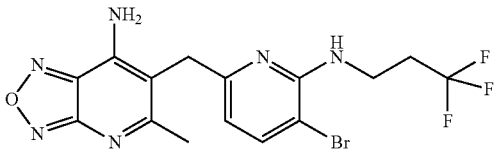

Obtained analogously to example 121 by starting from 6-(5-bromo-6-chloro-pyridin-2-ylmethyl)-5-methyl-[1,2,5]oxadiazolo[3,4-b]pyridin-7-ylamine (example 19), 3,3,3-trifluoro-propylamine hydrochloride salt and additional diisopropylethylamine. Stirred 1 hour at 150° C., quenched with methanol, filtered and purified by RP-HPLC (modifier: ammonium hydroxide).

Yield: 11% of theory

HPLC (Method 1): Retention time=0.93 min., m/z=430, 432 $[M+H]^+$

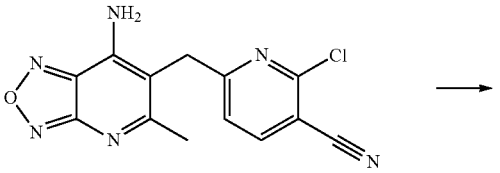

Ex. 24

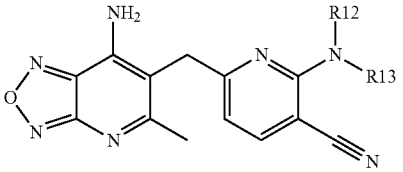

Examples 135-149

Example 135

6-(7-Amino-5-methyl-[1,2,5]oxadiazolo[3,4-b]pyridin-6-ylmethyl)-2-[(3-methyl-oxetan-3-yl methyl)-amino]-nicotinonitrile

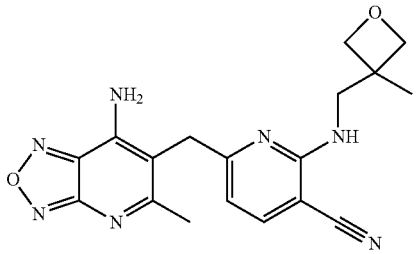

Obtained analogously to example 121 by starting from 6-(7-amino-5-methyl-[1,2,5]oxadiazolo[3,4-b]pyridin-6-ylmethyl)-2-chloro-nicotinonitrile (example 24) and C-(3-methyl-oxetan-3-yl)-methylamine.

Yield: 38% of theory

Mass spectrometry (ESI$^+$): m/z=366 $[M+H]^+$

HPLC (Method 1): Retention time=0.83 min.

Example 136

6-(7-Amino-5-methyl-[1,2,5]oxadiazolo[3,4-b]pyridin-6-ylmethyl)-2-morpholin-4-yl-nicotinonitrile

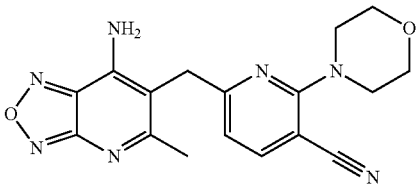

Obtained analogously to example 121 by starting from 6-(7-amino-5-methyl-[1,2,5]oxadiazolo[3,4-b]pyridin-6-ylmethyl)-2-chloro-nicotinonitrile (example 24) and morpholine.

Yield: 41% of theory

Mass spectrometry (ESI$^+$): m/z=352 $[M+H]^+$

HPLC (Method 10): Retention time=0.68 min.

Example 137

6-(7-Amino-5-methyl-[1,2,5]oxadiazolo[3,4-b]pyridin-6-ylmethyl)-2-(2-oxa-6-aza-spiro[3.3]hept-6-yl)-nicotinonitrile

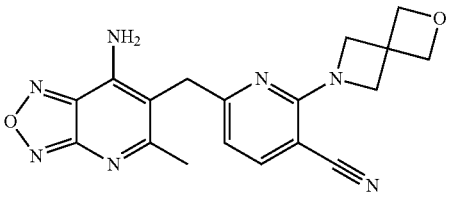

Obtained analogously to example 121 by starting 6-(7-amino-5-methyl-[1,2,5]oxadiazolo[3,4-b]pyridin-6-ylmethyl)-2-chloro-nicotinonitrile (example 24) and 2-oxa-6-aza-spiro[3,3]heptane oxalic acid salt using diisopropylethylamine instead of potassium fluoride.

Yield: 58% of theory

Mass spectrometry (ESI$^+$): m/z=364 $[M+H]^+$

HPLC (Method 1): Retention time=0.82 min.

Example 138

6-(7-Amino-5-methyl-[1,2,5]oxadiazolo[3,4-b]pyridin-6-ylmethyl)-2-(3-hydroxy-3-methyl-azetidin-1-yl)-nicotinonitrile

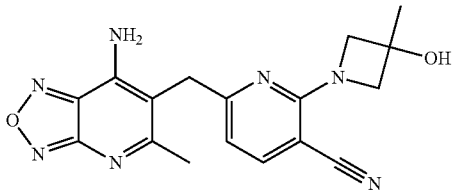

Obtained analogously to example 121 by starting 6-(7-amino-5-methyl-[1,2,5]oxadiazolo[3,4-b]pyridin-6-ylmethyl)-2-chloro-nicotinonitrile (example 24) and 3-methyl-3-azetidinol using triethylamin instead of potassium fluoride.

Yield: 72% of theory

Mass spectrometry (ESI$^+$): m/z=352 $[M+H]^+$

HPLC (Method 1): Retention time=0.82 min.

Example 139

6-(7-Amino-5-methyl-[1,2,5]oxadiazolo[3,4-b]pyridin-6-ylmethyl)-2-cyclopropylamino-nicotinonitrile

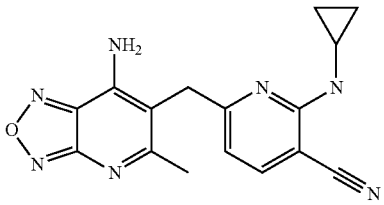

Obtained analogously to example 121 by starting from 6-(7-amino-5-methyl-[1,2,5]oxadiazolo[3,4-b]pyridin-6-ylmethyl)-2-chloro-nicotinonitrile (example 24) and cyclopropylamine.

Yield: 27% of theory

Mass spectrometry (ESI$^+$): m/z=322 $[M+H]^+$

HPLC (Method 1): Retention time=0.83 min.

Example 140

6-(7-Amino-5-methyl-[1,2,5]oxadiazolo[3,4-b]pyridin-6-ylmethyl)-2-(3,3-difluoro-cyclobutylamino)-nicotinonitrile

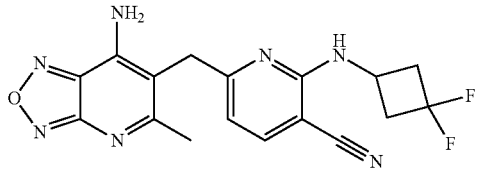

Obtained analogously to example 121 by starting 6-(7-amino-5-methyl-[1,2,5]oxadiazolo[3,4-b]pyridin-6-ylmethyl)-2-chloro-nicotinonitrile (example 24) and 3,3-difluoro-cyclobutylamine using diisopropylethylamine instead of potassium fluoride.

Yield: 67% of theory

Mass spectrometry (ESI$^+$): m/z=372 [M+H]$^+$

HPLC (Method 1): Retention time=0.93 min.

Example 141

6-(7-Amino-5-methyl-[1,2,5]oxadiazolo[3,4-b]pyridin-6-ylmethyl)-2-(5-oxo-[1,4]diazepan-1-yl)-nicotinonitrile

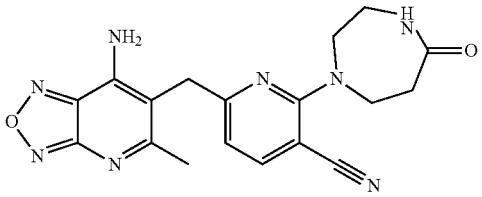

Obtained analogously to example 121 by starting 6-(7-amino-5-methyl-[1,2,5]oxadiazolo[3,4-b]pyridin-6-ylmethyl)-2-chloro-nicotinonitrile (example 24) and [1,4]diazepam-5-one using diisopropylethylamine instead of potassium fluoride.

Yield: 68% of theory

Mass spectrometry (ESI$^+$): m/z=379 [M+H]$^+$

HPLC (Method 1): Retention time=0.74 min.

Example 142 6-(7-Amino-5-methyl-[1,2,5]oxadiazolo[3,4-b] pyridin-6-ylmethyl)-2-(3,3-difluoro-azetidin-1-yl)-nicotinonitrile

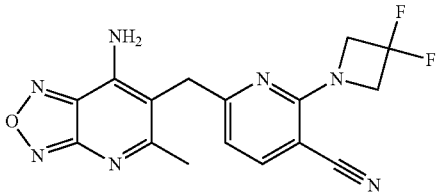

Obtained analogously to example 121 by starting 6-(7-amino-5-methyl-[1,2,5]oxadiazolo[3,4-b]pyridin-6-ylmethyl)-2-chloro-nicotinonitrile (example 24) and 3,3-Difluoro-azetidine hydrochloric salt using diisopropylethylamine instead of potassium fluoride.

Yield: 63% of theory

Mass spectrometry (ESI$^+$): m/z=358 [M+H]$^+$

HPLC (Method 1): Retention time=0.91 min.

Example 143

6-(7-Amino-5-methyl-[1,2,5]oxadiazolo[3,4-b]pyridin-6-ylmethyl)-2-(3,3-difluoro-pyrrolidin-1-yl)-nicotinonitrile

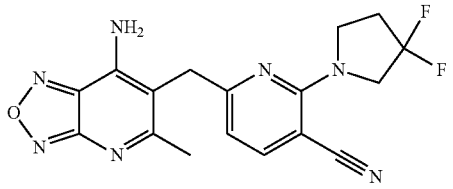

Obtained analogously to example 121 by starting from 6-(7-amino-5-methyl-[1,2,5]oxadiazolo[3,4-b]pyridin-6-ylmethyl)-2-chloro-nicotinonitrile (example 24), 3,3-Difluoro-pyrrolidine hydrochloride and additional diisopropylethylamine.

Yield: 69% of theory

Mass spectrometry (ESI$^+$): m/z=372 [M+H]$^+$

HPLC (Method 1): Retention time=0.93 min.

Example 144

6-(7-Amino-5-methyl-[1,2,5]oxadiazolo[3,4-b]pyridin-6-ylmethyl)-2-(3,3-difluoro-propylamino)-nicotinonitrile

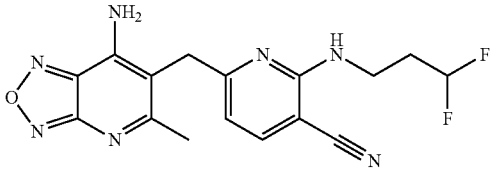

Obtained analogously to example 121 by starting from 6-(7-amino-5-methyl-[1,2,5]oxadiazolo[3,4-b]pyridin-6-ylmethyl)-2-chloro-nicotinonitrile (example 24), 3,3-difluoro-propylamine hydrochloride salt and diisopropylethylamine. Stirred for 30 minutes at 150° C. quenched with methanol, filtered and purified by RP-HPLC (modifier: ammonium hydroxide).

Yield: 85% of theory

Mass spectrometry (ESI$^+$): m/z=360 [M+H]$^+$

HPLC (Method 1): Retention time=0.88 min.

Example 145

6-(7-Amino-5-methyl-[1,2,5]oxadiazolo[3,4-b]pyridin-6-ylmethyl)-2-(3,3,3-trifluoro-propylamino)-nicotinonitrile

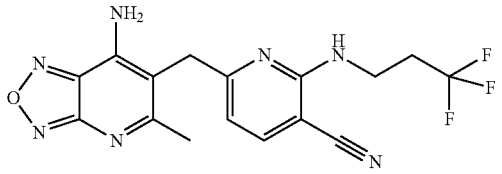

Obtained analogously to example 121 by starting from 6-(7-amino-5-methyl-[1,2,5]oxadiazolo[3,4-b]pyridin-6-ylmethyl)-2-chloro-nicotinonitrile (example 24), 3,3,3-trifluoro-propylamine hydrochloride salt and additional diisopropylethylamine.

Yield: 77% of theory

Mass spectrometry (ESI$^+$): m/z=378 $[M+H]^+$

HPLC (Method 1): Retention time=0.91 min.

Example 146

6-(7-Amino-5-methyl-[1,2,5]oxadiazolo[3,4-b]pyridin-6-ylmethyl)-2-(2-cyano-2,2-dimethyl-ethylamino)-nicotinonitrile

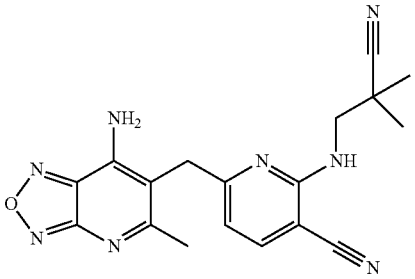

Obtained analogously to example 121 by starting from 6-(7-amino-5-methyl-[1,2,5]oxadiazolo[3,4-b]pyridin-6-ylmethyl)-2-chloro-nicotinonitrile (example 24) and 3-amino-2,2-dimethyl-propionitrile.

Yield: 37% of theory

Mass spectrometry (ESI$^+$): m/z=363 $[M+H]^+$

HPLC (Method 1): Retention time=0.86 min.

Example 147

6-(7-Amino-5-methyl-[1,2,5]oxadiazolo[3,4-b]pyridin-6-ylmethyl)-2-[(3-methyl-tetrahydro-furan-3-ylmethyl)-amino]-nicotinonitrile

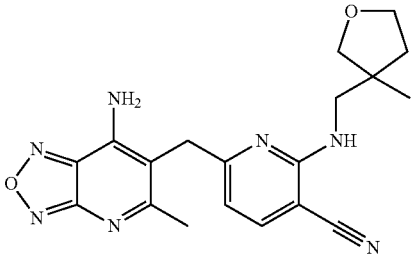

Obtained analogously to example 121 by starting from 6-(7-amino-5-methyl-[1,2,5]oxadiazolo[3,4-b]pyridin-6-ylmethyl)-2-chloro-nicotinonitrile (example 24) and C-(3-methyl-tetrahydro-furan-3-yl)-methylamine.

Yield: 60% of theory

Mass spectrometry (ESI$^+$): m/z=380 $[M+H]^+$

HPLC (Method 1): Retention time=0.88 min.

Example 148

3-[6-(7-Amino-5-methyl-[1,2,5]oxadiazolo[3,4-b]pyridin-6-ylmethyl)-3-cyano-pyridin-2-ylamino]-2,2-dimethyl-propionamide

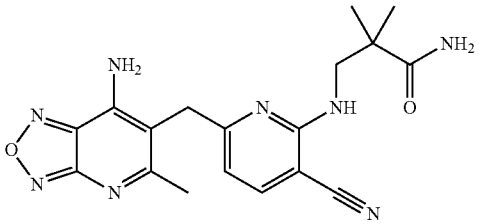

Obtained analogously to example 121 by starting from 6-(7-amino-5-methyl-[1,2,5]oxadiazolo[3,4-b]pyridin-6-ylmethyl)-2-chloro-nicotinonitrile (example 24) and 3-Amino-2,2-dimethyl-propionamide.

Yield: 68% of theory

Mass spectrometry (ESI$^+$): m/z=381 $[M+H]^+$

HPLC (Method 1): Retention time=0.79 min.

Example 149

6-(7-Amino-5-methyl-[1,2,5]oxadiazolo[3,4-b]pyridin-6-ylmethyl)-2-(3-fluoro-propylamino)-nicotinonitrile

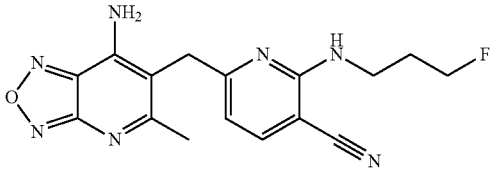

Obtained analogously to example 121 by starting from 6-(7-amino-5-methyl-[1,2,5]oxadiazolo[3,4-b]pyridin-6-ylmethyl)-2-chloro-nicotinonitrile (example 24), 3-Fluoro-propylamine hydrochloride salt and additional diisopropylethylamine. Stirred for 30 minutes at 150° C., quenched with methanol, filtered and purified by RP-HPLC (modifier: ammonium hydroxide).

Yield: 75% of theory

Mass spectrometry (ESI$^+$): m/z=342 $[M+H]^+$

HPLC (Method 1): Retention time=0.89 min.

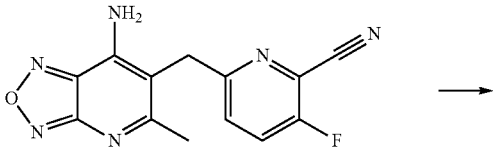

Ex. 25

-continued

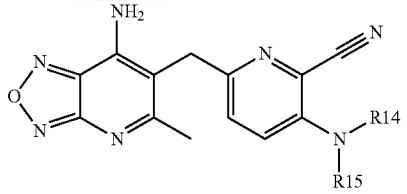

Examples 150-157

Example 150

6-(7-Amino-5-methyl-[1,2,5]oxadiazolo[3,4-b]pyridin-6-ylmethyl)-3-(3,3-difluoro-pyrrolidin-1-yl)-pyridine-2-carbonitrile

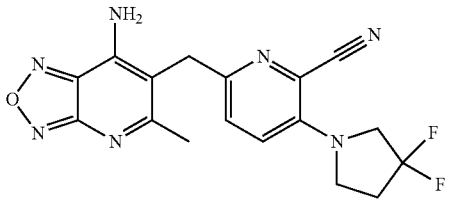

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 3,3-difluoro-pyrrolidine hydrochloric salt using diisopropylethylamine instead of potassium fluoride.

Yield: 39% of theory

Mass spectrometry (ESI$^+$): m/z=372 $[M+H]^+$

HPLC (Method 5): Retention time=0.74 min.

Example 151

6-(7-Amino-5-methyl-[1,2,5]oxadiazolo[3,4-b]pyridin-6-ylmethyl)-3-(3,3-difluoro-azetidin-1-yl)-pyridine-2-carbonitrile

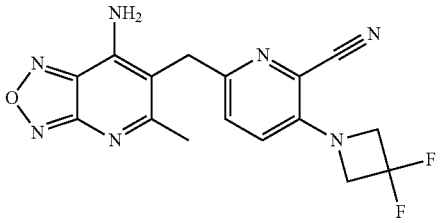

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 3,3-difluoro-azetidine hydrochloric salt using diisopropylethylamine instead of potassium fluoride.

Yield: 38% of theory

Mass spectrometry (ESI$^+$): m/z=358 $[M+H]^+$

HPLC (Method 5): Retention time=0.72 min.

Example 152

6-(7-Amino-5-methyl-[1,2,5]oxadiazolo[3,4-b]pyridin-6-ylmethyl)-3-morpholin-4-yl-pyridine-2-carbonitrile

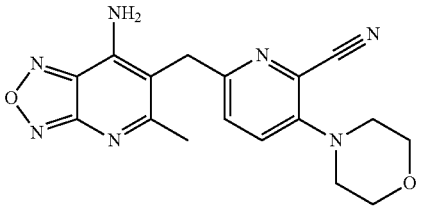

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and morpholine using diisopropylethylamine instead of potassium fluoride.

Yield: 35% of theory

Mass spectrometry (ESI$^+$): m/z=352 $[M+H]^+$

HPLC (Method 5): Retention time=0.64 min.

Example 153

6-(7-Amino-5-methyl-[1,2,5]oxadiazolo[3,4-b]pyridin-6-ylmethyl)-3-(2-fluoro-ethylamino)-pyridine-2-carbonitrile

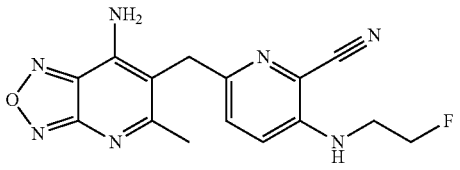

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 2-fluoro-ethylamine hydrochloric salt using diisopropylethylamine instead of potassium fluoride.

Yield: 31% of theory

Mass spectrometry (ESI$^+$): m/z=328 $[M+H]^+$

HPLC (Method 1): Retention time=0.83 min.

Example 154

6-(7-Amino-5-methyl-[1,2,5]oxadiazolo[3,4-b]pyridin-6-ylmethyl)-3-(2,2-difluoro-ethylamino)-pyridine-2-carbonitrile

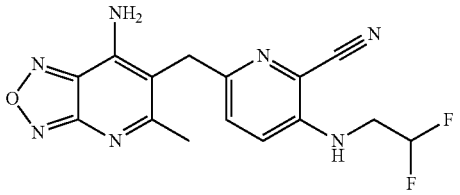

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 2,2-difluoro-ethylamine using diisopropylethylamine instead of potassium fluoride.

Yield: 17% of theory

Mass spectrometry (ESI$^+$): m/z=346 $[M+H]^+$

HPLC (Method 1): Retention time=0.86 min.

Example 155

6-(7-Amino-5-methyl-[1,2,5]oxadiazolo[3,4-b]pyridin-6-ylmethyl)-3-(4-fluoro-pyrazol-1-yl)-pyridine-2-carbonitrile

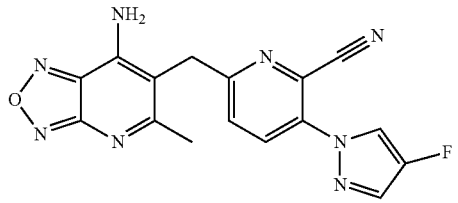

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 4-fluoro-1H-pyrazole using diisopropylethylamine instead of potassium fluoride.

Yield: 28% of theory

Mass spectrometry (ESI$^+$): m/z=351 $[M+H]^+$

HPLC (Method 1): Retention time=0.87 min.

Example 156

6-(7-Amino-5-methyl-[1,2,5]oxadiazolo[3,4-b]pyridin-6-ylmethyl)-3-(3-trifluoromethyl-pyrazol-1-yl)-pyridine-2-carbonitrile

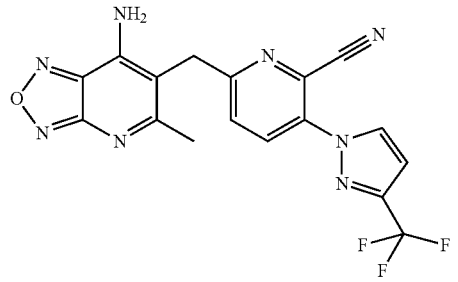

Obtained analogously to example 121 by starting 6-(7-amino-5-methyl-[1,2,5]oxadiazolo[3,4-b]pyridin-6-ylmethyl)-3-fluoro-pyridine-2-carbonitrile (example 25) and 3-trifluoromethyl-1H-pyrazole using diisopropylethylamine instead of potassium fluoride.

Yield: 18% of theory

Mass spectrometry (ESI$^+$): m/z=401 $[M+H]^+$

HPLC (Method 13): Retention time=0.65 min.

Example 157

6-(7-Amino-5-methyl-[1,2,5]oxadiazolo[3,4-b]pyridin-6-ylmethyl)-3-pyrazol-1-yl-pyridine-2-carbonitrile

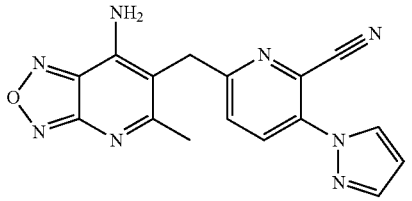

Obtained analogously to example 121 by starting 6-(7-Amino-5-methyl-[1,2,5]oxadiazolo[3,4-b]pyridin-6-ylmethyl)-3-fluoro-pyridine-2-carbonitrile (example 25) and 1H-pyrazole using diisopropylethylamine instead of potassium fluoride.

Yield: 31% of theory

Mass spectrometry (ESI$^+$): m/z=333 $[M+H]^+$

HPLC (Method 1): Retention time=0.83 min.

Example 158

6-(7-Amino-5-methyl-[1,2,5]oxadiazolo[3,4-b]pyridin-6-ylmethyl)-pyridine-2,3-dicarbonitrile

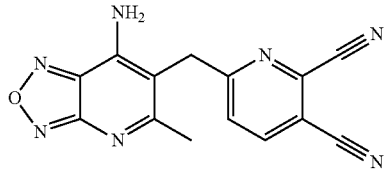

6-(7-Amino-5-methyl-[1,2,5]oxadiazolo[3,4-b]pyridin-6-ylmethyl)-2-fluoro-nicotinonitrile (example 72) (150.00 mg, 0.528 mmol) and potassium cyanide (51.543 mg, 0.792 mmol) are dissolved in 4 mL of dimethyl sulfoxide and stirred at room temperature for 1 hour. The mixture is extracted with ethyl acetate and washed with a half saturated aqueous solution of sodium bicarbonate. The organic phase is concentrated under reduced pressure and purified by silica gel chromatography (eluent: cyclohexane/ethyl acetate 100/0→45/65). The product is crystallized from ethyl acetate/cyclohexane=1/1 and collected by filteration.

Yield: 72% of theory

Mass spectrometry (ESI$^+$): m/z=292 $[M+H]^+$

HPLC (Method 1): Retention time=0.80 min.

Example 159

6-(7-Amino-5-methyl-[1,2,5]oxadiazolo[3,4-b]pyridin-6-ylmethyl)-3-methanesulfonyl-pyridin-2-ol

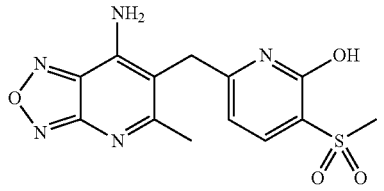

6-(5-Bromo-6-fluoro-pyridin-2-ylmethyl)-5-methyl-[1,2,5]oxadiazolo[3,4-b]pyridin-7-ylamine (example 22) (50.00 mg, 0.148 mmol) and sodium methanesulfinate (15.096 mg, 0.148 mmol) are dissolved in 0.909 mL of dimethyl sulfoxide and stirred for 1 hour at 100° C. in a microwave. The mixture is purified by RP-HPLC (modifier: ammonium hydroxide).

Yield: 8 mg (16% of theory)

Mass spectrometry (ESI$^+$): m/z=336 [M+H]$^+$

HPLC (Method 1): Retention time=0.55 min.

Example 160

6-(5,6-Bis-methanesulfonyl-pyridin-2-ylmethyl)-5-methyl-[1,2,5]oxadiazolo[3,4-b]pyridin-7-ylamine

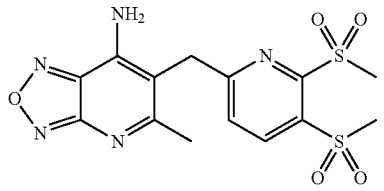

Analogously to example 159, obtained by starting from 6-(5-bromo-6-fluoro-pyridin-2-ylmethyl)-5-methyl-[1,2,5]oxadiazolo[3,4-b]pyridin-7-ylamine (example 22).

Yield: 13% of theory

Mass spectrometry (ESI$^+$): m/z=398 [M+H]$^+$

HPLC (Method 1): Retention time=0.63 min.

Example 161

6-(5-Bromo-6-methanesulfonyl-pyridin-2-ylmethyl)-5-methyl-[1,2,5]oxadiazolo[3,4-b]pyridin-7-ylamine

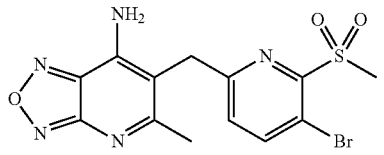

Analogously to example 159, obtained by starting from 6-(5-bromo-6-fluoro-pyridin-2-ylmethyl)-5-methyl-[1,2,5]oxadiazolo[3,4-b]pyridin-7-ylamine (example 22).

Yield: 8% of theory

Mass spectrometry (ESI$^+$): m/z=398, 399, 401 [M+H]$^+$

HPLC (Method 1): Retention time=0.71 min.

Example 162

6-(7-Amino-5-methyl-[1,2,5]oxadiazolo[3,4-b]pyridin-6-ylmethyl)-2-methanesulfonyl-nicotinonitrile

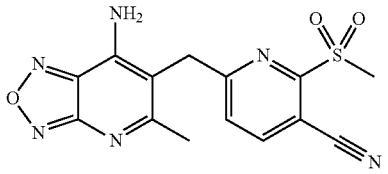

Analogously to example 159, obtained by starting from 6-(7-amino-5-methyl-[1,2,5]oxadiazolo[3,4-b]pyridin-6-ylmethyl)-2-fluoro-nicotinonitrile (example 72).

Yield: 24 mg (39% of theory)

Mass spectrometry (ESI$^+$): m/z=345 [M+H]$^+$

HPLC (Method 1): Retention time=0.70 min.

Example 163

6-(7-Amino-5-methyl-[1,2,5]oxadiazolo[3,4-b]pyridin-6-ylmethyl)-3-bromo-1H-pyridin-2-one

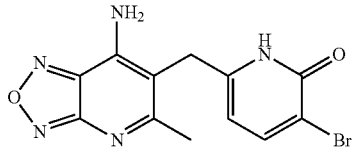

6-(5-Bromo-6-fluoro-pyridin-2-ylmethyl)-5-methyl-[1,2,5]oxadiazolo[3,4-b]pyridin-7-ylamine (example 22) (50.00 mg, 0.148 mmol) and potassium hydroxide (5 M aqueous solution) (0.10 ml, 0.35 mmol) are dissolved in 1.0 mL of dimethyl sulfoxide and stirred for 5 minutes at 120° C. The mixture is purified by RP-HPLC (modifier: ammonium hydroxide).

Yield: 36 mg (72% of theory)

Mass spectrometry (ESI$^+$): m/z=336, 338 [M+H]$^+$

HPLC (Method 1): Retention time=0.61 min.

Example 164

6-(7-Amino-5-methyl-[1,2,5]oxadiazolo[3,4-b]pyridin-6-ylmethyl)-pyridine-2-carbonitrile

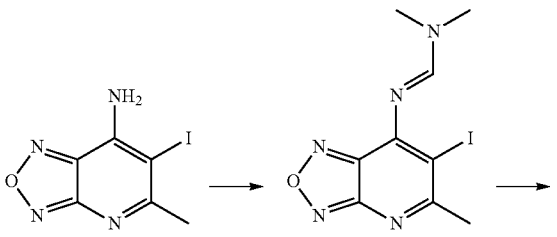

G 164.1

-continued

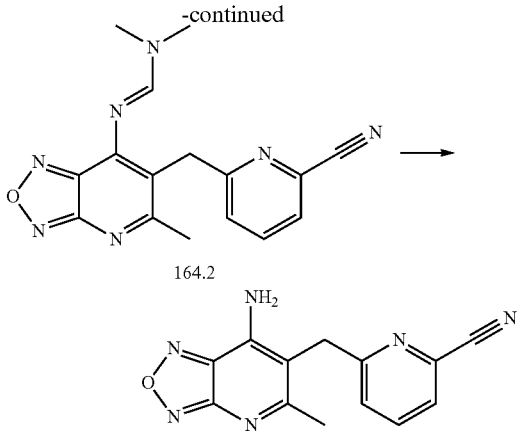

164.2

Ex. 164

164.1 N'-(6-Iodo-5-methyl-[1,2,5]oxadiazolo[3,4-b]pyridin-7-yl)-N,N-dimethyl-formamidine 6-Iodo-5-methyl-[1,2,5]oxadiazolo[3,4-b]pyridin-7-ylamine G (3.50 g, 12.7 mmol) is dissolved in 35 mL N,N-dimethylformamide and N,N-dimethylformamide dimethyl acetale (2.04 ml, 15.2 mmol) is added at room temperature. The mixture is stirred 1 hour, diluted with diethyl ether and the product is collected by filteration.

Yield: 2.57 g (61% of theory)

Mass spectrometry (ESI$^+$): m/z=332 [M+H]$^+$

HPLC (Method 12): Retention time=0.95 min.

164.2 N'-[6-(6-Cyano-pyridin-2-ylmethyl)-5-methyl-[1,2,5]oxadiazolo[3,4-b]pyridin-7-yl]-N,N-dimethyl-formamidine N'-(6-Iodo-5-methyl-[1,2,5]oxadiazolo[3,4-b]pyridin-7-yl)-N,N-dimethyl-formamidine 164.1 (100 mg, 0.302 mmol) and lithium acetylacetonate (3 mg, 0.030 mmol) are dissolved in 0.50 mL N-methyl-2-pyrrolidone. The reaction mixture is cooled to 0° C., diisopropylzinc solution (1 M solution in toluene, 0.166 ml, 0.166 mmol) is added and the reaction mixture is stirred at room temperature for 18 hours. [1,1'-bis(di-tert-butylphosphino)-ferrocene]palladium (II) dichloride (19 mg, 0.030 mmol) and 6-Bromomethyl-pyridine-2-carbonitrile (purchased from ABCR GmbH & Co. KG) (89 mg, 0.453 mmol) are added and the reaction mixture is stirred at 80° C. for 2 hours. The reaction mixture diluted with ethyl acetate, filtered over alox, concentrated under reduced pressure and purified by RP-HPLC (modifier: ammonium hydroxide).

Yield: 21 mg (21% of theory)

Mass spectrometry (ESI$^+$): m/z=322 [M+H]$^+$

HPLC (Method 1): Retention time=0.93 min.

Final Step (Example 164)

To N'-[6-(6-Cyano-pyridin-2-ylmethyl)-5-methyl-[1,2,5]oxadiazolo-[3,4-b]pyridin-7-yl]-N,N-dimethyl-formamidine 164.2 (20.00 mg, 0.062 mmol) in 10 mL of methanol is added 1.0 mL conc. hydrochloric acid and the reaction mixture is stirred for 2 hours at 60° C. The mixture is poured slowly into saturated aqueous solution of sodium bicarbonate and extracted with ethyl acetate. The organic phases are dried, concentrated under reduced pressure and the residue is purified by RP-HPLC (modifier: ammonium hydroxide).

Yield: 11 mg (70% of theory)

Mass spectrometry (ESI$^+$): m/z=267 [M+H]$^+$

HPLC (Method 1): Retention time=0.75 min.

Example 165

2-(7-amino-5-methyl-[1,2,5]oxadiazolo[3,4-b]pyridin-6-ylmethyl)-6-(difluoromethyl)pyrimidine-4-carbonitrile

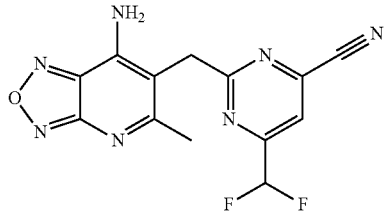

2-(7-amino-5-methyl-[1,2,5]oxadiazolo[3,4-b]pyridin-6-ylmethyl)pyrimidine-4-carbonitrile (example 51) (160 mg, 0.60 mmol) is dissolved in 6.0 mL dichloromethane and 2.0 mL water and zinc difluoromethanesulfinate (0.48 g, 1.62 mmol) is added. Trifluoroacetic acid (0.05 mL, 0.62 mmol) and 2-methyl-prop-2-yl-hydroperoxide (0.39 g, 2.99 mmol) are added and the mixture is stirred at room temperature for 18 hours. The solvent is concentrated under reduced pressure and the residue is purified by RP-HPLC (modifier: ammonium hydroxide)

Yield: 6.0 mg (3% of theory)

Mass spectrometry (ESI$^+$): m/z=318 [M+H]$^+$

HPLC (Method 1): Retention time=0.82 min.

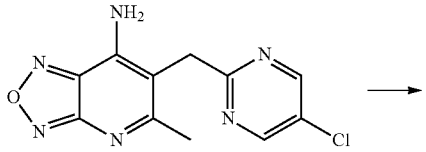

Ex. 30

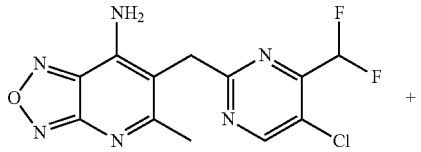

Ex. 166

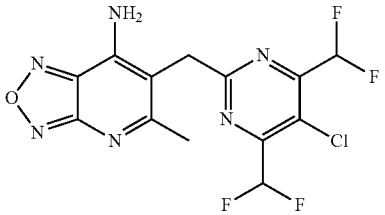

Ex. 167

Example 166

6-[5-chloro-4-(difluoromethyl)pyrimidin-2-yl] methyl-5-methyl-[1,2,5]oxadiazolo[3,4-b]pyridin-7-amine

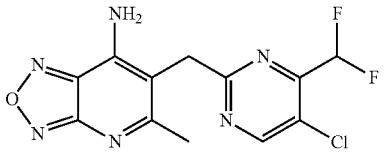

and

Example 167

6-[5-chloro-4,6-bis(difluoromethyl)pyrimidin-2-yl] methyl-5-methyl-[1,2,5]oxadiazolo[3,4-b]pyridin-7-amine

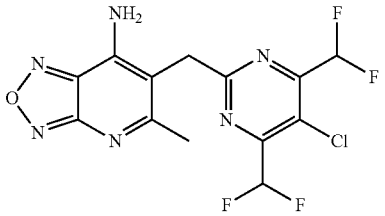

Analogously to example 80 obtained by starting from 6-(5-chloro-pyrimidin-2-ylmethyl)-5-methyl-[1,2,5]oxadiazolo[3,4-b]pyridin-7-ylamine (example 30) and zinc difluoromethanesulfinate. The mixture is purified by RP-HPLC (modifier: ammonium hydroxide)

6-[5-chloro-4-(difluoromethyl)pyrimidin-2-yl] methyl-5-methyl-[1,2,5]oxadiazolo[3,4-b]pyridin-7-amine Yield: 28% of theory Mass spectrometry (ESI$^-$): m/z=327 $[M+H]^+$ HPLC (Method 1): Retention time=0.88 min.

6-[5-chloro-4,6-bis(difluoromethyl)pyrimidin-2-yl] methyl-5-methyl-[1,2,5]oxadiazolo[3,4-b]pyridin-7-amine Yield: 11% of theory Mass spectrometry (ESI$^+$): m/z=377 $[M+H]^+$ HPLC (Method 1): Retention time=0.94 min.

The invention claimed is:

1. A method for treating obesity, type 2 diabetes mellitus, and/or insulin resistance, the method comprising administering to a patient in need thereof a pharmaceutically effective amount of a compound of formula (I)

[ (I)

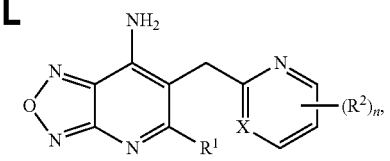

] *(I)* wherein

X is CH or N;

$R^1$ is selected from the group consisting of [$CH_3$—$CH_2OH$] *$CH_3$, —$CH_2OH$* and Cl;

$R^2$ is independently of each other selected from the group consisting of H, F, Cl, Br, I, CN, $C_{1-6}$-alkyl, $C_{3-7}$-cycloalkyl, OH, —O—($C_{1-6}$-alkyl), —O—($C_{3-7}$-cycloalkyl), [—O—($C_{1-3}$-alkyl)-($C_{3-7}$-cyclo alkyl)] *—O—($C_{1-3}$-alkyl)-($C_{3-7}$-cycloalkyl)*, —O-heterocyclyl, —O—($C_{1-3}$-alkyl)-heterocyclyl, —O-aryl, —O-heteroaryl, —S—($C_{1-3}$-alkyl), —SO—($C_{1-3}$-alkyl), [—$SO_{21-3}$-alkyl)] *—$SO_2$-($C_{1-3}$alkyl)*, —$NH_2$, —NH—($C_{1-6}$-alkyl), —NH—($C_{3-6}$-cycloalkyl), —NH—($C_{1-3}$-alkyl)-heterocyclyl, [—NH—($C_{1-6}$-alkyl-C(═O)—$NH_2$—C(═O)—$NH_2$—C(═O)—NH—($C_{1-3}$-alkyl)] *—NH—($C_{1-6}$-alkyl)-C(═O)—$NH_2$, —C(═O)—$NH_2$, —C(═O)—NH—($C_{1-3}$-alkyl)*, —C(═O)—N($C_{1-3}$-alkyl)$_2$, —C(═O)OH, *—C(═O)—O—($C_{1-4}$-alkyl)*, —C(═O)—($C_{1-4}$-alkyl), [alkyl)] *—$C_{1-3}$-alkyl-C(═O)—O—($C_{1-4}$-alkyl)*, heterocyclyl, heteroaryl and 5,6-dihydro-4H-pyrrolo[1,2-b]pyrazol-3-yl, wherein each alkyl or cycloalkyl group is optionally independently substituted with one or more substituents selected from the group consisting of F, CN and OH, and wherein each heterocyclyl group is selected from the group consisting of a mono- or spirocyclic 4-7-membered cycloalkyl group, in which 1, 2 or 3 $CH_2$-groups are independently of each other replaced by O, S, NH or C═O, and wherein each heterocyclyl group is optionally substituted with 1 or 2 substituents independently of each other selected from the group consisting of F, OH and $C_{1-3}$-alkyl, wherein each aryl group is selected from the group consisting of phenyl and naphthyl, and wherein each heteroaryl group is selected from the group consisting of *a* 5-membered aromatic cycle containing 1 or 2 heteroatoms independently selected from the group consisting of N, O and S or from a 6-membered aromatic cycle containing 1 or 2 N, and wherein each aryl or heteroaryl group is optionally substituted with 1 or 2 substituents independently selected from the group consisting of F, CN and $C_{1-3}$-alkyl, which is optionally substituted with one or more F;

or, if two groups $R^2$ are attached to adjacent C atoms of the pyridine or pyrimidine group, they may be linked with each other and together form a [O—$CH_2$—O—]

—*O—CH₂—O*—, —O—$CH_2$—$CH_2$—O— or —O—$CH_2$—$CH_2$—$CH_2$—O— bridge, in which 1 or [2H] *2 H* atoms may be replaced with F or $C_{1-3}$-alkyl; and n is 1, 2 or 3;

wherein each of the above-mentioned alkyl groups may be substituted with one or more F;

or a pharmaceutically acceptable salt thereof.

2. A method for treating a disease or condition which is mediated by inhibiting the activity of the ghrelin O-acyl transferase (GOAT), the method comprising administering a compound of formula (*I*)

[ (I)

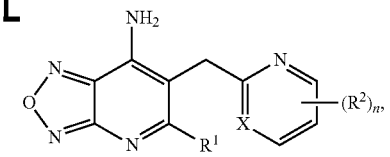

] (*I*)

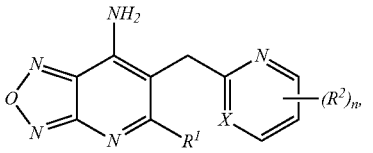

wherein

X is CH or N;

$R^1$ is selected from the group consisting of [$CH_3$—$CH_2OH$] *$CH_3$, —$CH_2OH$* and Cl;

$R^2$ is independently of each other selected from the group consisting of H, F, Cl, Br, I, CN, $C_{1-6}$-alkyl, $C_{3-7}$-cycloalkyl, OH, —O—($C_{1-6}$-alkyl), —O—($C_{3-7}$-cycloalkyl), —O—($C_{1-3}$-alkyl)-($C_{3-7}$-cycloalkyl), —O-heterocyclyl, —O—($C_{1-3}$-alkyl)-heterocyclyl, —O-aryl, —O-heteroaryl, —S—($C_{1-3}$-alkyl), —SO—($C_{1-3}$-alkyl), [—$SO_{21-3}$-alkyl)] *—$SO_2$—($C_{1-3}$-alkyl)*, —$NH_2$, —NH—($C_{1-6}$-alkyl), —NH—($C_{3-6}$-cycloalkyl), —NH—($C_{1-3}$-alkyl)-heterocyclyl, —NH—($C_{1-6}$-alkyl)-C(═O )—$NH_2$, —C(═O)—$NH_2$, —C(═O)—NH—($C_{1-3}$-alkyl), —C(═O)—N($C_{1-3}$-alkyl)$_2$, —C(═O)OH, —C(═O)—O—($C_{1-4}$-alkyl), —C(═O)—($C_{1-4}$-alkyl), [alkyl)] *—$C_{1-3}$-alkyl—C(═O)—O—($C_{1-4}$-alkyl)*, heterocyclyl, heteroaryl and 5,6-dihydro-4H-pyrrolo[1,2-b]pyrazol-3-yl, wherein each alkyl or cycloalkyl group is optionally independently substituted with one or more substituents selected from the group consisting of F, CN and OH, and wherein each heterocyclyl group is selected from the group consisting of a mono- or spirocyclic 4-7-membered cycloalkyl group, in which 1, 2 or 3 $CH_2$-groups are independently of each other replaced by O, S, NH or C═O, and wherein each heterocyclyl group is optionally substituted with 1 or 2 substituents independently of each other selected from the group consisting of F, OH and $C_{1-3}$-alkyl, wherein each aryl group is selected from the group consisting of phenyl and naphthyl, and wherein each heteroaryl group is selected from the group consisting of *a* 5-membered aromatic cycle containing 1 or 2 heteroatoms independently selected from the group consisting of N, O and S or from a 6-membered aromatic cycle containing 1 or 2 N, and wherein each aryl or heteroaryl group is optionally substituted with 1 or 2 substituents independently selected from the group consisting of F, CN and $C_{1-3}$-alkyl, which is optionally substituted with one or more F;

or, if two groups $R^2$ are attached to adjacent C atoms of the pyridine or pyrimidine group, they may be linked with each other and together form a [O—$CH_{2—O—}$] *—O—$CH_2$—O*—, —O—$CH_2$—$CH_2$—O— or —O—$CH_2$—$CH_2$—$CH_2$—O— bridge, in which 1 or [2H] *2 H* atoms may be replaced with F or $C_{1-3}$-alkyl; and n is 1, 2 or 3;

wherein each of the above-mentioned alkyl groups may be substituted with one or more F;

or a pharmaceutically acceptable salt thereof, to a patient in need thereof.

3. The method according to claim 1, wherein $R^1$ is —$CH_3$; and n is 1 or 2,

*or a pharmaceutically aceptable salt thereof.*

4. The method according to claim 1, wherein $R^2$ is independently of each other selected from the group consisting of H, F, Cl, Br, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), [—O— heterocyclyl] *—O-heterocyclyl*, —O—($C_{1-3}$-alkyl)-heterocyclyl, —O-aryl, —O-heteroaryl, —S—($C_{1-3}$-alkyl), —$SO_2$—($C_{1-3}$-alkyl), —$NH_2$, —NH—($C_{1-6}$-alkyl), —NH—($C_{3-6}$-cycloalkyl), —NH—($C_{1-3}$-alkyl)-heterocyclyl, —NH—($C_{1-6}$-alkyl)-C(═O)—$NH_2$, —C(═O)—$NH_2$, —C(═O)—NH—($C_{1-3}$-alkyl), —C(═O)—($C_{1-4}$-alkyl), —$C_{1-3}$-alkyl-C(═O)—O—($C_{1-4}$-alkyl), heterocyclyl, heteroaryl and 5,6-dihydro-4H-pyrrolo[1,2-b]pyrazol-3-yl, wherein each alkyl or cycloalkyl group is optionally independently substituted with one or more substituents selected from the group consisting of F, CN and OH, and wherein each heterocyclyl group is selected from the group consisting of a mono- or spirocyclic 4-7-membered cycloalkyl group, in which 1, 2 or 3 $CH_2$-groups are independently of each other replaced by O, S, NH or C═O, and wherein each heterocyclyl group is optionally substituted with 1 or 2 substituents independently of each other selected from the group consisting of F, OH and $C_{1-3}$-alkyl, wherein each aryl group is selected from the group consisting of phenyl and naphthyl, and wherein each heteroaryl group is selected from the group consisting of *a* 5-membered aromatic cycle containing 1 or 2 heteroatoms independently selected from the group consisting of N, O and S or from a 6-membered aromatic cycle containing 1 or 2 N, and wherein each aryl or heteroaryl group is optionally substituted with 1 or 2 substituents independently selected from the group consisting of F and $C_{1-3}$-alkyl, which is optionally substituted with one or more F;

or, if two groups $R^2$ are attached to adjacent C atoms of the pyridine or pyrimidine group, they may be linked with each other and together form a —O—$CH_2$—O—, —O—$CH_2$—$CH_2$—O— or [—O —$CH_2$—$CH_2$—$CH_2$—O—] —*O*—*CH*$_2$—*CH*$_2$—*CH*$_2$—*O*— bridge,

*or a pharmaceutically acceptable salt thereof.*

5. The method according to claim 4, wherein $R^2$ is independently of each other selected from the group consisting of F, Cl, Br, CN, $C_{1-3}$-alkyl, $C_{3-6}$-cycloalkyl, —O—($C_{1-4}$-alkyl), —O—$CH_2$-cyclopropyl, —O—$CH_2$-heterocyclyl, —O-phenyl, —O-heteroaryl, —S—$CH_3$, —$NH_2$, —NH—($C_{1-4}$-alkyl), —NH—($C_{3-5}$-cycloalkyl), —NH—($CH_2$-heterocyclyl), —NH—($C_{1-4}$-alkyl)-C(=O)—$NH_2$, —C(=O)—NH—($C_{1-3}$-alkyl), —C(=O)—($C_{1-4}$-alkyl), heterocyclyl, heteroaryl and 5,6-dihydro-4H-pyrrolo[1,2-b]pyrazol-3-yl, wherein each alkyl or cycloalkyl group is optionally independently substituted with one to three F atoms or with one CN or one OH, and wherein each heterocyclyl group is selected from the group consisting of oxetanyl, tetrahydrofuranyl, azetidinyl, pyrrolidinyl, morpholinyl and 1,4-diazepan-5-one, and wherein each heterocyclyl group is optionally substituted with 1 or 2 substituents independently of each other selected from the group consisting of F, OH and $CH_3$, wherein each heteroaryl group is selected from the group consisting of furanyl, isoxazolyl, thiazolyl and pyrazolyl, and wherein each heteroaryl group is optionally substituted with 1 or 2 substituents independently selected from the group consisting of F, $CH_3$ and $CF_3$,

*or a pharmaceutically acceptable salt thereof.*

6. The method according to claim 5, wherein $R^2$ is independently of each other selected from the group consisting of F, Cl, Br, CN, $CH_3$, $C_{3-5}$-cycloalkyl, —O—($C_{1-4}$-alkyl), —O—$CH_2$-heterocyclyl, —O-phenyl, —S—$CH_3$, —$NH_2$, —NH—($C_{1-4}$-alkyl), —NH—($C_{3-5}$-cycloalkyl), —NH—($CH_2$-heterocyclyl), —NH—($C_{1-4}$-alkyl)-C(=O)—$NH_2$, heterocyclyl, heteroaryl and 5,6-dihydro-4H-pyrrolo[1,2-b]pyrazol-3-yl, wherein each alkyl or cycloalkyl group is optionally independently substituted with one to three F atoms or with one CN or one OH, and wherein each heterocyclyl group is selected from the group consisting of oxetanyl, azetidinyl, pyrrolidinyl, morpholinyl and 1,4-diazepan-5-one, and wherein each heterocyclyl group is optionally substituted with 1 or 2 substituents independently selected from the group consisting of F, OH and $CH_3$, and wherein each heteroaryl group is selected from the group consisting of furanyl and thiazolyl,

*or a pharmaceutically acceptable salt thereof.*

7. The method according to claim 6, wherein $R^2$ is independently selected from the group consisting of: F, Cl, Br, —CN, —$CF_3$,

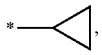

—O—$CH_3$, —O—$CHF_2$, —O—$CH_2$—$CH_2$—F, —O—$CH_2$—$CHF_2$, —O—$CH_2$—$CF_3$, —O—$CH_2$—$CH_2$—$CH_2$—F, —O—$CH_2$—$CF_2$—$CH_3$,

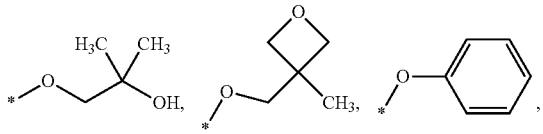

—S—$CH_3$, —$NH_2$, —NH—$CH_2$—$CH_2$—$CH_2$—F, —NH—$CH_2$—$CH_2$—$CHF_2$,

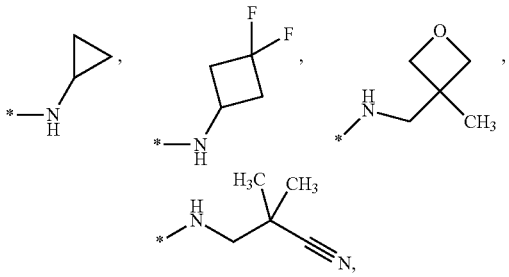

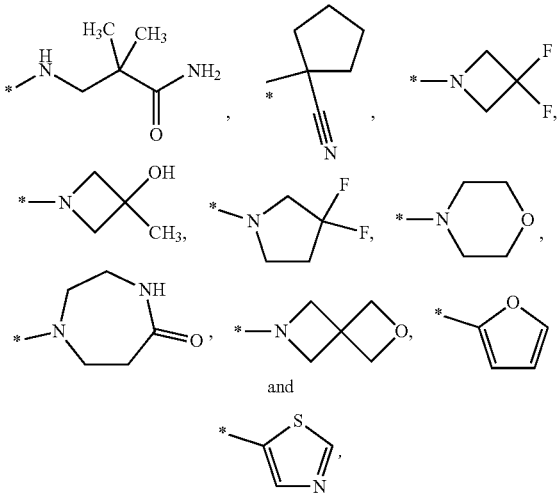

and

*or a pharmaceutically acceptable salt thereof.*

8. The method according to claim 1, where X is CH, *or a pharmaceutically acceptable salt thereof.*

9. The method according to claim 1, where X is N, *or a pharmaceutically acceptable salt thereof.*

10. The method according to claim 1, where the compound of formula (I) is of formula I.2

(I.2)

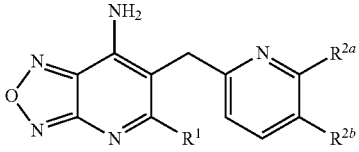

wherein $R^1$ is $CH_3$;

$R^{2a}$ and $R^{2b}$ are each independently selected from the group consisting of:

H, F, Cl, Br, CN, —$CF_3$,

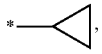
—O—$CH_3$, —O—$CHF_2$, —O—$CH_2$—$CH_2$—F, —O—$CH_2$—$CHF_2$, —O—$CH_2$—$CF_3$, —O—$CH_2$—$CH_2$—$CH_2$—F, —O—$CH_2$—$CF_2$—$CH_3$,
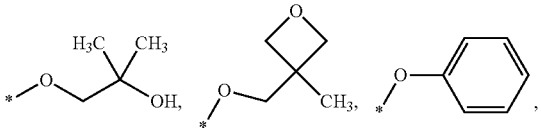
—S—$CH_3$, —$NH_2$, —NH—$CH_2$—$CH_2$—$CH_2$—F, —NH—$CH_2$—$CH_2$—$CHF_2$,
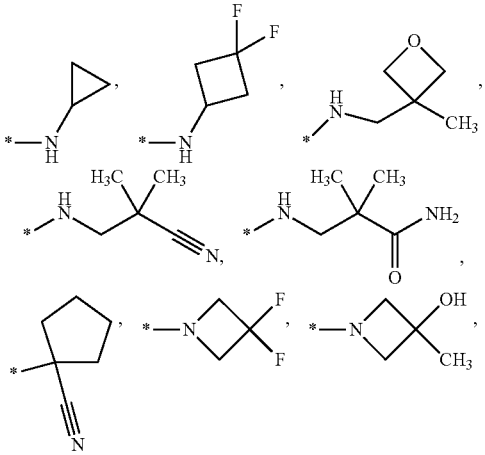
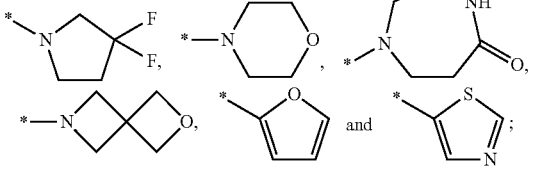
wherein at least one $R^{2a}$ and $R^{2b}$ is not H;
or a *pharmaceutically acceptable* salt thereof.
11. The method according to claim 1, wherein the compound of formula I is selected from the group consisting of:
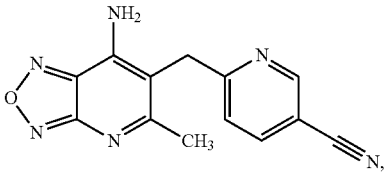
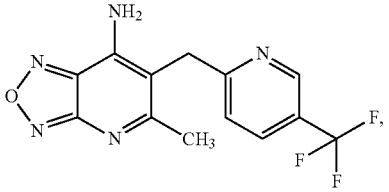
-continued
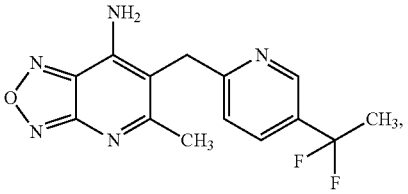
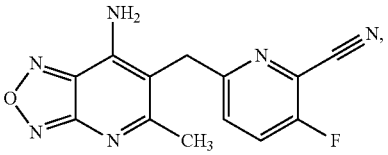
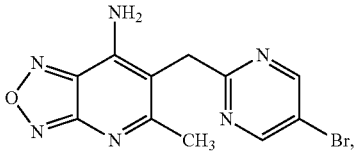
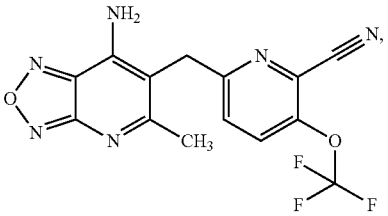
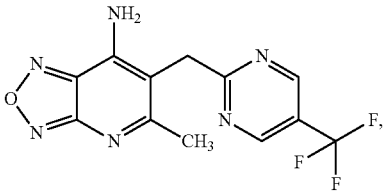
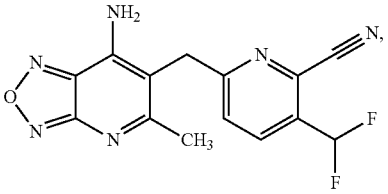
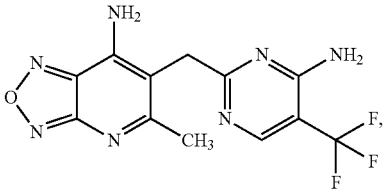
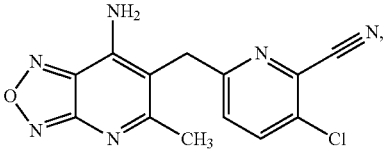
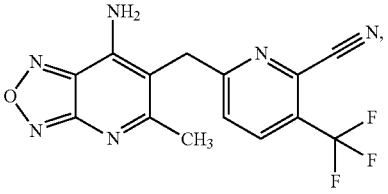

-continued

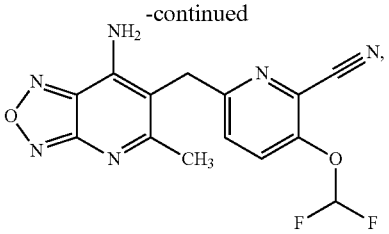

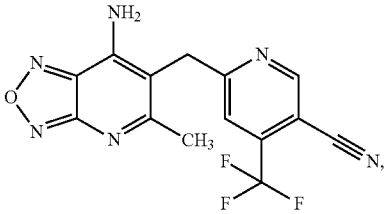

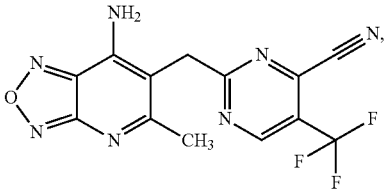

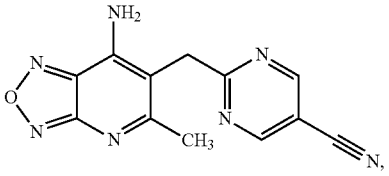

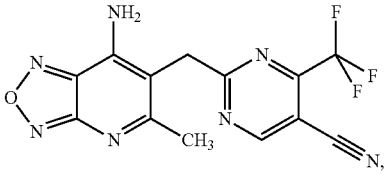

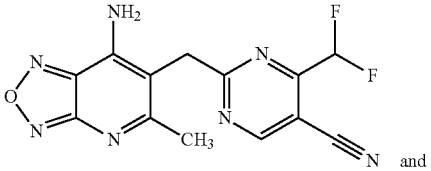

and

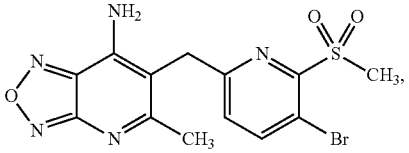

or a *pharmaceutically acceptable* salt thereof.

12. The method of claim 1, wherein *the* obesity patient is suffering from Prader-Willi syndrome.

*13. The method according to claim 10, wherein the compound is*

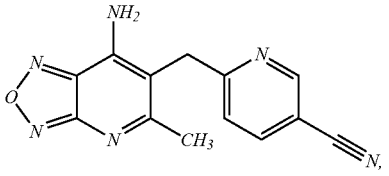

*or a pharmaceutically acceptable salt thereof.*

*14. The method according to claim 10, wherein the compound is*

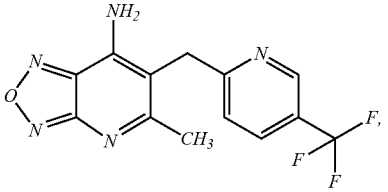

*or a pharmaceutically acceptable salt thereof.*

*15. The method according to claim 1, wherein the compound is*

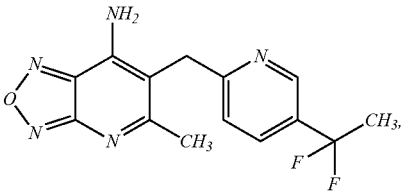

*or a pharmaceutically acceptable salt thereof.*

*16. The method according to claim 10, wherein the compound is*

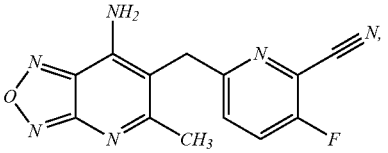

*or a pharmaceutically acceptable salt thereof.*

*17. The method according to claim 1, wherein the compound is*

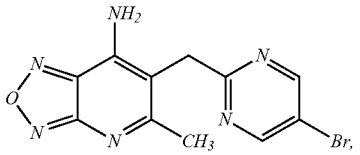

*or a pharmaceutically acceptable salt thereof.*

*18. The method according to claim 1, wherein the compound is*

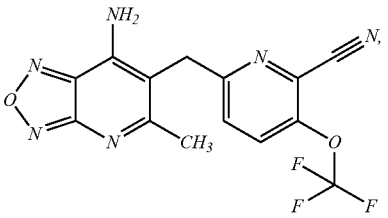

*or a pharmaceutically acceptable salt thereof.*

*19. The method according to claim 1, wherein the compound is*

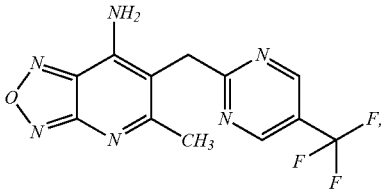

*or a pharmaceutically acceptable salt thereof.*

*20. The method according to claim 1, wherein the compound is*

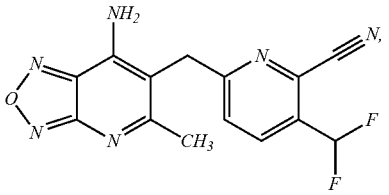

*or a pharmaceutically acceptable salt thereof.*

*21. The method according to claim 1, wherein the compound is*

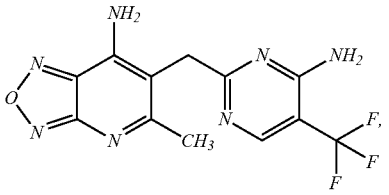

*or a pharmaceutically acceptable salt thereof.*

*22. The method according to claim 10, wherein the compound is*

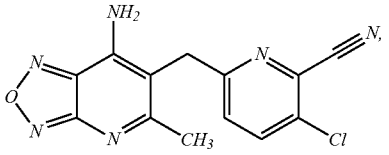

*or a pharmaceutically acceptable salt thereof.*

*23. The method according to claim 10, wherein the compound is*

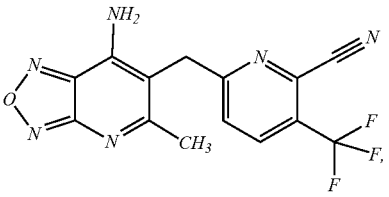

*or a pharmaceutically acceptable salt thereof.*

*24. The method according to claim 10, wherein the compound is*

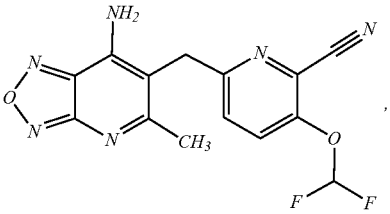

*or a pharmaceutically acceptable salt thereof.*

*25. The method according to claim 1, wherein the compound is*

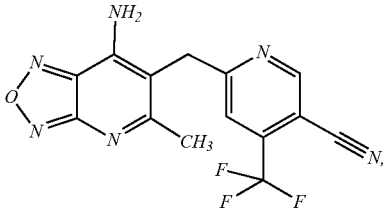

*or a pharmaceutically acceptable salt thereof.*

*26. The method according to claim 1, wherein the compound is*

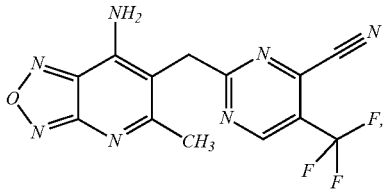

*or a pharmaceutically acceptable salt thereof.*

*27. The method according to claim 1, wherein the compound is*

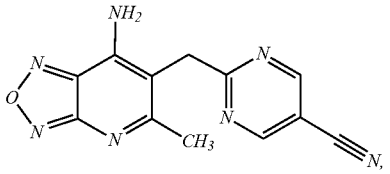

*or a pharmaceutically acceptable salt thereof.*

*28. The method according to claim 1, wherein the compound is*

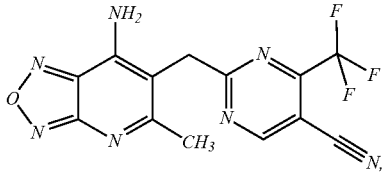

*or a pharmaceutically acceptable salt thereof.*

29. The method according to claim 1, wherein the compound is

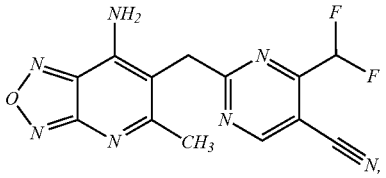

or a pharmaceutically acceptable salt thereof.

30. The method according to claim 1, wherein the compound is

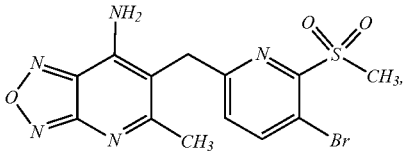

or a pharmaceutically acceptable salt thereof.

31. A method for treating obesity, type 2 diabetes mellitus, and/or insulin resistance, the method comprising administering to a patient in need thereof a pharmaceutically effective amount of a compound of formula

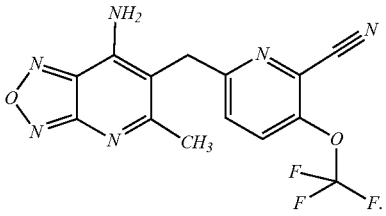

32. A method for treating obesity, type 2 diabetes mellitus, and/or insulin resistance, the method comprising administering to a patient in need thereof a pharmaceutically effective amount of a compound of formula

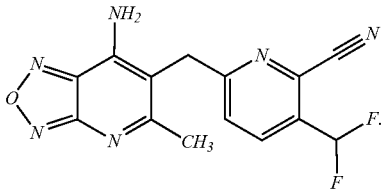

33. A method for treating obesity, type 2 diabetes mellitus, and/or insulin resistance, the method comprising administering to a patient in need thereof a pharmaceutically effective amount of a compound of formula

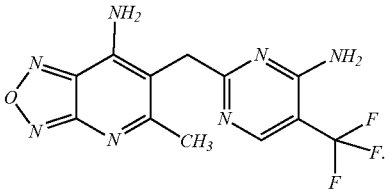

34. A method for treating obesity, type 2 diabetes mellitus, and/or insulin resistance, the method comprising administering to a patient in need thereof a pharmaceutically effective amount of a compound of formula

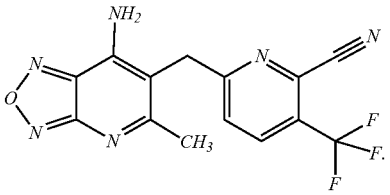

35. A method for treating obesity, type 2 diabetes mellitus, and/or insulin resistance, the method comprising administering to a patient in need thereof a pharmaceutically effective amount of a compound of formula

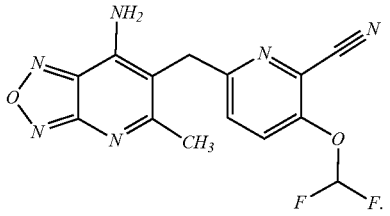

36. A method for treating obesity, type 2 diabetes mellitus, and/or insulin resistance, the method comprising administering to a patient in need thereof a pharmaceutically effective amount of a compound of formula

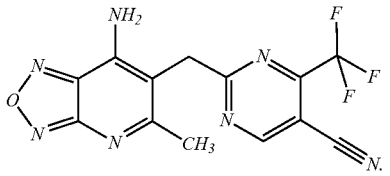

37. A method for treating obesity, type 2 diabetes mellitus, and/or insulin resistance, the method comprising administering to a patient in need thereof a pharmaceutically effective amount of a compound of formula

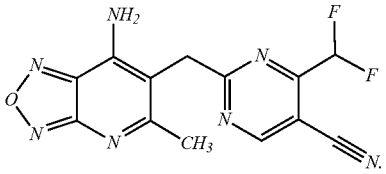
NH2
F
N
F
O
N
N
N
CH3
N.
* * * * *